(12) United States Patent
Chiao et al.

(10) Patent No.: US 7,399,787 B2
(45) Date of Patent: Jul. 15, 2008

(54) METHODS OF TREATING CANCER WITH HDAC INHIBITORS

(75) Inventors: Judy H. Chiao, Berkeley Heights, NJ (US); Nicholas G. Bacopoulos, New York, NY (US); Thomas A. Miller, New York, NY (US); Carolyn M. Paradise, Cortland Manor, NY (US); Victoria M. Richon, Rye, NY (US)

(73) Assignee: Merck HDAC Research, LLC, Boston, MA (US)

( * ) Notice: Subject to any disclaimer, the term of this patent is extended or adjusted under 35 U.S.C. 154(b) by 645 days.

(21) Appl. No.: 10/616,649

(22) Filed: Jul. 9, 2003

(65) Prior Publication Data

US 2004/0127522 A1 Jul. 1, 2004

(51) Int. Cl.
*A61K 31/19* (2006.01)
(52) U.S. Cl. .................................... 514/575
(58) Field of Classification Search ................ 514/575
See application file for complete search history.

(56) References Cited

U.S. PATENT DOCUMENTS

| | | | |
|---|---|---|---|
| 4,690,918 A | 9/1987 | Beppu et al. | |
| 5,055,608 A | 10/1991 | Marks et al. | 560/169 |
| 5,175,191 A | 12/1992 | Marks et al. | 514/575 |
| 5,369,108 A | 11/1994 | Breslow et al. | 514/266 |
| 5,608,108 A | 3/1997 | Marks et al. | 562/621 |
| 5,654,333 A | 8/1997 | Samid | |
| 5,700,811 A | 12/1997 | Breslow et al. | 514/314 |
| 5,773,474 A | 6/1998 | Breslow et al. | 514/616 |
| 5,932,616 A | 8/1999 | Breslow et al. | 514/532 |
| 6,087,367 A | 7/2000 | Breslow et al. | 514/266 |
| 6,231,880 B1 | 5/2001 | Perrine | 424/423 |
| 6,239,176 B1 | 5/2001 | Nudelman et al. | |
| 6,262,116 B1 | 7/2001 | Pandolfi et al. | |
| 6,451,334 B2 | 9/2002 | Perrine | |
| 6,495,719 B2 | 12/2002 | Lan-Hargest et al. | |
| 6,511,990 B1 | 1/2003 | Breslow et al. | 514/314 |
| RE38,506 E | 4/2004 | Breslow et al. | 514/316 |
| 6,905,669 B2 * | 6/2005 | DiMartino | 424/9.1 |
| 2003/0082666 A1 | 5/2003 | Kammer et al. | 435/18 |
| 2003/0114525 A1 | 6/2003 | Kammer et al. | |
| 2003/0161830 A1 | 8/2003 | Jackson et al. | |
| 2003/0235588 A1 * | 12/2003 | Richon et al. | 424/146.1 |
| 2004/0002506 A1 | 1/2004 | Breslow et al. | 514/310 |
| 2004/0018968 A1 | 1/2004 | Sgouros | 514/9 |
| 2004/0072735 A1 | 4/2004 | Richon et al. | 514/9 |
| 2004/0087631 A1 | 5/2004 | Bacopoulos et al. | 514/352 |
| 2004/0122101 A1 | 6/2004 | Miller et al. | 514/575 |
| 2004/0127522 A1 | 7/2004 | Chiao et al. | 514/352 |
| 2004/0127523 A1 | 7/2004 | Bacopoulos et al. | |
| 2004/0132643 A1 | 7/2004 | Fojo et al. | |
| 2004/0132825 A1 | 7/2004 | Bacopoulos et al. | 514/575 |
| 2004/0167184 A1 | 8/2004 | Wiech et al. | |
| 2004/0266818 A1 | 12/2004 | Breslow et al. | 514/263.4 |
| 2005/0004007 A1 | 1/2005 | Grant et al. | 514/7 |
| 2006/0167103 A1 | 7/2006 | Bacopoulos et al. | 514/575 |
| 2006/0276547 A1 | 12/2006 | Bacopoulos et al. | 514/575 |
| 2007/0060614 A1 | 3/2007 | Bacopoulos et al. | 514/352 |
| 2007/0190022 A1 | 8/2007 | Bacopoulos et al. | 424/85.1 |

FOREIGN PATENT DOCUMENTS

| | | |
|---|---|---|
| EP | 0547000 A1 | 6/2003 |
| WO | WO 95/31977 | 11/1995 |
| WO | WO 98/39965 | 9/1998 |
| WO | WO 98/40080 | 9/1998 |
| WO | WO 98/55449 | 12/1998 |
| WO | WO 00/21979 | 4/2000 |
| WO | WO 00/71703 | 11/2000 |
| WO | WO 01/16106 | 3/2001 |
| WO | WO 01/18171 | 3/2001 |
| WO | WO 01/38322 | 5/2001 |
| WO | WO 01/70675 | 9/2001 |
| WO | WO 02/15921 | 2/2002 |
| WO | WO 02/22577 | 3/2002 |
| WO | WO 02/30879 | 4/2002 |
| WO | WO 02/46144 | 6/2002 |
| WO | WO 02/055017 | 7/2002 |

(Continued)

OTHER PUBLICATIONS

Rubartelli et al. Cancer Research, 1995, vol. 55, pp. 675-680.*

(Continued)

*Primary Examiner*—Ardin Marschel
*Assistant Examiner*—James D Anderson
(74) *Attorney, Agent, or Firm*—Ivor R. Elrifi, Esq.; Mintz Levin Cohn Ferris Glovsky and Popeo PC

(57) ABSTRACT

The present invention provides methods of treating cancers, chemoprevention, selectively inducing terminal differentiation, cell growth arrest and/or apoptosis of neoplastic cells, and/or inhibiting histone deacetylase (HDAC) by administration of pharmaceutical compositions comprising potent HDAC inhibitors. The oral bioavailability of the active compounds in the pharmaceutical compositions of the present invention is surprisingly high. Moreover, the pharmaceutical compositions unexpectedly give rise to high, therapeutically effective blood levels of the active compounds over an extended period of time. The present invention further provides a safe, daily dosing regimen of these pharmaceutical compositions, which is easy to follow, and which results in a therapeutically effective amount of the HDAC inhibitors in vivo.

11 Claims, 19 Drawing Sheets

FOREIGN PATENT DOCUMENTS

WO    WO 02/085400 A1    10/2002

OTHER PUBLICATIONS

"Aton Pharma, Inc. Announces Initiation of Two Phase II Trials to Evaluate Efficacy of HDAC Inhibitor SAHA", Oct. 30, 2002.

"Aton Pharma, Inc. Announces Phase I Clinical Trial of SAHA in Advanced Leukemias", Jul. 1, 2003.

"Aton Pharma, Inc. Appoints Judy H. Chiao, M.D., as Vice President, Oncology Clinical Research and Development", Sep. 20, 2002.

"Aton Pharma, Inc. Presents Phase I Trial Data of Anti-Cancer Agent SAHA in Patients with hematological Malignancy at ASCO", Jun. 2, 2003.

"Aton Pharma, Inc. Presents Phase I Trial Data on Anti-Cancer Agent SAHA and EORTC/NCI/AACR Symposium", Nov. 21, 2002.

"Aton Pharma, Inc. Received Orphan Drug Designation for SAHA in Multiple Myeloma and Initiates Phase I Trial", Oct. 13, 2003.

"Aton Pharma, Inc. Reports on Phase I Trail of SAHA", Aug. 14, 2002.

Adhikari, D et al. Proceedings of the American Association for Cancer Research Annual Meeting, (1998), vol. 39, p. 312, "Radiosensitization of Lymphoma Cell Lines by Sodium Butyrate".

Alexandrov, I et al., FEBS Letters, (1998), vol. 434, pp. 209-214, "Sodium Butyrate Suppresses Apoptosis in Human Burkitt Lymphomas and Murine Plasmacytomas Bearing c-myc Translocations".

Almenara, J. et al., Leukemia (2002), vol. 16, pp. 1331-1343, "Synergistic Induction of Mitochondrial Damage and Apoptosis in Human Leukemia Cells by Flavopiridol and the Histone Deacetylase Inhibitor Suberoylanilide Hydroxamic Acid (SAHA)".

Amin Hm et al., British Journal of Haematology (2001), vol. 115, pp. 287-297, "Histone Deacetylase Inhibitors Induce Caspase-Dependent Apoptosis and Downregulation of Daxx in Acute Promyeloytic Leukaemia with t(15;17)".

Aron, JL et al., Blood (2003), vol. 102, No. 2, pp. 652-658, "Depsipeptide (FR901228) Induces Histone Acetylation and Inhibition of Histone Deacetylase in Chronic Lymphocytic Leukemia Cells Concurrent With Activation of Caspase 8-mediated Apoptosis and Down-Regulation of c-FLIP Protein".

Benoit, NE et al., Immunopharmacology, (1996), vol. 35, pp. 129-139, "Increased inhibition of Proliferation of Human B Cell Lymphomas Following Litigation of CD40, and Either CD19, CD20, CD95 or Surface Immunoglobulin".

Bode, J et al., Journal of Interferon Research, (1982), vol. 2, No. 2, pp. 159-166, "Links Between Effectsof Butyrate on Histone Hyperacetylation and Regulation of Interferon Synthesis in Namalva and FS-4 Cell Lines".

Buckley, AR et al., Cell Growth & Differentiation (1996), vol. 7, pp. 1713-1721, "Alteration in pim-1 and c-myc Expression Assoicated with Sodium Butyrate-induced Growth Factor Dependency in Autonomous Rat Nb2 Lymphoma Cells".

Buckley, AR et al., Proceedings of the American Association for Cancer Research Annual Meeting, (1997), vol. 38, p. 193, "Reversal of Apoptosis Resistance by Butyrate in rat Nb2 Lymphoma Cells".

Byrd, JC et al., Blood (1999), vol. 94, No. 4, pp. 1401-1408, "Depsipeptide (FR901228): A Novel Therapeutic Agent with Selective, In Vitro Activity Against Human B-Cell Lymphocytic Leukemia Cells".

Cao, et al. (2001), Am. J. Respir. Cell Mol. Biol., 25:562-8, "Histone Deacetylase Inhibitor Downregulation of bcl-xl Gene Expression Leads to Apoptosis Cell Death in Mesothelioma".

Carducci, MA et al., Clinical Cancer Research (2001), vol. 7, No. 10 pp. 3047-3055, "A Phase I Clincal and Pharmacological Evaluation of Sodium Phenylbutyrate on an 120-h Infusion Schedule".

Dear, AE et al., Biochimica et Biophysics Acta, (2000), vol. 1492, pp. 15-22, "The Novel Anti-Tumor Agent Oxamfatin Differentially Regulates Urokinase and Plasminogen Activator Inhibitor Type 2 Expression and Inhibits Urokinase-Mediated Proteolytic Activity".

Desai, D et al., Anticancer Research (2003), vol. 23, pp. 499-504, "Chemopreventive Efficacy of Suberoylanilide Hydroxamic Acid (SAHA) Against 4-(Methylnitrosamino)-1-(3-pyridyl)-1-butanone (NNK)-induced Lung Tumorigenesis in Female A/J Mice".

Dhordain, P et al., Nucleic Acids Research, (1998), vol. 26, No. 20, pp. 4645-4651, "The LAZ3(BCL-6) Oncoprotein Recruits a SMRT/mSIN3A/Histone Deacetylase Containing Complex to Mediate Transcriptional Repression".

Edelman, MJ et al., Cancer Chemotherapy and Pharmacology (2003), vol. 51, pp. 439-444, "Clinical and Pharmacologic Study of Tributyrin: An Oral Butyrate Prodrug".

Feinman, R et al., Blood (2002), vol. 100, No. 11, pp Abstract 3195, "The Histone Deacetylast Inhibitor, Suberoylanilide Hydroxyamic Acid, Induces Apoptosis of Multiple Myeloma Cells".

Fillppovich, I et al., Biochemical and Biophysical Research Communications, (1994), vol. 198, pp. 257-265, "Butyrate Induce Apoptosis in Lymphoid Cells Preceded by Transient Over-Expression of HSP70 mRNA".

Foss, FM et al., Blood, (1993), vol. 82, No. 10, Suppl. 1, p. 564A, "Biomodulatory Effects of Butyric Acid Derivatives on Leukemia and Lymphoma Cells".

Gediya, et al., J. Med. Chem. (2005), vol. 48, pp. 5047-5051, "A New Simple and High-Yield Synthesis of Suberoylanilide Hydroxamic Acid and Its Inhibitory Effect Alone or in Combination with Retinoids on Proliferation of Humans Prostate Cancer Cells".

Gelmetti, V et al., Molecular and Cellular Biology (1998), vol. 1, No. 12, pp. 7185-7191, "Aberrant Recruitment of the Nuclear Receptor Corepressor-Histone Deacetylase Complex by the Acute Myeloid Leukemia Fusion Partner ETO".

Gerbitz, A, Oncogene, (1999), vol. 18, pp. 1745-1753, "Deregulation of the Proto-Oncogene c-myc Through t(8;22) Translocation in Burkitt's Lymphoma".

Gilbert, J et al., Clinical Cancer Research (2001), vol. 7, No. 8, pp. 2292-2300, "A Phase I Dose Escalation and Bioavailability Study of Oral Sodium Phenybutyrate in Patients with Refractory Solid Tumor Malignancies".

Grisolano, JL et al., Proceedings of the National Academy of Sciences (2003), vol. 100, No. 16, pp. 9506-9511, "An Activated Receptor Tyrosine Kinase, TEL/PDGFbetaR, Cooperates with AML1/ETO to Induce Acute Myeloid Leukemia in Mice".

Harris, NL et al., Blood (1994), vol. 84, No. 5, pp. 1361-1392, "A Revised European-American Classification of Lymphold Neoplasms: A Proposal From the International Lymphoma Study Group".

Jaboin, J et al., Cancer Research (2000), vol. 62, No. 21, pp. 6108-6115, "MS-27-275, an Inhibitor of Histone Deacetylase, Has Marked in Vitro and in Vivo Antitumor Activity against Pediatric Solid Tumors".

Kurita-Ochiai, T et al., Infection and Immunity, (1998), vol. 66, No. 6, pp. 2587-2594, "Volatile Fatty Acid, Metabolic By-Product of Periodontopathic Bacteria, Induces Apoptosis in WEHI 231 and RAJI B Lymphoma Cells and Splenic B Cells".

Liu, Z et al., Journal of Cancer Research and Clinical Oncology, (1998), vol. 124, pp. 541-548, "Synergistic Effect of Epstein-Barr Virus and Tumor Promoters on Induction of Lymphoma and Carcinoma in Nude Mice".

Madisen, L et a., Molecular and Cellular Biology, (1998), vol. 18, No. 11, pp. 6281-6292, "The Immunoglobulin Heavy Chain Locus Control Region Increases Histone Acetylation along Linked c-myc Genes".

Niitsu, N et al., Molecular Pharmacology, (2000), vol. 58, pp. 27-36, "Anticancer Derivative of Butyric Acid (Pivalyloxymethyl Butyrate) Specifically Potentiates the Cytotoxicity of Doxorubicin Through the Suppression of Microsomal Glycosidic Activity".

Orr, D et al., 2000 ASCO Annual Meeting, Abstract No. 763, "Phase I Pharmacokinetic (PK) Study of CI-994 in Combination with Gemcitabine (GEM) in Patients with Advances Solid Tumors".

Polack, A et al., The EMBO Journal, (1993), vol. 12, No. 10, pp. 3913-3920, "Regulatory Elements in the Immunoglobulin Kappa Locus Induce c-myc Activation and the Promoker Shift in Burkitt's Lymphoma Cells".

Rezuke, WN et al., Clinical Chemistry (1997), vol. 43, No. 10, pp. 1814-1823, "Molecular Diagnosis of B- abd T- cell Lymphomas: Fundamental Principles and Clinical Applications".

Rottleb, C et al., International Journal of Cancer, (1995), vol. 62, pp. 697-702, "Among 17 Inducers of Differentiation Only Sodium Butyrate Causes a Permanent Down-Regulation of c-myc in Burkitt's Lymphoma".

Rottleb, C et al., International Journal of Cancer, (1996), vol. 67, pp. 724-729, "Structure-Activity Relationship of 17 Structural Analogues of N-Butyric Acid Upon .c-myc Expression".

Rubio, MA et al., Blood, (1995), vol. 86, No. 10, pp. 3715-3724, "Granulocyte-Macrophase Colony-Stimulating Factor, Photbol Ester, and Sodium Butyrate Induce the CD11c Integrin Gene Promoter Activity During Myeloid Cell Differentiation".

Schrump, DS et al., Clinical Lung Cancer (2000), vol. 4, No. 3, pp. 186-192, "Phase I Study of Sequential Deoxyazacytidine/ depsipeptide Infusion in Patients with Malignancies Involving Lungs of Pleura".

Vrana JA et al., Oncogene 1999), vol. 18, pp. 7016-7025, "Induction of Apoptosis in U937 Human Leukemia Cells by Suberoylanilide Hydroxamic Acid (SAHA) Proceeds Through Pathways That are Regulated by Bci-2/Bcl-XL, c-Jun, and p21CIP1, but independent of p53".

Waheed et al. (2000), Proceedings of the American Association for Cancer Research Meeting, (91st, San Francisco, 41:808, Abstract 5135, "The Histone Deacetylase Inhibitor FR 901228 Induces SV40T/T Antigen Expression and P53 Hyperacetylation in Human Mesothelioma Cells".

Watanabe, M et al., Cancer Research (1990), vol. 50, pp. 3245-3248, "Effect of liposomes containing sodium butyrate conjugated with anti-CD19 monoclonal antibody on in vitro and in vivo growth of malignant lymphoma".

Weiser et al. (2001), J. Immunotherapy, 24: 151-61, "Sequencial 5-Aza-2'deoxyctidine-Depsipeptide FR901228 Treatment Induces Apoptosis Preferentially in Cancer Cells and Facilitates Their Recognition by Cytolytic T Lymphocytes Specific for NY-ESO-1".

Yu, C et al., Cancer Research (2001), vol. 63, pp. 2118-2126, "Histone Deacetylase Inhibitors Promote ST1571-Mediated Apoposis in ST1571-Sensitive and -Resistant Bcr/Abl+Human Myeloid Leukemia Cell".

Zhang, M et al., Cell Stress & Chaperones, (1998), vol. 3, No. 1, pp. 57-66, "Heat-Induces Proteolysis of HSF Causes Premature Deactivation of the Heat Shock Response in Nb2 Lymphoma Cells".

Bruner, RJ et al., Blood (2002), 44th Annual Meeting of the American Society of Hematology, vol. 100, No. 11, pp Abstract No. 1492, "Phase I trial of the histone deacetylase inhibitor depsipeptide (FR901228) in fludarabine refactory chronic lymphocytic leukemia".

Guo, F et al., American Society of Hematology, (Dec. 6-10, 2002), p. 268b, Abstract 4602 "Co-treatment with the histone deacetylase inhibitor suberoylanilide hydroxamic acid (SAHA) enhances Apo-2L/TRAIL-induced death inducing signaling complex and apoptosis of human acute lymphoid leukemia cells".

Heaney, M et al., 2003 ASCO Annual Meeting, Proceedings of the American Society of Clinical Oncology, (2003) vol. 22, p. 577, Abstract 2321, "Clinical experience with the histone deacetylase (HDAC) inhibitor suberoylanilide hydroxamic acid (SAHA) in heavily pre-treated patients with hematological malignancies".

Marcucci, G et al., Blood, (2002), 44th Annual Meeting of the American Society of Hematology, vol. 100, No. 11, pp Abstract No. 317, "Phase I trial of the histone deacetylase inhibitor depsipeptide (FR901228) in acute meyloid leukemia (AML)".

Nimmanapalli, R et al., American Society of Hematology, (Dec. 6-10, 2002), 14 pages, "Co-treatment with histone deacetylase inhibitor suberoylanilide hydroxamic acid (SAHA) enhances Gleevee-induced apoptosis of Ber-Abl positive human acute leukemia cells".

Nimmanapalli, R et al., Blood (2003), vol. 101, No. 8, pp 3236-3239, "Cotreatment with the histone deacetylase inhibitor suberoylanilide hydroxamic acid (SAHA) enhances imatinib-induced apoptosis of Bcr-Abl-positive human acute leukemia cells".

Tabe, Y et al., Blood (2002), 44th Annual Meeting of the American Society of Hematology, vol. 100, No. 11, pp Abstract No. 3028, "Effects of histone deacetylase inhibitor suberoylanikide hydroxamic acid (SAHA) and DNA methylation inhibitor 5-aza-2'-deoxycytidine (DAC) on the transcriptional activation of RARbeta and p21WAF in acute promyelocytic leukemia cells".

Zhang, C et al, The Journal of Investigative Dermatology (2003), vol. 121, No. 1, pp Abstract 1189, "The histone inhibitor suberoylanilide hydroxamic acid induces apoptosis in cutaneous T cells lymphoma cells".

O'Conner et al. (2001). Journal of the American Society of Hematology 611a, Abstract No. 2562.

Kelly, et al. (2003). Clinical Cancer Research 9:3578-3588.

Adams and Elliott (2000). Oncogene 19: 6687-6692.

Bates et al. (1999). Proc. American Society of Clinical Oncology 18: 180a, Abstract No. 693.

Foster et al. (1997). Invest. New Drugs 15: 187-194.

Gojo et al. (2002). Blood 100: Abstract No. 2198.

Gore and Carducci (2000). Exp. Opin. Invest. Drugs 9:2923-2934.

Huang and Pardee (2000). Molecular Medicine 6: 849-866.

Johnstone, R. (2000). Nature Reviews Drug Discovery 1: 287-299.

Kelly et al. (2002). Exp. Opin. Invest. Drugs 11: 1695-1713.

Kelly et al. (2002). Proc. American Society of Clinical Onocology 21: 6b, Abstract No. 1831.

Kelly et al. (2001). Proc. American Society of Clinical Onocology 20: 87a, Abstract No. 344.

Kosugi et al. (2001). Jpn. J. Cancer Res. 92: 529-536.

Marshall et al. (2002). J. Exp. Therapeutics and Oncology 2: 325-332.

Piekarz et al. (2001). Blood 98: 2865-2868.

Prakash et al. (2001). Invest. New Drugs 19: 1-11.

Rha et al. (1993). J. Korean Med. Sci. 8:251-256.

Rifkind et al. (2002). 224th ACS National Meeting, Boston, MA, Abstract No. 226.

Sandor et al. (2002). Clinical Cancer Research 8: 718-728.

Secrist et al. (2003). Curr. Opin. Invest. Drugs 4:1422-1427.

Summerhayes, M. (2001). J. Oncol. Pharm. Prac. 7: 107-125.

Vigushin, D. (2002). Current Opin. Invest. Drugs 3: 1396-1402.

Warrell et al. (1998). J. Natl. Cancer Insititute 90: 1621-1625.

International Search Report for PCT/US03/06451, mailed Oct. 27, 2003.

International Preliminary Examination Report for PCT/US03/06451, mailed Aug. 3, 2004.

International Search Report for PCT/US2004/27943, mailed Mar. 7, 2005.

Wu et al. (2001). "Negative Regulation of bcl-2 Expression by p53 in Hematopoietic Cells." Oncogene 20(2): 240-251, Abstract, Database CAPLUS on STN, Acc. No. DN134:293668.

May 17, 2007 Office Action in U.S. Appl. No. 10/413,422.

Nov. 26, 2007 Office Action in U.S. Appl. No. 11/282,420.

Ryan et al. (2003); "A Phase I Trial of an Oral Histone Deacetylase Inhibitor, MS-275, in Advanced Solid Tumor and Lymphoma Patients"; Proc. Am. Soc. Clin. Oncol. 22; 2003 ASCO Annual Meeting, Abstract No. 802.

Andrews et al. (2000). Intl. J. Parasitol. 30: 761-768.

Archer et al. (1998). Proc. Natl. Acad. Sci. USA 95: 6791-6796.

Bhalla et al. (2002). "Co-treatment With The Histone Deacetylase Inhibitor Suberoylanilide Hydroxamic Acid (SAHA) Enhances the Cytotoxic Effects of Gleevec and Arsenic Trioxide (AT) Against Bcr-Abl Positive Human Leukemia Cells." American Society of Hematology, 44th Meeting of the American Society of Hematology, Abstract 4611.

Butler et al. (2000). Cancer Res. 60: 5165-5170.

Butler et al., (2000). Clinical Cancer Res. 7: 962-970.

Butler et al. (2000). Proc. Natl. Acad. Sci. USA 99: 11700-11705.

Coffey et al. (2000). Medical and Pediatric Oncology 35:577-581.

Coffey et al. (2001). Cancer Res. 61: 3591-3594.

Cohen et al. (1999). Anticancer Res. 19: 4999-5006.

Cohen et al. (2000). Anticancer Res. 22: 1497-1504.

Curtin (2002). Exp. Opin. Ther. Patents 12: 1375-1384.

Dressel (2000). Anticancer Res. 20: 1017-1022.

Fei et al. (2002). "Co treatment With the Histone Deacetylase Inhibitor Suberoylanilide Hydroxamic Acid (SAHA) Enhances Apo-2L/TRAIL-induced Death Inducing Signaling Complex and Apoptosis of Human Acute Lymphoid Leukemia Cells." American Society of Hematology, 44th Meeting of the American Society of Hematology Abstract No. 4602.

Feinman et al. (2002). "The Histone Deacetylase Inhibitor, Suberoylanilide Hydroxamic Acid, Induces Apoptosis of Multiple Myeloma Cells." *American Society of Hematology*, 44th Meeting of the American Society of Hematology, Abstract No. 3195.
Finnin et al. (1999). *Nature* 401: 188-193.
Furamai et al. (2001). *Proc. Natl. Sci.* USA 98: 87-92.
Grunstein (1997). *Nature* 389: 349-352.
He et al. (2001). *J. Clin. Investigation* 108: 1321-1330.
Hockly et al. (2003). *Proc. Natl. Acad. Sci.* USA 100: 2041-2046.
Kelly et al. (2001). "Suberoylanilide Acid (SAHA), a Histone Deacetylase Inhibitor: Biologic Activity Without Toxicity." *American Society of Clincal Oncology*, Abstract No. 344.
Kelly et al. (2002). "Histone deacetylase inhibitor, suberoylanilide acid (SAHA), orally adminstered had good bioavailability and Biologic activity." *American Society of Clincal Oncology*, 38th Annual Meeting of the American Society of Clinical Oncology, Nov. 7-10, 2002, Abstract No. 1831.
Kelly et al. (2002). "A Phase I clinical trail of an oral formulation of the histone deacetylase inhibitor suberoylanilide hydroxamic acid (SAHA)." *European J. Cancer* 38(Suppl.7): 88, Abstract No. 286.
Kim et al. (1999). *Oncogene* 18: 2461-2470.
Kohge et al. (1998). *Biochem. Pharmacol.* 56: 1359-1364.
Komatsu et al. (2001). *Cancer Res.* 61: 4459-4466.
Kouraklis and Theocharis (2000). *Curr. Med. Chem.Anti-Cancer Agents* 2: 477-484.
Lee et al. (2001). *Cancer Res.* 61: 931-934.
Lin et al. (1998). *Nature* 391: 811-814.
Mai et al. (2001). *OPPI Briefs* 33: 391-394.
Marks et al. (2000). *J. of the Natl. Cancer Institute* 92: 1210-1215.
Marks et al. (2001). *Clinical Cancer Res.* 7: 759-760.
Marks et al. (2001). *Curr. Opin. In Oncology* 13: 477-483.
Marks et al. (2001). *Nature Reviews* 1: 194-202.
Miller et al. (2003). *J Med Chem.* 46: 5097-5116.
Munster et al. (2001). *Cancer Res.* 61: 8492-8497.
O'Connor et al. (2002). "Clinical experience of the histone deacetylase inhibitor suberoylanalide hydroxamic acid (SAHA) in heavily pre-treated patients with aggressive non-hodgkin's lymphoma (NHL0 and hodgkin's disease (HD))." *American Society of Clincal Oncology*, Dec. 6-10, 2002, Abstract No. 4742.
Qui et al. (2000). *Mol. Biol. Cell* 11: 2069-2083.
Richon et al. (1996). *Proc. Natl. Acad. Sci.* USA 93: 5705-5708.
Richon et al. (1998). *Proc. Natl. Acad. Sci.* USA 95: 3003-3007.
Richon et al. (2000). *Proc. Natl. Acad. Sci.* USA 97: 10014-10019.
Richon and O'Brien (2002). *Clinical Cancer Res.* 8: 662-664.
Saito et al. (1999). *Proc. Natl. Acad. Sci.* USA 96: 4592-4597.
Sgouros et al. (2002). "Synergistic Interaction of Suberoylanilide Hydroxamic Acid (SAHA) and Radiation in Human Prostate Tumor Spheroids." *American Society of Clinical Oncology*, Abstract No. 105.
Stowell et al. (1995). *J. Med. Chem.* 38: 1411-1413.
Su et al. (2000). *Cancer Res.* 60: 3137-3142.
Suzuki et al. (1999). *J. Med. Chem.* 42: 3001-3003.
Van Lint et al. (1996). *Gene Expression* 5: 245-253.
Vrana et al. (1999). *Oncogene* 18: 7016-7025.
Webb et al. (1999). *J. Biol. Chem.* 274: 14280-14287.
Yoshida et al. (1990). *J. Biol. Chem.* 265: 17174-17179.
Yoshida et al. (1995). *BioEssays* 17: 423-430.
Zhou et al. (1999). *Gene* 233: 13-19.
Zhou et al. (2000). *Proc. Natl. Acad. Sci.* USA 97: 1056-1061.
Zhou et al. (2000). *Proc. Natl. Acad. Sci.* USA 97: 14329-14333.
Zhou et al. (2001). *Proc. Natl. Acad. Sci.* USA 98: 10572-10577.

\* cited by examiner

Protocol 01-021
(ORAL SAHA)
ARM A: SOLID
TUMOR PATIENTS
Cohort IIa (400 mg/dose)

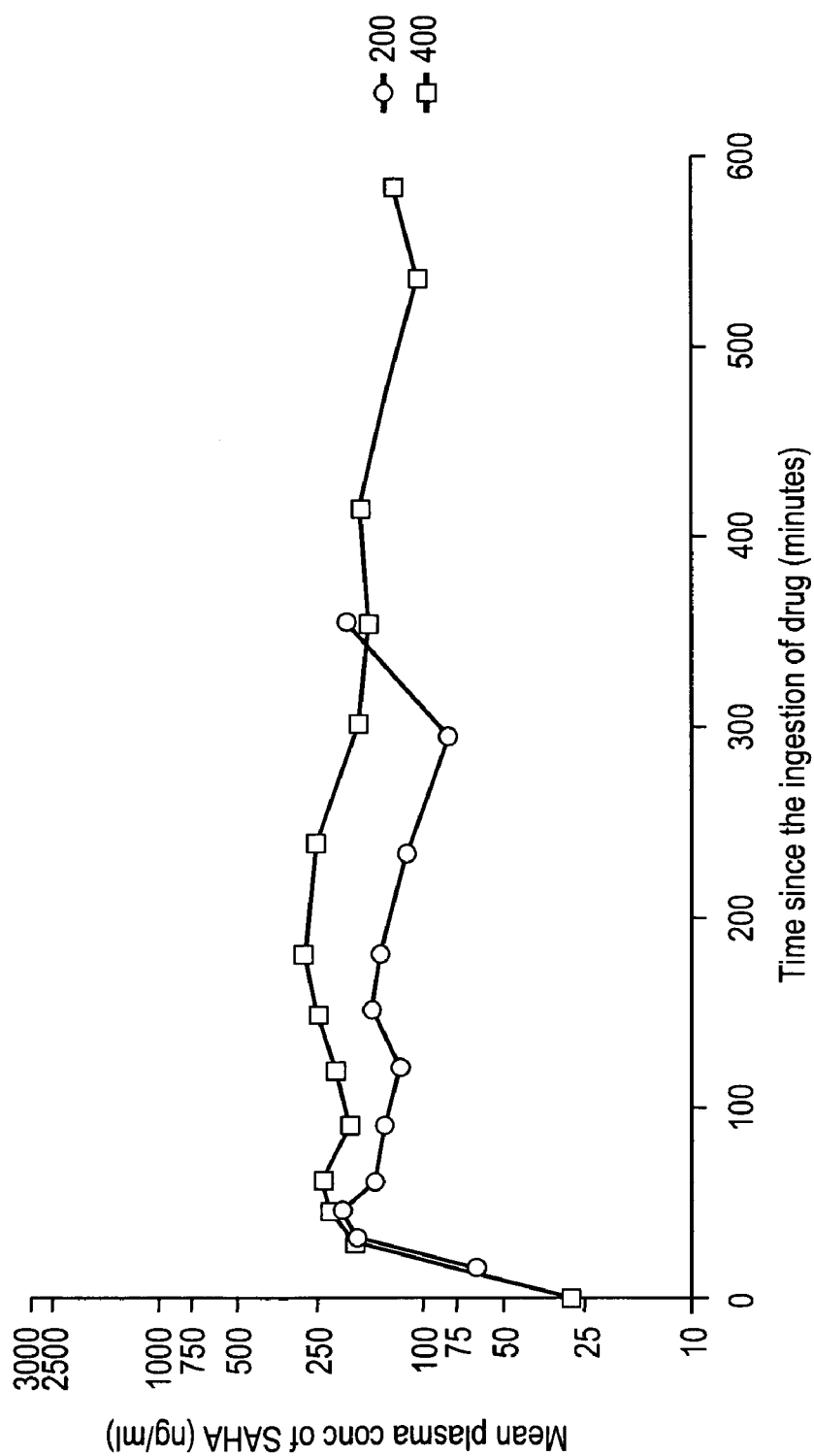

Oral 200 mg vs. 400 mg (no-fasting)
Oral Dose on Cycle 1 Day 9

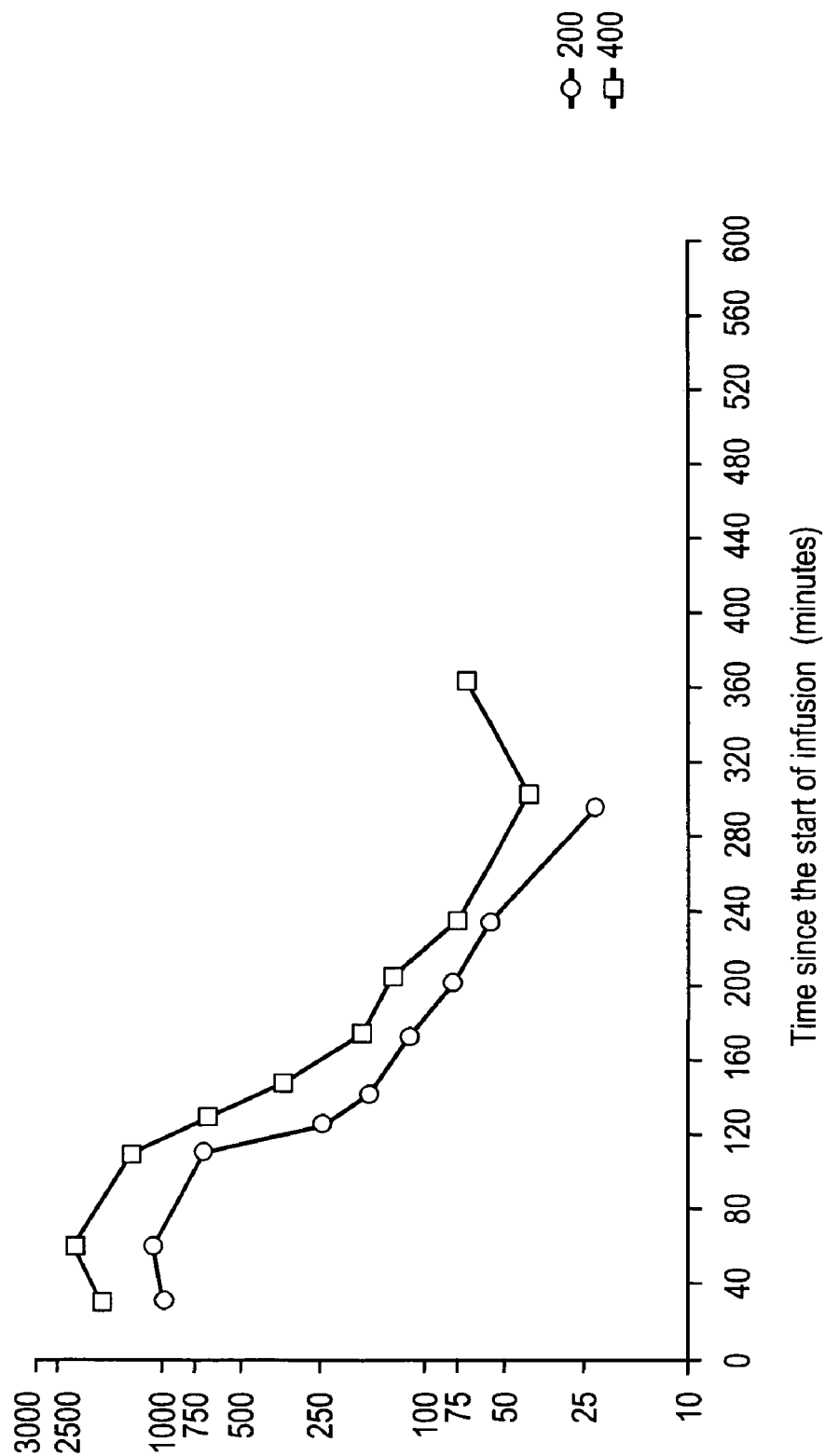

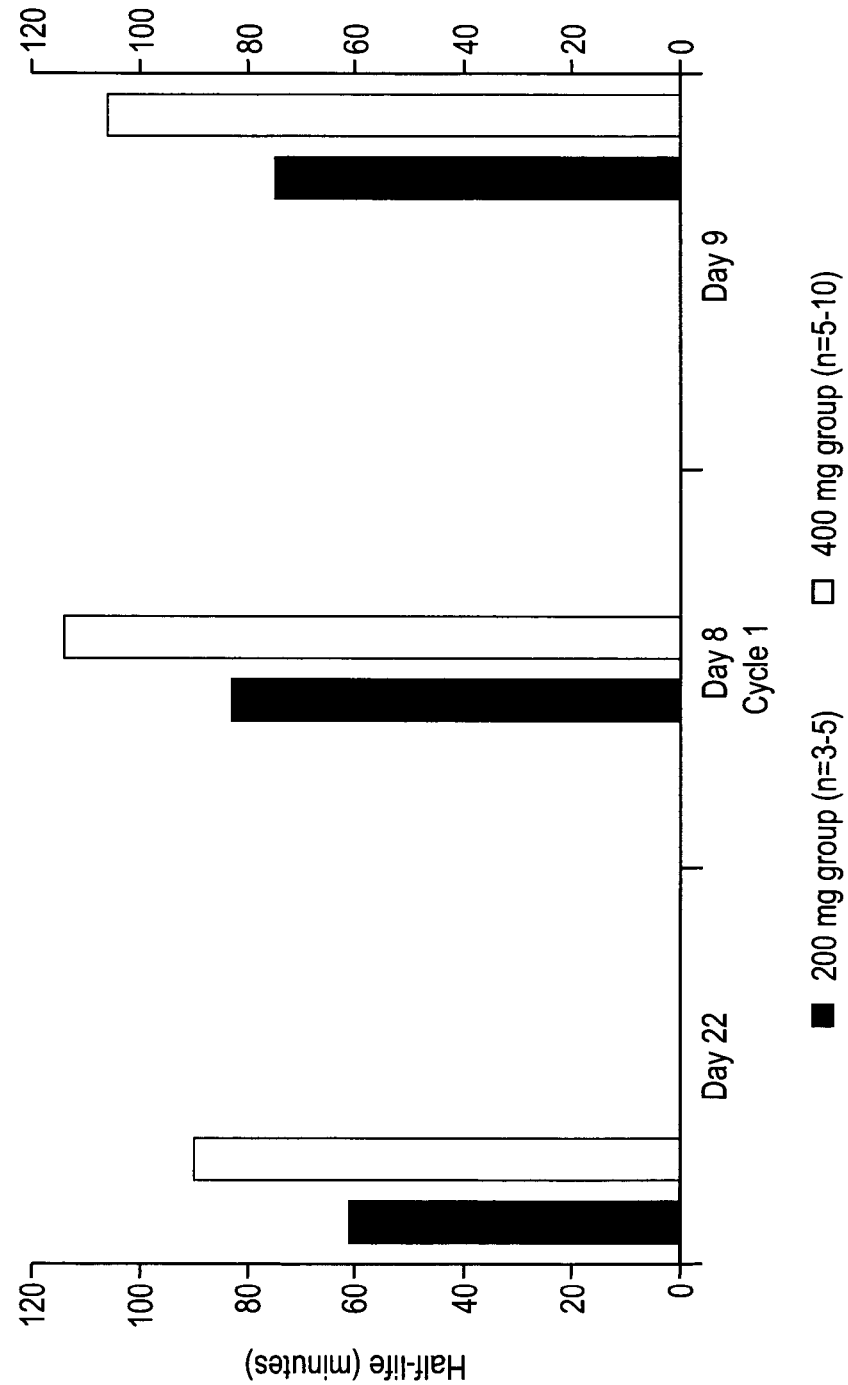

AUC of the Oral Dose AUC_last

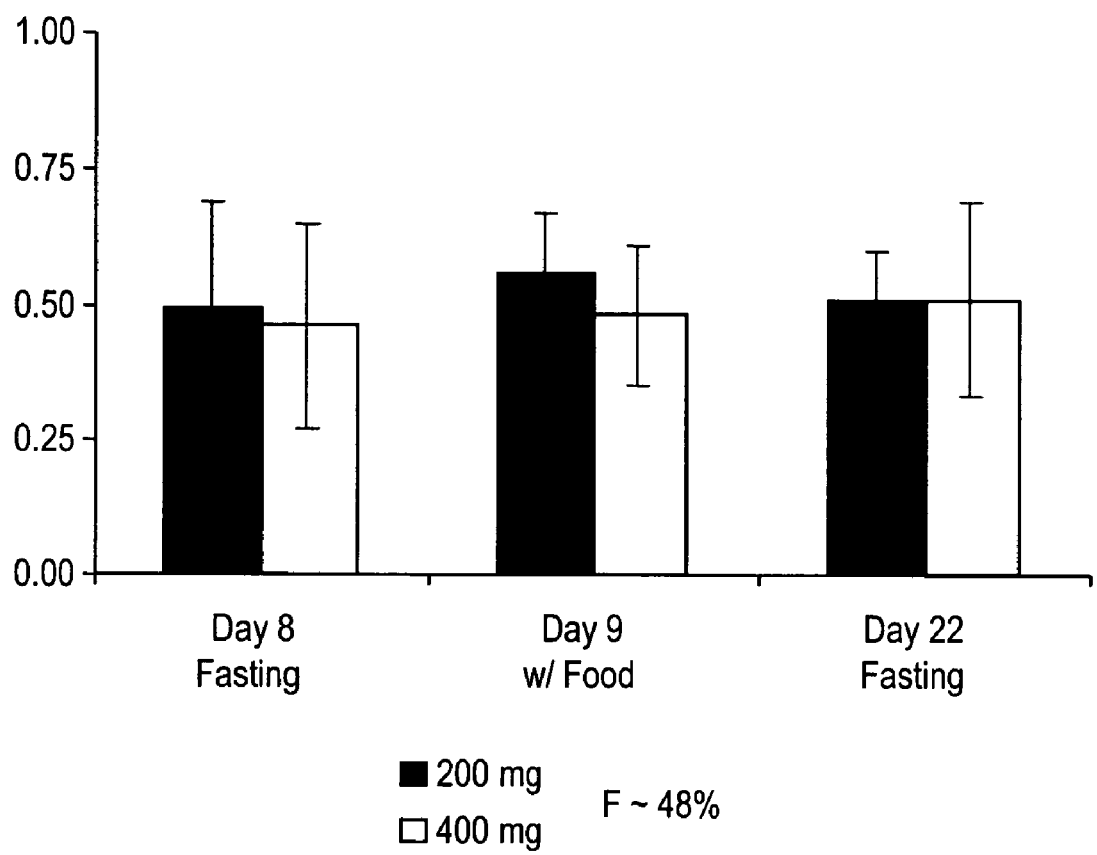

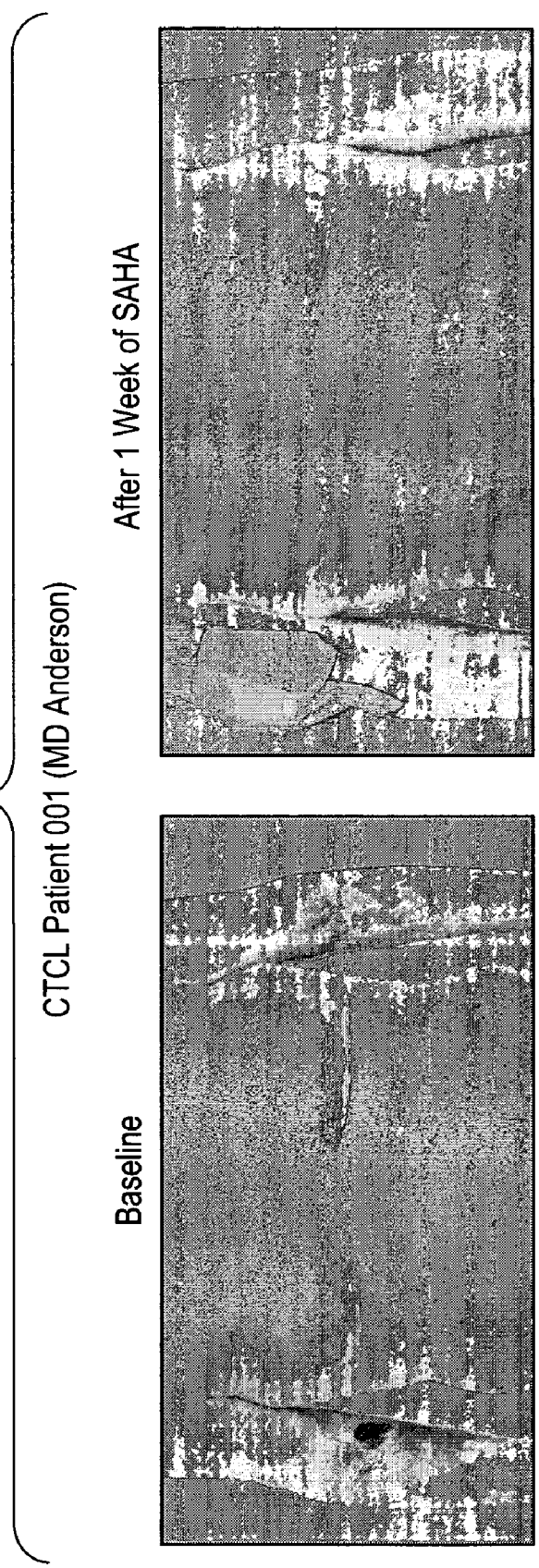

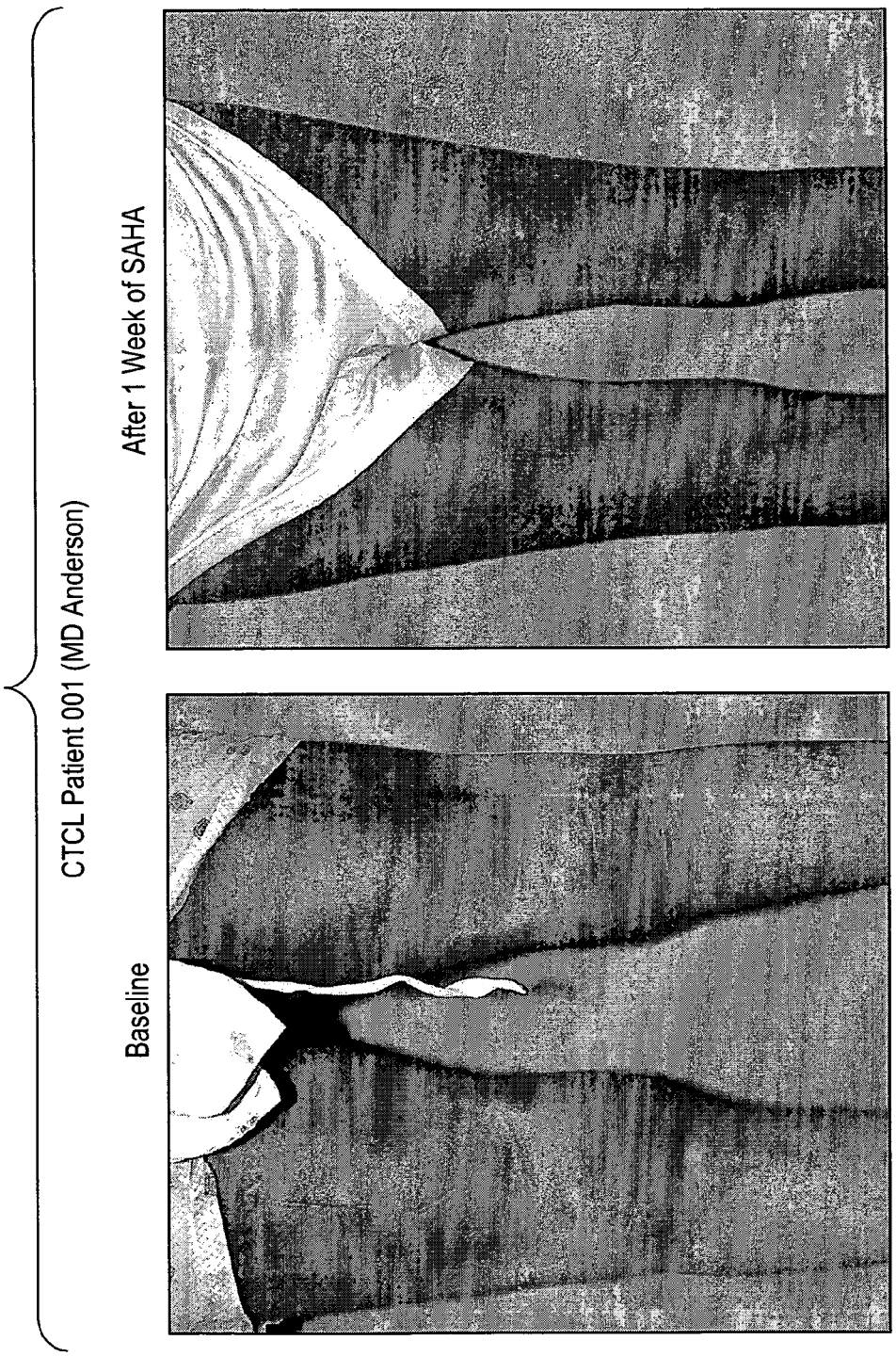

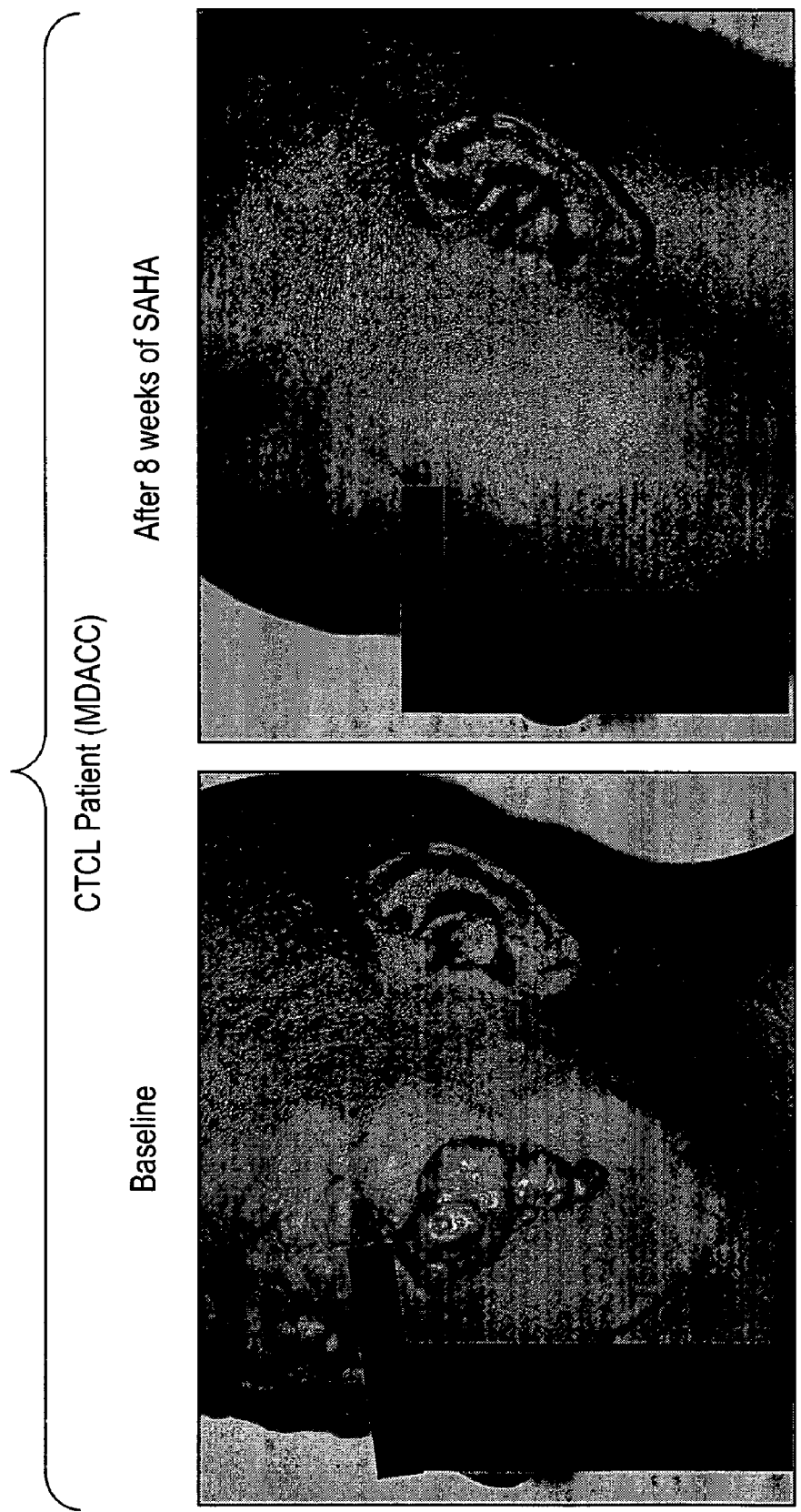

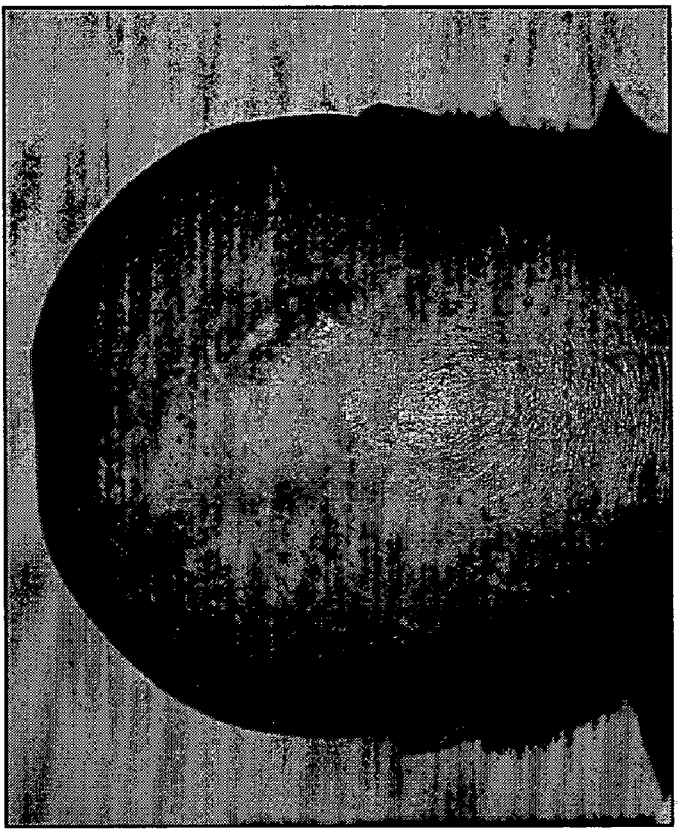
FIG. 13D
CTCL Patient 008 (MD Anderson)
Baseline
After 8 weeks of SAHA

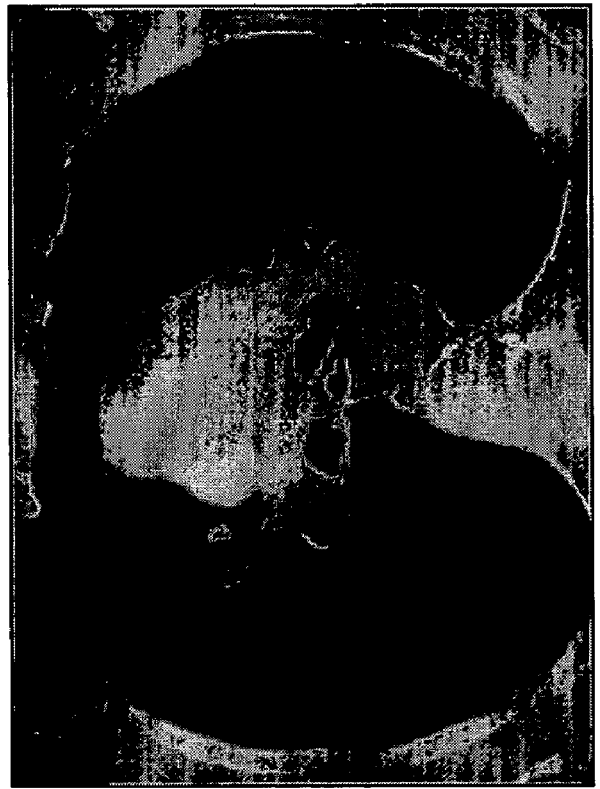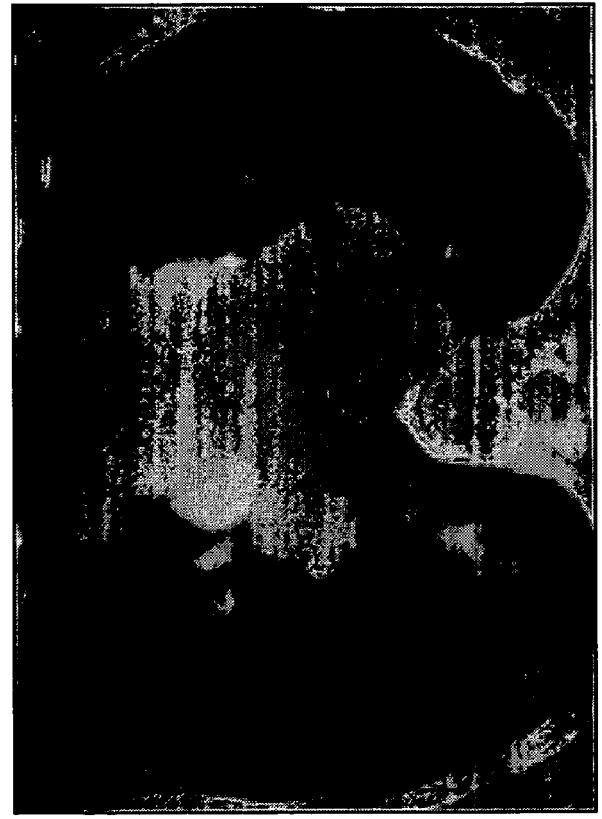
FIG. 14 Metastatic Laryngeal Cancer (MSKCC) — Pre-treatment / After 8 weeks of treatment

METHODS OF TREATING CANCER WITH HDAC INHIBITORS

GOVERNMENT INTEREST STATEMENT

This invention was made in whole or in part with government support under grant number 1R21 CA 096228-01 awarded by the National Cancer Institute. The government may have certain rights in the invention.

FIELD OF THE INVENTION

The present invention describes methods of treating cutaneous T-cell lymphomas (CTCL), peripheral T-cell lymphomas (PTCL) and head and neck cancers. The present invention provides methods of selectively inducing terminal differentiation, cell growth arrest and/or apoptosis of neoplastic cells, and/or inhibiting histone deacetylases (HDAC) administration of pharmaceutical compositions comprising HDAC inhibitors. The oral formulations of the pharmaceutical compositions have favorable pharmacokinetic profiles such as high bioavailability and surprisingly give rise to high blood levels of the active compounds over an extended period of time.

BACKGROUND OF THE INVENTION

Throughout this application various publications are referenced by arabic numerals within parentheses. Full citations for these publications may be found at the end of the specification immediately preceding the claims. The disclosures of these publications in their entireties are hereby incorporated by reference into this application in order to more fully describe the state of the art to which this invention pertains.

Cancer is a disorder in which a population of cells has become, in varying degrees, unresponsive to the control mechanisms that normally govern proliferation and differentiation. For many years there have been two principal strategies for chemotherapeutic treatment of cancer: a) blocking hormone-dependent tumor cell proliferation by interference with the production or peripheral action of sex hormones; and b) killing cancer cells directly by exposing them to cytotoxic substances, which injure both neoplastic and normal cell populations.

Cancer therapy is also being attempted by the induction of terminal differentiation of the neoplastic cells (1). In cell culture models differentiation has been reported by exposure of cells to a variety of stimuli, including: cyclic AMP and retinoic acid (2,3), aclarubicin and other anthracyclines (4).

Despite many advances in the field of oncology, the majority of solid tumors remain incurable in the advanced stages. Cytotoxic therapy is used in most cases, however, it often causes significant morbidity to the patient without significant clinical benefit. Less toxic and more specific agents to treat and control advanced malignancies are being explored.

There is abundant evidence that neoplastic transformation does not necessarily destroy the potential of cancer cells to differentiate (1,5,6). There are many examples of tumor cells which do not respond to the normal regulators of proliferation and appear to be blocked in the expression of their differentiation program, and yet can be induced to differentiate and cease replicating. A variety of agents, including some relatively simple polar compounds (5,7-9), derivatives of vitamin D and retinoic acid (10-12), steroid hormones (13), growth factors (6,14), proteases (15,16), tumor promoters (17,18), and inhibitors of DNA or RNA synthesis (4,19-24), can induce various transformed cell lines and primary human tumor explants to express more differentiated characteristics.

Early studies identified a series of polar compounds that were effective inducers of differentiation in a number of transformed cell lines (8,9). Of these, the most effective inducer was the hybrid polar/apolar compound N,N'-hexamethylene bisacetamide (HMBA) (9). The use of this polar/apolar compound to induce murine erythroleukemia cells (MELC) to undergo erythroid differentiation with suppression of oncogenicity has proved a useful model to study inducer-mediated differentiation of transformed cells (5,7-9). HMBA-induced MELC terminal erythroid differentiation is a multi-step process. Upon addition of HMBA to MELC (745A-DS19) in culture, there is a latent period of 10 to 12 hours before commitment to terminal differentiation is detected. Commitment is defined as the capacity of cells to express terminal differentiation despite removal of inducer (25). Upon continued exposure to HMBA there is progressive recruitment of cells to differentiate. The present inventors have reported that MELC cell lines made resistant to relatively low levels of vincristine become markedly more sensitive to the inducing action of HMBA and can be induced to differentiate with little or no latent period (26).

HMBA is capable of inducing phenotypic changes consistent with differentiation in a broad variety of cells lines (5). The characteristics of the drug-induced effect have been most extensively studied in the murine erythroleukemia cell system (MELC) (5,25,27,28). MELC induction of differentiation is both time and concentration dependent. The minimum concentration required to demonstrate an effect in vitro in most strains is 2 to 3 mM; the minimum duration of continuous exposure generally required to induce differentiation in a substantial portion (>20%) of the population without continuing drug exposure is about 36 hours.

The primary target of action of HMBA is not known. There is evidence that protein kinase C is involved in the pathway of inducer-mediated differentiation (29). The in vitro studies provided a basis for evaluating the potential of HMBA as a cytodifferentiation agent in the treatment of human cancers (30). Several phase I clinical trials with HMBA have been completed (31-36). Clinical trials have shown that this compound can induce a therapeutic response in patients with cancer (35,36). However, these phase I clinical trials also have demonstrated that the potential efficacy of HMBA is limited, in part, by dose-related toxicity which prevents achieving optimal blood levels and by the need for intravenous administration of large quantities of the agent, over prolonged periods.

It has been reported that a number of compounds related to HMBA with polar groups separated by apolar linkages that, on a molar basis, are as active (37) or 100 times more active than HMBA (38). As a class, however, it has been found that the symmetrical dimers such as HMBA and related compounds are not the best cytodifferentiating agents.

It has unexpectedly been found that the best compounds comprise two polar end groups separated by a flexible chain of methylene groups, wherein one or both of the polar end groups is a large hydrophobic group. Preferably, the polar end groups are different and only one is a large hydrophobic group. These compounds are unexpectedly a thousand times more active than HMBA and ten times more active than HMBA related compounds.

Histone deacetylase inhibitors such as suberoylanilide hydroxamide acid (SAHA), belong to this class of agents that have the ability to induce tumor cell growth arrest, differentiation and/or apoptosis (39). These compounds are targeted towards mechanisms inherent to the ability of a neoplastic cell to become malignant, as they do not appear to have toxicity in doses effective for inhibition of tumor growth in animals (40). There are several lines of evidence that histone acetylation and deacetylation are mechanisms by which transcriptional regulation in a cell is achieved (41). These effects are thought to occur through changes in the structure of chromatin by altering the affinity of histone proteins for coiled DNA in the nucleosome. There are five types of histones that have been identified in nucleosomes (designated H1, H2A, H2B, H3 and H4). Each nucleosome contains two of each histone type within its core, except for H1, which is present singly in the outer portion of the nucleosome structure. It is believed that when the histone proteins are hypoacetylated, there is a greater affinity of the histone to the DNA phosphate backbone This affinity causes DNA to be tightly bound to the histone and renders the DNA inaccessible to transcriptional regulatory elements and machinery. The regulation of acetylated states occurs through the balance of activity between two enzyme complexes, histone acetyl transferase (HAT) and histone deacetylase (HDAC). The hypoacetylated state is thought to inhibit transcription of associated DNA. This hypoacetylated state is catalyzed by large multiprotein complexes that include HDAC enzymes. In particular, HDACs have been shown to catalyze the removal of acetyl groups from the chromatin core histones.

The inhibition of HDAC by SAHA is thought occur through direct interaction with the catalytic site of the enzyme as demonstrated by X-ray crystallography studies (42). The result of HDAC inhibition is not believed to have a generalized effect on the genome, but rather, only affects a small subset of the genome (43). Evidence provided by DNA microarrays using malignant cell lines cultured with a HDAC inhibitor shows that there are a finite (1-2%) number of genes whose products are altered. For example, cells treated in culture with HDAC inhibitors show a consistent induction of the cyclin-dependent kinase inhibitor p21 (44). This protein plays an important role in cell cycle arrest. HDAC inhibitors are thought to increase the rate of transcription of p21 by propagating the hyperacetylated state of histones in the region of the p21 gene, thereby making the gene accessible to transcriptional machinery. Genes whose expression is not affected by HDAC inhibitors do not display changes in the acetylation of regional associated histones (45).

It has been shown in several instances that the disruption of HAT or HDAC activity is implicated in the development of a malignant phenotype. For instance, in acute promyelocytic leukemia, the oncoprotein produced by the fusion of PML and RAR alpha appears to suppress specific gene transcription through the recruitment of HDACs (46). In this manner, the neoplastic cell is unable to complete differentiation and leads to excess proliferation of the leukemic cell line.

Cutaneous T-cell lymphomas and peripheral T-cell lymphomas are forms of non-Hodgkin's lymphoma. Cutaneous T-cell lymphomas are a group of lymphoproliferative disorders characterized by localization of malignant T lymphocytes to the skin at presentation. CTCL frequently involves the skin, bloodstream, regional lymph nodes and spleen. Mycosis fungoides (MF), the most common and indolent form of CTCL, is characterized by patches, plaques or tumors containing epidermotropic $CD4^+CD45RO^+$ helper/memory T cells. MF may evolve into a leukemic variant, Sezary syndrome (SS), or transform to large cell lymphoma. The condition causes severe skin itching, pain and edema. Currently, CTCL is treated topically with steroids, photochemotherapy and chemotherapy, as well as radiotherapy. Peripheral T-cell lymphomas originate from mature or peripheral (not central or thymic) T-cell lymphocytes as a clonal proliferation from a single T-cell and are usually either predominantly nodal or extranodal tumors. They have T-cell lymphocyte cell-surface markers and clonal arrangements of the T-cell receptor genes. Approximately 16,000 to 20,000 people in the U.S. are affected by either CTCL or PTCL. These diseases are highly symptomatic. Patches, plaques and tumors are the clinical names of the different presentations. Patches are usually flat, possibly scaly and look like a "rash." Mycosis fungoides patches are often mistaken for eczema, psoriasis or non-specific dermatitis until a proper diagnosis of mycosis fungoides is made. Plaques are thicker, raised lesions. Tumors are raised "bumps" which may or may not ulcerate. A common characteristic is itching or pruritis, although many patients do not experience itching. It is possible to have one or all three of these phases. For most patients, existing treatments are palliative but not curative.

According to the National Cancer Institute, head and neck cancers account for three percent of all cancers in the U.S. Most head and neck cancers originate in the squamous cells lining the structures found in the head and neck, and are often referred to as squamous cell carcinomas of the head and neck (SCCHN). Some head and neck cancers originate in other types of cells, such as glandular cells. Head and neck cancers that originate in glandular cells are called adenocarcinomas. Head and neck cancers are further defined by the area in which they begin, such as the oral cavity, nasal cavity, larynx, pharynx, salivary glands and lymph nodes of the upper part of the neck. It is estimated that 38,000 people in the U.S. developed head and neck cancer 2002. Approximately 60% of patients present with locally advanced disease. Only 30% of these patients achieve long-term remission after treatment with surgery and/or radiation. For patients with recurrent and/or metastatic disease, the median survival is approximately six months.

U.S. Pat. Nos. 5,369,108, 5,932,616, 5,700,811, 6,087,367 and 6,511,990, issued to some of the present inventors, disclose compounds useful for selectively inducing terminal differentiation of neoplastic cells, which compounds have two polar end groups separated by a flexible chain of methylene groups or a by a rigid phenyl group, wherein one or both of the polar end groups is a large hydrophobic group. Some of the compounds have an additional large hydrophobic group at the same end of the molecule as the first hydrophobic group which further increases differentiation activity about 100 fold in an enzymatic assay and about 50 fold in a cell differentiation assay. Methods of synthesizing the compounds used in the methods and pharmaceutical compositions of this invention are fully described the aforementioned patents, the entire contents of which are incorporated herein by reference.

The aforementioned patents do not disclose specific oral formulations of the HDAC inhibitors or specific dosages and dosing schedules of the recited compounds. Importantly, the aforementioned patents do not disclose oral formulations that have favorable pharmacokinetic profiles such as high bioavailability which gives rise to high blood levels of the active compounds over an extended period of time.

The class of compounds of the present invention may be useful for selectively inducing terminal differentiation, cell growth arrest and/or apoptosis of neoplastic cells and therefore aid in treatment of tumors in patients. Thus there is an urgent need to discover suitable dosages and dosing schedules of these compounds, and to develop formulations, preferably oral formulations, which give rise to steady, therapeutically effective blood levels of the active compounds over an extended period of time.

SUMMARY OF THE INVENTION

The present invention provides a method of treating cutaneous T-cell lymphomas (CTCL), peripheral T-cell lymphomas (PTCL) or head and neck cancers by administering an effective amount of an HDAC inhibitor, such as suberoylanilide hydroxamic acid (SAHA). SAHA can be administered in a total daily dose of up to 800 mg, preferably orally, once, twice or three times daily, continuously (every day) or intermittently (e.g., 3-5 days a week).

Oral SAHA has been safely administered in phase I and phase II clinical studies to patients suffering from in cutaneous T-cell lymphomas, peripheral T-cell lymphomas or head and neck cancers.

Furthermore, the present invention provides a method of treating cutaneous T-cell lymphomas, peripheral T-cell lymphomas or head and neck cancers by administering an effective amount of an HDAC inhibitor as described herein. The HDAC inhibitors can be administered in a total daily dose of up to 800 mg, preferably orally, once, twice or three times daily, continuously (i.e., every day) or intermittently (e.g., 3-5 days a week).

The present invention also provides methods for selectively inducing terminal differentiation, cell growth arrest and/or apoptosis of neoplastic cells, thereby inhibiting proliferation of such cells, as well as methods of treating cancer and of chemoprevention in subjects in need thereof, by administering to said subject an effective amount of a pharmaceutical composition comprising a HDAC inhibitor or a pharmaceutically acceptable salt or hydrate thereof, and a pharmaceutically acceptable carrier or diluent. An effective amount of an HDAC inhibitor in the present invention can be up to a total daily dose of 800 mg.

The present invention further provides a safe, daily dosing regimen of the formulation of pharmaceutical compositions comprising an HDAC inhibitor which are easy to follow and to adhere to. These pharmaceutical compositions are suitable for oral administration and comprise a compound useful for treating cancer, chemoprevention, selectively inducing terminal differentiation, cell growth arrest and/or apoptosis of neoplastic cells, and/or which is a potent inhibitor of histone deacetylase (HDAC). The pharmaceutical compositions are further comprised of microcrystalline cellulose, croscarmellose sodium and magnesium stearate.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIGS. 9A-C are graphs showing the mean plasma concentration of SAHA (ng/ml) at the indicated time points following administration. FIG. 9A: Oral dose (200 mg and 400 mg) under fasting on Day 8. FIG. 9B: Oral dose with food on Day 9. FIG. 9C: IV dose on day 1.

FIG. 10 shows the apparent half-life of a SAHA 200 mg and 400 mg oral dose, on Days 8, 9 and 22.

FIG. 12 shows the bioavailability of SAHA after a 200 mg and 400 mg oral dose, on Days 8, 9 and 22.

FIGS. 13A-B show a patient with CTCL before treatment with SAHA and after one week of treatment with SAHA.

FIGS. 13C-D show a patient with CTCL before treatment with SAHA and after eight weeks of treatment with oral SAHA.

FIG. 14 is an image of a patient with metastatic laryngeal cancer before treatment with SAHA and after eight weeks of treatment with oral SAHA

DETAILED DESCRIPTION OF THE INVENTION

Figure 1:
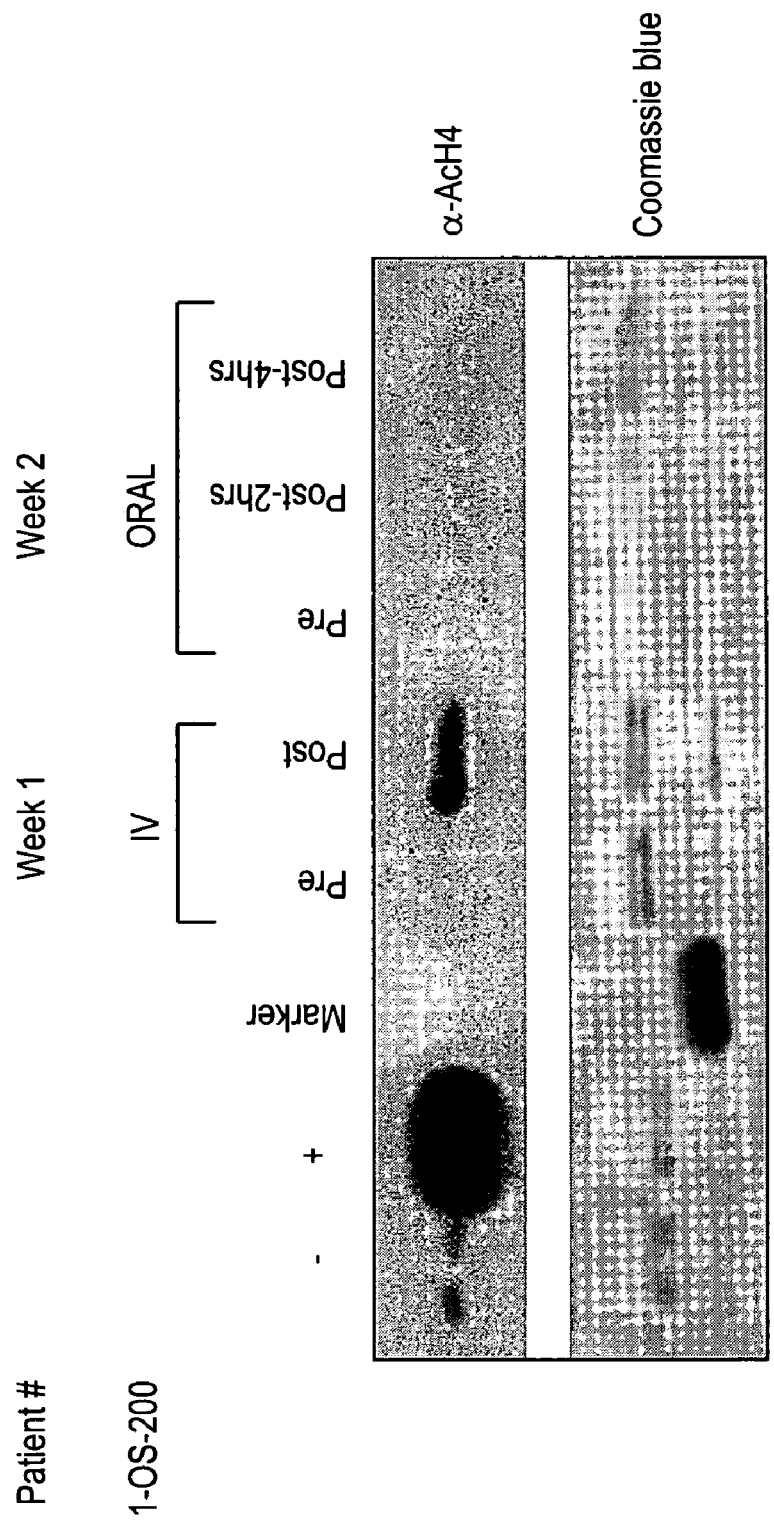
FIG. 1 is a picture of a Western blot (top panel) showing the quantities of acetylated histone-4 (α-AcH4) in the blood plasma of patients following an oral or intravenous (IV) dose of SAHA. IV SAHA was administered at 200 mg infused over two hours. Oral SAHA was administered in a single capsule at 200 mg. The amount of α-AcH4 is shown at the indicated time points. Bottom panel: Coomassie blue stain.

The present invention is a method of treating CTCL, PTCL and head and neck cancers such as SCCHN, or other cancers by administering an HDAC inhibitor, such as SAHA, which is represented by the structure described herein as formula 4, pyroxamide, which is represented by the structure described herein as formula 6, or other hydroxamic acids represented by formulas 1-3, 5 and 7-52 described herein. The HDAC inhibitor can be administered once daily (QD), or divided into multiple daily doses such as twice daily (BID), and three times daily (TID). The HDAC inhibitor can be administered at a total daily dosage of up to 800 mg, e.g., 200 mg, 400 mg, 600 mg or 800 mg, which can be administered in one daily dose or can be divided into multiple daily doses as described above.

In addition, the administration can be continuous, i.e., every day, or intermittently. The terms "intermittent" or "intermittently" as used herein means stopping and starting at either regular or irregular intervals. For example, intermittent administration of an HDAC inhibitor may be administration one to six days per week or it may mean daily administration for two consecutive weeks, then no administration for one week or it may mean administration on alternate days.

SAHA or any of the HDAC inhibitors are administered to the patient at a total daily dosage of between 25-4000 mg/m$^2$. A currently preferred treatment protocol comprises continuous administration (i.e., every day), once, twice or three times daily at a total daily dose in the range of about 200 mg to about 600 mg.

Another currently preferred treatment protocol comprises intermittent administration of between three to five days a week, once, twice or three times daily at a total daily dose in the range of about 200 mg to about 600 mg.

In one particular embodiment, the HDAC inhibitor is administered continuously once daily at a dose of 400 mg or twice daily at a dose of 200 mg.

In another particular embodiment, the HDAC inhibitor is administered intermittently three days a week, once daily at a dose of 400 mg or twice daily at a dose of 200 mg.

In another particular embodiment, the HDAC inhibitor is administered intermittently four days a week, once daily at a dose of 400 mg or twice daily at a dose of 200 mg.

In another particular embodiment, the HDAC inhibitor is administered intermittently five days a week, once daily at a dose of 400 mg or twice daily at a dose of 200 mg.

In one particular embodiment, the HDAC inhibitor is administered continuously once daily at a dose of 600 mg, twice daily at a dose of 300 mg, or three times daily at a dose of 200 mg.

In another particular embodiment, the HDAC inhibitor is administered intermittently three days a week, once daily at a dose of 600 mg, twice daily at a dose of 300 mg, or three times daily at a dose of 200 mg.

In another particular embodiment, the HDAC inhibitor is administered intermittently four days a week, once daily at a dose of 600 mg, twice daily at a dose of 300 mg, or three times daily at a dose of 200 mg.

In another particular embodiment, the HDAC inhibitor is administered intermittently five days a week, once daily at a dose of 600 mg, twice daily at a dose of 300 mg, or three times daily at a dose of 200 mg.

In addition, the HDAC inhibitor may be administered according to any of the schedules described above, consecutively for a few weeks, followed by a rest period. For example, the HDAC inhibitor may be administered according to any one of the schedules described above from two to eight weeks, followed by a rest period of one week, or twice daily at a dose of 300 mg for three to five days a week. In another particular embodiment, the HDAC inhibitor is administered three times daily for two consecutive weeks, followed by one week of rest.

It should be apparent to a person skilled in the art that the various dosages and dosing schedules described herein merely set forth specific embodiments and should not be construed as limiting the broad scope of the invention. Any permutations, variations and combinations of the dosages and dosing schedules are included within the scope of the present invention.

The compositions of the present invention may be formulated in any unit dosage form (liquid or solid) suited for oral administration, for example, in the form of a pellet, a tablet, a coated tablet, a capsule, a gelatin capsule, a solution, a suspension, or a dispersion. In a preferred embodiment, the composition is in the form of a gelatin capsule.

Any inert excipient that is commonly used as a carrier or diluent may be used in the formulations of the present invention, such as for example, a gum, a starch, a sugar, a cellulosic material, an acrylate, or mixtures thereof. A preferred diluent is microcrystalline cellulose. The compositions may further comprise a disintegrating agent (e.g., sodium croscarmellose) and a lubricant (e.g., magnesium stearate), and in addition may comprise one or more additives selected from a binder, a buffer, a protease inhibitor, a surfactant, a solubilizing agent, a plasticizer, an emulsifier, a stabilizing agent, a viscosity increasing agent, a sweetener, a film forming agent, or any combination thereof. Furthermore, the compositions of the present invention may be in the form of controlled release or immediate release formulations.

The present invention further provides a safe, daily dosing regimen of these formulations, which is easy to follow and to adhere to. The formulations of the present invention are useful for selectively inducing terminal differentiation, cell growth arrest and/or apoptosis of neoplastic cells and therefore aid in treatment of tumors in patients.

The term "treating" in its various grammatical forms in relation to the present invention refers to preventing, (i.e., chemoprevention ), curing, reversing, attenuating, alleviating, minimizing, suppressing or halting the deleterious effects of a disease state, disease progression, disease causative agent (e.g., bacteria or viruses) or other abnormal condition. For example, treatment may involve alleviating a symptom (i.e., not necessary all symptoms) of a disease or attenuating the progression of a disease. Because some of the inventive methods involve the physical removal of the etiological agent, the artisan will recognize that they are equally effective in situations where the inventive compound is administered prior to, or simultaneous with, exposure to the etiological agent (prophylactic treatment) and situations where the inventive compounds are administered after (even well after) exposure to the etiological agent.

Although the methods of the present invention can be practiced in vitro, it is contemplated that the preferred embodiment for the methods of selectively inducing terminal differentiation, cell growth arrest and/or apoptosis of neoplastic cells will comprise contacting the cells in vivo, i.e., by administering the compounds to a subject harboring neoplastic cells or tumor cells in need of treatment.

The methods of the present invention may also comprise initially administering to the subject an antitumor agent so as to render the neoplastic cells in the subject resistant to an antitumor agent and subsequently administering an effective amount of any of the compositions of the present invention, effective to selectively induce terminal differentiation, cell growth arrest and/or apoptosis of such cells, or to treat cancer or provide chemoprevention.

The antitumor agent may be one of numerous chemotherapy agents such as an alkylating agent, an antimetabolite, a hormonal agent, an antibiotic, colchicine, a vinca alkaloid, L-asparaginase, procarbazine, hydroxyurea, mitotane, nitrosoureas or an imidazole carboxamide. Suitable agents are those agents that promote depolarization of tubulin. Preferably the antitumor agent is colchicine or a vinca alkaloid; especially preferred are vinblastine and vincristine. In embodiments where the antitumor agent is vincristine, the cells preferably are treated so that they are resistant to vincristine at a concentration of about 5 mg/ml. The treating of the cells to render them resistant to an antitumor agent may be effected by contacting the cells with the agent for a period of at least 3 to 5 days. The contacting of the resulting cells with any of the compounds above is performed as described previously. In addition to the above chemotherapy agents, the compounds may also be administered together with radiation therapy.

The method of the present invention is intended for the treatment of human patients with tumors. However, it is also likely that the method would be effective in the treatment of tumors in other mammals. The term tumor is intended to include any cancer caused by the proliferation of neoplastic cells, such as T cell lymphoma, cutaneous T-cell lymphomas, peripheral T-cell lymphomas, head and neck cancers such as squamous cell carcinoma of the head and neck, lung cancer, acute lymphoid myeloma, leukemia, Hodgkin's lymphoma, non-Hodgkin's lymphoma, bladder melanoma, renal carcinoma, breast carcinoma, prostate carcinoma, ovarian carcinoma or colorectal carcinoma.

The administration of the pharmaceutical compositions can be carried out in unit dosages which may be administered orally once a day, twice a day, three times a day and the like. Currently preferred embodiments are once-daily administration, twice-daily administration, three-times daily administration, either continuously or intermittently.

Histone Deacetylases and Histone Deacetylase Inhibitors

Histone deacetylases (HDACs), as that term is used herein, are enzymes that catalyze the removal of acetyl groups from lysine residues in the amino terminal tails of the nucleosomal core histones. As such, HDACs together with histone acetyl transferases (HATs) regulate the acetylation status of histones. Histone acetylation affects gene expression and inhibitors of HDACs, such as the hydroxamic acid-based hybrid polar compound suberoylanilide hydroxamic acid (SAHA) induce growth arrest, differentiation and/or apoptosis of transformed cells in vitro and inhibit tumor growth in vivo. HDACs can be divided into three classes based on structural homology. Class I HDACs (HDACs 1, 2, 3 and 8) bear similarity to the yeast RPD3 protein, are located in the nucleus and are found in complexes associated with transcriptional co-repressors. Class II HDACs (HDACs 4, 5, 6, 7 and 9) are similar to the yeast HDA1 protein, and have both nuclear and cytoplasmic subcellular localization. Both Class I and II HDACs are inhibited by hydroxamic acid-based HDAC inhibitors, such as SAHA. Class III HDACs form a structurally distant class of NAD dependent enzymes that are related to the yeast SIR2 proteins and are not inhibited by hydroxamic acid-based HDAC inhibitors.

Histone deacetylase inhibitors or HDAC inhibitors, as that term is used herein are compounds that are capable of inhibiting the deacetylation of histones in vivo, in vitro or both. As such, HDAC inhibitors inhibit the activity of at least one histone deacetylase. As a result of inhibiting the deacetylation of at least one histone, an increase in acetylated histone occurs and accumulation of acetylated histone is a suitable biological marker for assessing the activity of HDAC inhibitors. Therefore, procedures that can assay for the accumulation of acetylated histones can be used to determine the HDAC inhibitory activity of compounds of interest. It is understood that compounds that can inhibit histone deacetylase activity can also bind to other substrates and as such can inhibit other biologically active molecules such as enzymes. It is also to be understood that the compounds of the present invention are capable of inhibiting any of the histone deacetylases set forth above, or any other histone deacetylases.

For example, in patients receiving HDAC inhibitors, the accumulation of acetylated histones in peripheral mononuclear cells as well as in tissue treated with HDAC inhibitors can be determined against a suitable control.

HDAC inhibitory activity of a particular compound can be determined in vitro using, for example, an enzymatic assays which shows inhibition of at least one histone deacetylase. Further, determination of the accumulation of acetylated histones in cells treated with a particular composition can be determinative of the HDAC inhibitory activity of a compound.

Assays for the accumulation of acetylated histones are well known in the literature. See, for example, Marks, P. A. et al., J. Natl Cancer Inst., 92:1210-1215, 2000, Butler, L. M. et al., Cancer Res. 60:5165-5170 (2000), Richon, V. M. et al., Proc. Natl. Acad. Sci., USA, 95:3003-3007, 1998, and Yoshida, M. et al., J. Biol. Chem., 265:17174-17179, 1990.

For example, an enzymatic assay to determine the activity of a histone deacetylase inhibitor compound can be conducted as follows. Briefly, the effect of an HDAC inhibitor compound on affinity purified human epitope-tagged (Flag) HDAC1 can be assayed by incubating the enzyme preparation in the absence of substrate on ice for about 20 minutes with the indicated amount of inhibitor compound. Substrate ([$^3$H] acetyl-labelled murine erythroleukemia cell-derived histone) can be added and the sample can be incubated for 20 minutes at 37° C. in a total volume of 30 µL. The reaction can then be stopped and released acetate can be extracted and the amount of radioactivity release determined by scintillation counting. An alternative assay useful for determining the activity of a histone deacetylase inhibitor compound is the "HDAC Fluorescent Activity Assay; Drug Discovery Kit-AK-500" available from BIOMOL® Research Laboratories, Inc., Plymouth Meeting, Pa.

In vivo studies can be conducted as follows. Animals, for example, mice, can be injected intraperitoneally with an HDAC inhibitor compound. Selected tissues, for example, brain, spleen, liver etc, can be isolated at predetermined times, post administration. Histones can be isolated from tissues essentially as described by Yoshida et al., J. Biol. Chem. 265:17174-17179, 1990. Equal amounts of histones (about 1 µg) can be electrophoresed on 15% SDS-polyacrylamide gels and can be transferred to Hybond-P filters (available from Amersham). Filters can be blocked with 3% milk and can be probed with a rabbit purified polyclonal anti-acetylated histone H4 antibody (αAc-H4) and anti-acetylated histone H3 antibody (αAc-H3) (Upstate Biotechnology, Inc.). Levels of acetylated histone can be visualized using a horseradish peroxidase-conjugated goat anti-rabbit antibody (1:5000) and the SuperSignal chemiluminescent substrate (Pierce). As a loading control for the histone protein, parallel gels can be run and stained with Coomassie Blue (CB).

In addition, hydroxamic acid-based HDAC inhibitors have been shown to up regulate the expression of the p21$^{WAF1}$ gene. The p21$^{WAF1}$ protein is induced within 2 hours of culture with HDAC inhibitors in a variety of transformed cells using standard methods. The induction of the p21$^{WAF1}$ gene is associated with accumulation of acetylated histones in the chromatin region of this gene. Induction of p21$^{WAF1}$ can therefore be recognized as involved in the G1 cell cycle arrest caused by HDAC inhibitors in transformed cells.

Typically, HDAC inhibitors fall into five general classes: 1) hydroxamic acid derivatives; 2) Short-Chain Fatty Acids (SC-FAs); 3) cyclic tetrapeptides; 4) benzamides; and 5) electrophilic ketones.

Thus, the present invention includes within its broad scope compositions comprising HDAC inhibitors which are 1) hydroxamic acid derivatives; 2) Short-Chain Fatty Acids (SC-FAs); 3) cyclic tetrapeptides; 4) benzamides; 5) electrophilic ketones; and/or any other class of compounds capable of inhibiting histone deacetylases, for use in inhibiting histone deacetylase, inducing terminal differentiation, cell growth arrest and/or apoptosis in neoplastic cells, and/or inducing differentiation, cell growth arrest and/or apoptosis of tumor cells in a tumor.

Non-limiting examples of such HDAC inhibitors are set forth below. It is understood that the present invention includes any salts, crystal structures, amorphous structures, hydrates, derivatives, metabolites, stereoisomers, structural isomers, polymorphs and prodrugs of the HDAC inhibitors described herein.

A. Hydroxamic Acid Derivatives such as suberoylanilide hydroxamic acid (SAHA) (Richon et al., Proc. Natl. Acad. Sci. USA 95,3003-3007 (1998)); m-carboxycinnamic acid bishydroxamide (CBHA) (Richon et al., supra); pyroxamide; trichostatin analogues such as trichostatin A (TSA) and trichostatin C (Koghe et al. 1998. Biochem. Pharmacol. 56: 1359-1364); salicylhydroxamic acid (Andrews et al., International J. Parasitology 30,761-768 (2000)); suberoyl bishydroxamic acid (SBHA) (U.S. Pat. No. 5,608,108); azelaic bishydroxamic acid (ABHA) (Andrews et al., supra); azelaic-1-hydroxamate-9-anilide (AAHA) (Qiu et al., Mol. Biol. Cell 11, 2069-2083 (2000)); 6-(3-chlorophenylureido) carpoic hydroxamic acid (3Cl-UCHA); oxamflatin [(2E)-5-[3-[(phenylsufonyl) amino]phenyl]-pent-2-en-4-ynohydroxamic acid] (Kim et al. Oncogene, 18: 2461 2470 (1999)); A-161906, Scriptaid (Su et al. 2000 Cancer Research, 60: 3137-3142); PXD-101 (Prolifix); LAQ-824; CHAP; MW2796 (Andrews et al., supra); MW2996 (Andrews et al., supra); or any of the hydroxamic acids disclosed in U.S. Pat. Nos. 5,369,108, 5,932,616, 5,700,811, 6,087,367 and 6,511,990.

B. Cyclic Tetrapeptides such as trapoxin A (TPX)-cyclic tetrapeptide (cyclo-(L-phenylalanyl-L-phenylalanyl-D-pipecolinyl-L-2-amino-8-oxo-9,10-epoxy decanoyl)) (Kijima et al., J. Biol. Chem. 268,22429-22435 (1993)); FR901228 (FK 228, depsipeptide) (Nakajima et al., Ex. Cell Res. 241,126-133 (1998)); FR225497 cyclic tetrapeptide (H. Mori et al., PCT Application WO 00/08048 (17 Feb. 2000)); apicidin cyclic tetrapeptide [cyclo(N—O-methyl-L-tryptophanyl-L-isoleucinyl-D-pipecolinyl-L-2-amino-8-oxodecanoyl)] (Darkin-Rattray et al., Proc. Natl. Acad. Sci. USA 93,1314313147 (1996)); apicidin Ia, apicidin Ib, apicidin Ic, apicidin Ia, and apicidin IIb (P. Dulski et al., PCT Application WO 97/11366); CHAP, HC-toxin cyclic tetrapeptide (Bosch et al., Plant Cell 7, 1941-1950 (1995)); WF27082 cyclic tetrapeptide (PCT Application WO 98/48825); and chlamydocin (Bosch et al., supra).

C. Short chain fatty acid (SCFA) derivatives such as: sodium butyrate (Cousens et al., J. Biol. Chem. 254,1716-1723 (1979)); isovalerate (McBain et al., Biochem. Pharm. 53: 1357-1368 (1997)); valerate (McBain et al., supra); 4-phenylbutyrate (4-PBA) (Lea and Tulsyan, Anticancer Research, 15,879-873 (1995)); phenylbutyrate (PB) (Wang et al., Cancer Research, 59, 2766-2799 (1999)); propionate (McBain et al., supra); butyramide (Lea and Tulsyan, supra); isobutyramide (Lea and Tulsyan, supra); phenylacetate (Lea and Tulsyan, supra); 3-bromopropionate (Lea and Tulsyan, supra); tributyrin (Guan et al., Cancer Research, 60,749-755 (2000)); valproic acid valproate and Pivanex™.

D. Benzamide derivatives such as CI-994; MS-27-275 [N-(2-aminophenyl)-4-[N-(pyridin-3-yl methoxycarbonyl)aminomethyl]benzamide] (Saito et al., Proc. Natl. Acad. Sci. USA 96, 4592-4597 (1999)); and 3'-amino derivative of MS-27-275 (Saito et al., supra).

E. Electrophilic ketone derivatives such as trifluoromethyl ketones (Frey et al, Bioorganic & Med. Chem. Lett. (2002), 12, 3443-3447; U.S. Pat. No. 6,511,990) and α-keto amides such as N-methyl-α-ketoamides F. Other HDAC Inhibitors such as natural products, psammaplins and depudecin (Kwon et al. 1998. PNAS 95: 3356-3361).

Preferred hydroxamic acid based HDAC inhibitors are suberoylanilide hydroxamic acid (SAHA), m-carboxycinnamic acid bishydroxamate (CBHA) and pyroxamide. SAHA has been shown to bind directly in the catalytic pocket of the histone deacetylase enzyme. SAHA induces cell cycle arrest, differentiation and/or apoptosis of transformed cells in culture and inhibits tumor growth in rodents. SAHA is effective at inducing these effects in both solid tumors and hematological cancers. It has been shown that SAHA is effective at inhibiting tumor growth in animals with no toxicity to the animal. The SAHA-induced inhibition of tumor growth is associated with an accumulation of acetylated histones in the tumor. SAHA is effective at inhibiting the development and continued growth of carcinogen-induced (N-methylnitrosourea) mammary tumors in rats. SAHA was administered to the rats in their diet over the 130 days of the study. Thus, SAHA is a nontoxic, orally active antitumor agent whose mechanism of action involves the inhibition of histone deacetylase activity.

Preferred HDAC inhibitors are those disclosed in U.S. Pat. Nos. 5,369,108, 5,932,616, 5,700,811, 6,087,367 and 6,511,990, issued to some of the present inventors disclose compounds, the entire contents of which are incorporated herein by reference, non-limiting examples of which are set forth below:

In one embodiment, the HDAC inhibitor useful in the methods of the present invention is represented by the structure of formula 1, or a pharmaceutically acceptable salt or hydrate thereof:

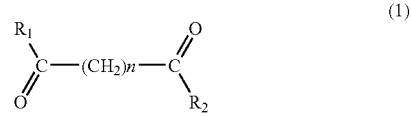

wherein $R_1$ and $R_2$ can be the same or different; when $R_1$ and $R_2$ are the same, each is a substituted or unsubstituted arylamino, cycloalkylamino, pyridineamino, piperidino, 9-purine-6-amine or thiazoleamino group; when $R_1$ and $R_2$ are different $R_1=R_3$—N—$R_4$, wherein each of $R_3$ and $R_4$ are independently the same as or different from each other and are a hydrogen atom, a hydroxyl group, a substituted or unsubstituted, branched or unbranched alkyl, alkenyl, cycloalkyl, aryl alkyloxy, aryloxy, arylalkyloxy or pyridine group, or $R_3$ and $R_4$ are bonded together to form a piperidine group, $R_2$ is a hydroxylamino, hydroxyl, amino, alkylamino, dialkylamino or alkyloxy group and n is an integer from about 4 to about 8.

In a particular embodiment of formula 1, $R_1$ and $R_2$ are the same and are a substituted or unsubstituted thiazoleamino group; and n is an integer from about 4 to about 8.

In one embodiment, the HDAC inhibitor useful in the methods of the present invention is represented by the structure of formula 2, or a pharmaceutically acceptable salt or hydrate thereof:

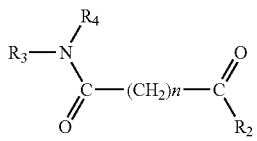

(2)

wherein each of $R_3$ and $R_4$ are independently the same as or different from each other and are a hydrogen atom, a hydroxyl group, a substituted or unsubstituted, branched or unbranched alkyl, alkenyl, cycloalkyl, arylalkyloxy, aryloxy, arylalkyloxy or pyridine group, or $R_3$ and $R_4$ are bonded together to form a piperidine group, $R_2$ is a hydroxylamino, hydroxyl, amino, alkylamino, dialkylamino or alkyloxy group and n is an integer from about 4 to about 8.

In a particular embodiment of formula 2, each of $R_3$ and $R_4$ are independently the same as or different from each other and are a hydrogen atom, a hydroxyl group, a substituted or unsubstituted, branched or unbranched alkyl, alkenyl, cycloalkyl, aryl, alkyloxy, aryloxy, arylalkyloxy, or pyridine group, or $R_3$ and $R_4$ bond together to form a piperidine group; $R_2$ is a hydroxylamino, hydroxyl, amino, alkylamino, or alkyloxy group; n is an integer from 5 to 7; and $R_3$—N—$R_4$ and $R_2$ are different.

In another particular embodiment of formula 2, n is 6. In yet another embodiment of formula 2, $R_4$ is a hydrogen atom, $R_3$ is a substituted or unsubstituted phenyl and n is 6. In yet another embodiment of formula 2, $R_4$ is a hydrogen atom, $R_3$ is a substituted phenyl and n is 6, wherein the phenyl substituent is selected from the group consisting of a methyl, cyano, nitro, trifluoromethyl, amino, aminocarbonyl, methylcyano, chloro, fluoro, bromo, iodo, 2,3-difluoro, 2,4-difluoro, 2,5-difluoro, 3,4-difluoro, 3,5-difluoro, 2,6-difluoro, 1,2,3-trifluoro, 2,3,6-trifluoro, 2,4,6-trifluoro, 3,4,5-trifluoro, 2,3,5,6-tetrafluoro, 2,3,4,5,6-pentafluoro, azido, hexyl, t-butyl, phenyl, carboxyl, hydroxyl, methoxy, phenyloxy, benzyloxy, phenylaminooxy, phenylaminocarbonyl, methoxycarbonyl, methylaminocarbonyl, dimethylamino, dimethylamino carbonyl, or hydroxylaminocarbonyl group.

In another embodiment of formula 2, n is 6, $R_4$ is a hydrogen atom and $R_3$ is a cyclohexyl group. In another embodiment of formula 2, n is 6, $R_4$ is a hydrogen atom and $R_3$ is a methoxy group. In another embodiment of formula 2, n is 6 and $R_3$ and $R_4$ bond together to form a piperidine group. In another embodiment of formula 2, n is 6, $R_4$ is a hydrogen atom and $R_3$ is a benzyloxy group. In another embodiment of formula 2, $R_4$ is a hydrogen atom and $R_3$ is a γ-pyridine group. In another embodiment of formula 2, $R_4$ is a hydrogen atom and $R_3$ is a β-pyridine group. In another embodiment of formula 2, $R_4$ is a hydrogen atom and $R_3$ is an α-pyridine group. In another embodiment of formula 2, n is 6, and $R_3$ and $R_4$ are both methyl groups. In another embodiment of formula 2, n is 6, $R_4$ is a methyl group and $R_3$ is a phenyl group.

In one embodiment, the HDAC inhibitor useful in the methods of the present invention is represented by the structure of formula 3, or a pharmaceutically acceptable salt or hydrate thereof:

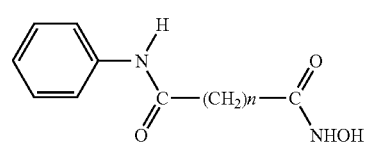

(3)

wherein n is an integer from 5 to about 8.

In a preferred embodiment of formula 3, n is 6. In accordance with this embodiment, the HDAC inhibitor is SAHA (4), or a pharmaceutically acceptable salt or hydrate thereof:

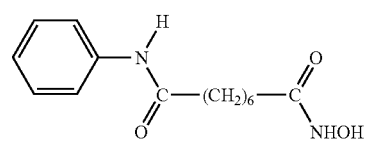

(4)

In one embodiment, the HDAC inhibitor useful in the methods of the present invention is represented by the structure of formula 5, or a pharmaceutically acceptable salt or hydrate thereof:

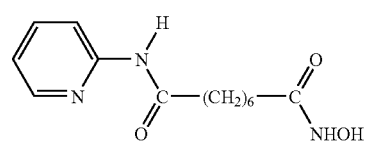

(5)

In one embodiment, the HDAC inhibitor useful in the methods of the present invention is represented by the structure of formula 6 (pyroxamide), or a pharmaceutically acceptable salt or hydrate thereof:

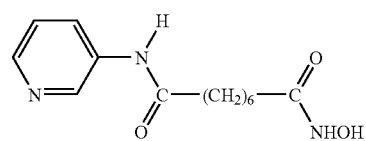

(6)

In one embodiment, the HDAC inhibitor useful in the methods of the present invention is represented by the structure of formula 7, or a pharmaceutically acceptable salt or hydrate thereof:

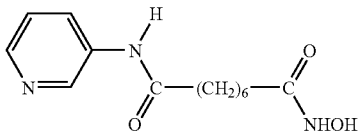
(7)

In one embodiment, the HDAC inhibitor useful in the methods of the present invention is represented by the structure of formula 8, or a pharmaceutically acceptable salt or hydrate thereof:

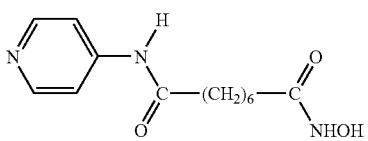
(8)

In one embodiment, the HDAC inhibitor useful in the methods of the present invention is represented by the structure of formula 9, or a pharmaceutically acceptable salt or hydrate thereof:

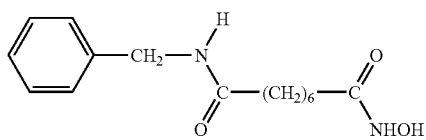
(9)

In one embodiment, the HDAC inhibitor useful in the methods of the present invention is represented by the structure of formula 10, or a pharmaceutically acceptable salt or hydrate thereof:

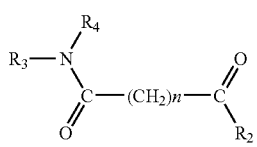
(10)

wherein $R_3$ is hydrogen and $R_4$ cycloalkyl, aryl, aryloxy, arylalkyloxy, or pyridine group, or $R_3$ and $R_4$ bond together to form a piperidine group; $R_2$ is a hydroxylamino group; and n is an integer from 5 to about 8.

In one embodiment, the HDAC inhibitor useful in the methods of the present invention is represented by the structure of formula 11, or a pharmaceutically acceptable salt or hydrate thereof:

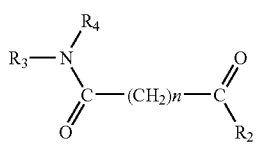
(11)

wherein $R_3$ and $R_4$ are independently a substituted or unsubstituted, branched or unbranched alkyl, alkenyl, cycloalkyl, aryl, alkyloxy, aryloxy, arylalkyloxy, or pyridine group, cycloalkyl, aryl, aryloxy, arylalkyloxy, or pyridine group, or $R_3$ and $R_4$ bond together to form a piperidine group; $R_2$ is a hydroxylamino group; and n is an integer from 5 to about 8.

In one embodiment, the HDAC inhibitor useful in the methods of the present invention is represented by the structure of formula 12, or a pharmaceutically acceptable salt or hydrate thereof:

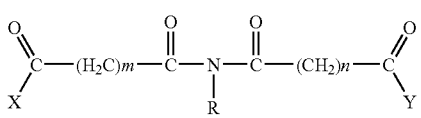
(12)

wherein each of X and Y are independently the same as or different from each other and are a hydroxyl, amino or hydroxylamino group, a substituted or unsubstituted alkyloxy, alkylamino, dialkylamino, arylamino, alkylarylamino, alkyloxyamino, aryloxyamino, alkyloxyalkylamino, or aryloxyalkylamino group; R is a hydrogen atom, a hydroxyl, group, a substituted or unsubstituted alkyl, arylalkyloxy, or aryloxy group; and each of m and n are independently the same as or different from each other and are each an integer from about 0 to about 8.

In a particular embodiment, the HDAC inhibitor is a compound of formula 12 wherein X, Y and R are each hydroxyl and both m and n are 5.

In one embodiment, the HDAC inhibitor useful in the methods of the present invention is represented by the structure of formula 13, or a pharmaceutically acceptable salt or hydrate thereof:

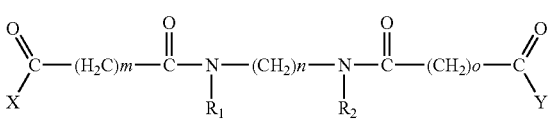
(13)

wherein each of X and Y are independently the same as or different from each other and are a hydroxyl, amino or hydroxylamino group, a substituted or unsubstituted alkyloxy, alkylamino, dialkylamino, arylamino, alkylarylamino, alkyloxyamino, aryloxyamino, alkyloxyalkylamino or aryloxyalkylamino group; each of $R_1$ and $R_2$ are independently the same as or different from each other and are a hydrogen atom, a hydroxyl group, a substituted or unsubstituted alkyl, aryl, alkyloxy, or aryloxy group; and each of m, n and o are independently the same as or different from each other and are each an integer from about 0 to about 8.

In one particular embodiment of formula 13, each of X and Y is a hydroxyl group and each of $R_1$ and $R_2$ is a methyl group. In another particular embodiment of formula 13, each of X and Y is a hydroxyl group, each of $R_1$ and $R_2$ is a methyl group, each of n and o is 6, and m is 2.

In one embodiment, the HDAC inhibitor useful in the methods of the present invention is represented by the structure of formula 14, or a pharmaceutically acceptable salt or hydrate thereof:

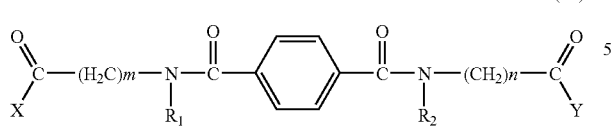

(14)

wherein each of X and Y are independently the same as or different from each other and are a hydroxyl, amino or hydroxylamino group, a substituted or unsubstituted alkyloxy, alkylamino, dialkylamino, arylamino, alkylarylamino, alkyloxyamino, aryloxyamino, alkyloxyalkylamino or aryloxyalkylamino group; each of $R_1$ and $R_2$ are independently the same as or different from each other and are a hydrogen atom, a hydroxyl group, a substituted or unsubstituted alkyl, aryl, alkyloxy, or aryloxy group; and each of m and n are independently the same as or different from each other and are each an integer from about 0 to about 8.

In one embodiment, the HDAC inhibitor useful in the methods of the present invention is represented by the structure of formula 15, or a pharmaceutically acceptable salt or hydrate thereof:

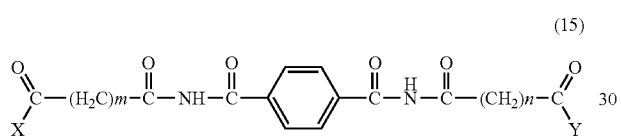

(15)

wherein each of X and Y are independently the same as or different from each other and are a hydroxyl, amino or hydroxylamino group, a substituted or unsubstituted alkyloxy, alkylamino, dialkylamino, arylamino, alkylarylamino, alkyloxyamino, aryloxyamino, alkyloxyalkylamino or aryloxyalkylamino group; and each of m and n are independently the same as or different from each other and are each an integer from about 0 to about 8.

In one particular embodiment of formula 15, each of X and Y is a hydroxyl group and each of m and n is 5.

In one embodiment, the HDAC inhibitor useful in the methods of the present invention is represented by the structure of formula 16, or a pharmaceutically acceptable salt or hydrate thereof:

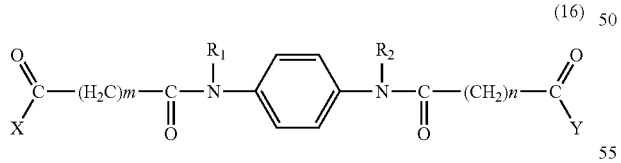

(16)

wherein each of X and Y are independently the same as or different from each other and are a hydroxyl, amino or hydroxylamino group, a substituted or unsubstituted alkyloxy, alkylamino, dialkylamino, arylamino, alkylarylamino, alkyloxyamino, aryloxyamino, alkyloxyalkylamino or aryloxyalkylamino group; $R_1$ and $R_2$ are independently the same as or different from each other and are a hydrogen atom, a hydroxyl group, a substituted or unsubstituted alkyl, arylalkyloxy or aryloxy group; and each of m and n are independently the same as or different from each other and are each an integer from about 0 to about 8.

In one embodiment, the HDAC inhibitor useful in the methods of the present invention is represented by the structure of formula 17, or a pharmaceutically acceptable salt or hydrate thereof:

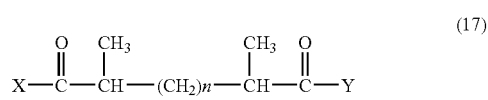

(17)

wherein each of X an Y are independently the same as or different from each other and are a hydroxyl, amino or hydroxylamino group, a substituted or unsubstituted alkyloxy, alkylamino, dialkylamino, arylamino, alkylarylamino, or aryloxyalkylamino group; and n is an integer from about 0 to about 8.

In one particular embodiment of formula 17, each of X and Y is a hydroxylamino group; $R_1$ is a methyl group, $R_2$ is a hydrogen atom; and each of m and n is 2. In another particular embodiment of formula 17, each of X and Y is a hydroxylamino group; $R_1$ is a carbonylhydroxylamino group, $R_2$ is a hydrogen atom; and each of m and n is 5. In another particular embodiment of formula 17, each of X and Y is a hydroxylamino group; each of $R_1$ and $R_2$ is a fluoro group; and each of m and n is 2.

In one embodiment, the HDAC inhibitor useful in the methods of the present invention is represented by the structure of formula 18, or a pharmaceutically acceptable salt or hydrate thereof:

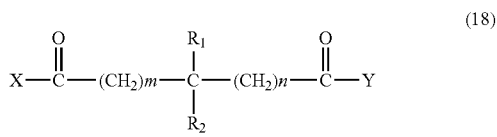

(18)

wherein each of X and Y are independently the same as or different from each other and are a hydroxyl, amino or hydroxylamino group, a substituted or unsubstituted alkyloxy, alkylamino, dialkylamino, arylamino, alkylarylamino, alkyloxyamino, aryloxyamino, alkyloxyalkyamino or aryloxyalkylamino group; each of $R_1$ and $R_2$ are independently the same as or different from each other and are a hydrogen atom, a hydroxyl group, a substituted or unsubstituted alkyl, aryl, alkyloxy, aryloxy, carbonylhydroxylamino or fluoro group; and each of m and n are independently the same as or different from each other and are each an integer from about 0 to about 8.

In one embodiment, the HDAC inhibitor useful in the methods of the present invention is represented by the structure of formula 19, or a pharmaceutically acceptable salt or hydrate thereof:

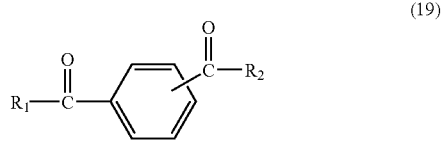

(19)

wherein each of $R_1$ and $R_2$ are independently the same as or different from each other and are a hydroxyl, alkyloxy, amino, hydroxylamino, alkylamino, dialkylamino, arylamino, alkylarylamino, alkyloxyamino, aryloxyamino, alkyloxyalkylamino, or aryloxyalkylamino group. In a particular embodiment, the HDAC inhibitor is a compound of structural formula 19 wherein $R_1$ and $R_2$ are both hydroxylamino.

In one particular embodiment of formula 19, $R_1$ is a phenylamino group and $R_2$ is a hydroxylamino group.

In one embodiment, the HDAC inhibitor useful in the methods of the present invention is represented by the structure of formula 20, or a pharmaceutically acceptable salt or hydrate thereof:

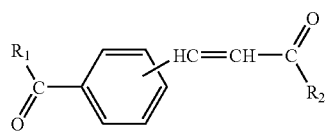

(20)

wherein each of $R_1$ and $R_2$ are independently the same as or different from each other and are a hydroxyl, alkyloxy, amino, hydroxylamino, alkylamino, dialkylamino, arylamino, alkylarylamino, alkyloxyamino, aryloxyamino, alkyloxyalkylamino, or aryloxyalkylamino group. In a particular embodiment, the HDAC inhibitor is a compound of structural formula 20 wherein $R_1$ and $R_2$ are both hydroxylamino.

In one embodiment the HDAC inhibitor useful in the methods of the present invention is represented by the structure of formula 21, or a pharmaceutically acceptable salt or hydrate thereof:

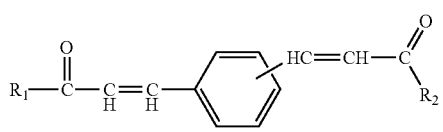

(21)

wherein each of $R_1$ and $R_2$ are independently the same as or different from each other and are a hydroxyl, alkyloxy, amino, hydroxylamino, alkylamino, dialkylamino, arylamino, alkylarylamino, alkyloxyamino, aryloxyamino, alkyloxyalkylamino, or aryloxyalkylamino group. In a particular embodiment, the HDAC inhibitor is a compound of structural formula 21 wherein $R_1$ and $R_2$ are both hydroxylamino.

In one embodiment, the HDAC inhibitor useful in the methods of the present invention is represented by the structure of formula 22, or a pharmaceutically acceptable salt or hydrate thereof:

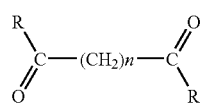

(22)

wherein R is a phenylamino group substituted with a cyano, methylcyano, nitro, carboxyl, aminocarbonyl, methylaminocarbonyl, dimethylaminocarbonyl, trifluoromethyl, hydroxylaminocarbonyl, N-hydroxylaminocarbonyl, methoxycarbonyl, chloro, fluoro, methyl, methoxy, 2,3-difluoro, 2,4-difluoro, 2,5-difluoro, 2,6-difuloro, 3,5-difluoro, 2,3,6-trifluoro, 2,4,6-trifluoro, 1,2,3-trifluoro, 3,4,5-trifluoro, 2,3,4,5-tetrafluoro, or 2,3,4,5,6-pentafluoro group; and n is an integer from 4 to 8.

In one embodiment, the HDAC inhibitor useful in the methods of the present invention is represented by the structure of formula 23 (m-carboxycinnamic acid bishydroxamide-(CBHA), or a pharmaceutically acceptable salt or hydrate thereof:

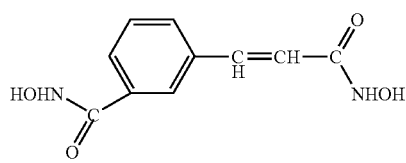

(23)

In one embodiment, the HDAC inhibitor useful in the methods of the present invention is represented by the structure of formula 24, or a pharmaceutically acceptable salt or hydrate thereof:

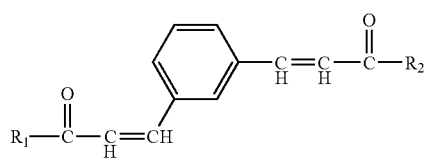

(24)

In one embodiment, the HDAC inhibitor useful in the methods of the present invention is represented by the structure of formula 25, or a pharmaceutically acceptable salt or hydrate thereof:

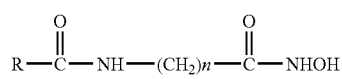

(25)

wherein R is a substituted or unsubstituted phenyl, piperidine, thiazole, 2-pyridine, 3-pyridine or 4-pyridine and n is an integer from about 4 to about 8.

In one particular embodiment of formula 25, R is a substituted phenyl group. In another particular embodiment of formula 25, R is a substituted phenyl group, where the substituent is selected from the group consisting of methyl, cyano, nitro, thio, trifluoromethyl, amino, aminocarbonyl, methylcyano, chloro, fluoro, bromo, iodo, 2,3-difluoro, 2,4-difluoro, 2,5-difluoro, 3,4-difluoro, 3,5-difluoro, 2,6-difluoro, 1,2,3-trifluoro, 2,3,6-trifluoro, 2,4,6-trifluoro, 3,4,5-trifluoro, 2,3,5,6-tetrafluoro, 2,3,4,5,6-pentafluoro, azido, hexyl, t-butyl, phenyl, carboxyl, hydroxyl, methyloxy, phenyloxy, benzyloxy, phenylaminooxy, phenylaminocarbonyl, methyloxycarbonyl, methylaminocarbonyl, dimethylamino, dimethylaminocarbonyl, or hydroxylaminocarbonyl group.

In another particular embodiment of formula 25, R is a substituted or unsubstituted 2-pyridine, 3-pyridine or 4-pyridine and n is an integer from about 4 to about 8.

In one embodiment, the HDAC inhibitor useful in the methods of the present invention is represented by the structure of formula 26, or a pharmaceutically acceptable salt or hydrate thereof:

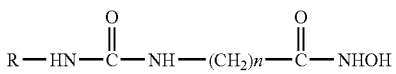

(26)

wherein R is a substituted or unsubstituted phenyl, pyridine, piperidine or thiazole group and n is an integer from about 4 to about 8 or a pharmaceutically acceptable salt thereof.

In a particular embodiment of formula 26, R is a substituted phenyl group. In another particular embodiment of formula 26, R is a substituted phenyl group, where the substituent is selected from the group consisting of methyl, cyano, nitro, thio, trifluoromethyl, amino, aminocarbonyl, methylcyano, chloro, fluoro, bromo, iodo, 2,3-difluoro, 2,4-difluoro, 2,5-difluoro, 3,4-difluoro, 3,5-difluoro, 2,6-difluoro, 1,2,3-trifluoro, 2,3,6-trifluoro, 2,4,6-trifluoro, 3,4,5-trifluoro, 2,3,5,6-tetrafluoro, 2,3,4,5,6-pentafluoro, azido, hexyl, t-butyl, phenyl, carboxyl, hydroxyl, methyloxy, phenyloxy, benzyloxy, phenylaminooxy, phenylaminocarbonyl, methyloxycarbonyl, methylaminocarbonyl, dimethylamino, dimethylaminocarbonyl, or hydroxylaminocarbonyl group.

In another particular embodiment of formula 26, R is phenyl and n is 5. In another embodiment, n is 5 and R is 3-chlorophenyl.

In one embodiment, the HDAC inhibitor useful in the methods of the present invention is represented by the structure of formula 27, or a pharmaceutically acceptable salt or hydrate thereof:

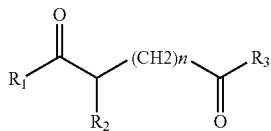

(27)

wherein each of $R_1$ and $R_2$ is directly attached or through a linker and is substituted or unsubstituted, aryl (e.g., phenyl), arylalkyl (e.g., benzyl), naphthyl, cycloalkyl, cycloalkylamino, pyridineamino, piperidino, 9-purine-6-amino, thiazoleamino, hydroxyl, branched or unbranched alkyl, alkenyl, alkyloxy, aryloxy, arylalkyloxy, pyridyl, or quinolinyl or isoquinolinyl; n is an integer from about 3 to about 10 and $R_3$ is a hydroxamic acid, hydroxylamino, hydroxyl, amino, alkylamino or alkyloxy group. The linker can be an amide moiety, e.g., O—, —S—, —NH—, $NR_5$, —$CH_2$—, —$(CH_2)_m$—, —(CH=CH)—, phenylene, cycloalkylene, or any combination thereof, wherein $R_5$ is a substitute or unsubstituted $C_1$-$C_5$ alkyl.

In certain embodiments of formula 27, $R_1$ is —NH—$R_4$ wherein $R_4$ is substituted or unsubstituted, aryl (e.g., phenyl), arylalkyl (e.g., benzyl), naphthyl, cycloalkyl, cycloalkylamino, pyridineamino, piperidino, 9-purine-6-amino, thiazoleamino, hydroxyl, branched or unbranched alkyl, alkenyl, alkyloxy, aryloxy, arylalkyloxy, pyridyl, quinolinyl or isoquinolinyl.

In one embodiment, the HDAC inhibitor useful in the methods of the present invention is represented by the structure of formula 28, or a pharmaceutically acceptable salt or hydrate thereof:

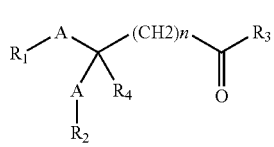

(28)

wherein each of $R_1$ and $R_2$ is, substituted or unsubstituted, aryl (e.g., phenyl), arylalkyl (e.g., benzyl), naphthyl, cycloalkyl, cycloalkylamino, pyridineamino, piperidino, 9-purine-6-amino, thiazoleamino, hydroxyl, branched or unbranched alkyl, alkenyl, alkyloxy, aryloxy, arylalkyloxy, pyridyl, quinolinyl or isoquinolinyl; $R_3$ is hydroxamic acid, hydroxylamino, hydroxyl, amino, alkylamino or alkyloxy group; $R_4$ is hydrogen, halogen, phenyl or a cycloalkyl moiety; and A can be the same or different and represents an amide moiety, O—, —S—, —NH—, $NR_5$, —$CH_2$—, —$(CH_2)_m$—, —(CH=CH)—, phenylene, cycloalkylene, or any combination thereof wherein $R_5$ is a substitute or unsubstituted $C_1$-$C_5$ alkyl; and n and m are each an integer from 3 to 10.

In further particular embodiment a compounds having a more specific structure within the scope of compounds 27 or 28 is compound 29.

In one ombodiment, the HDAC inhibitor useful in the methods of the present invention is represented by the structure of formula 29, or a pharmaceutically acceptable salt or hydrate thereof:

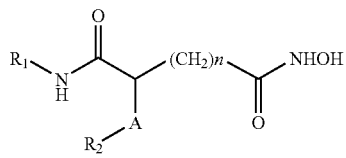

(29)

wherein A is an amide moiety, $R_1$ and $R_2$ are each selected from substituted or unsubstituted aryl (e.g., phenyl), arylalkyl (e.g., benzyl), naphthyl, pyridineamino, 9-purine-6-amino, thiazoleamino, aryloxy, arylalkyloxy, pyridyl, quinolinyl or isoquinolinyl; and n is an integer from 3 to 10.

For example, the compound of formula 29 can have the structure 30 or 31:

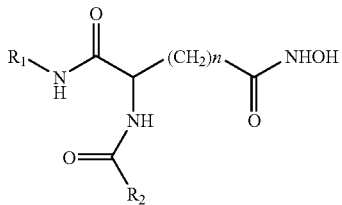
(30)

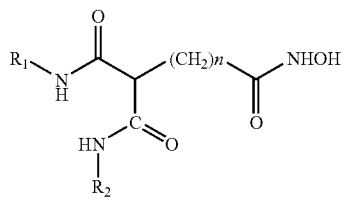
(31)

wherein $R_1$, $R_2$ and n have the meanings of formula 29.

In one embodiment, the HDAC inhibitor useful in the methods of the present invention is represented by the structure of formula 32 or a pharmaceutically acceptable salt or hydrate thereof:

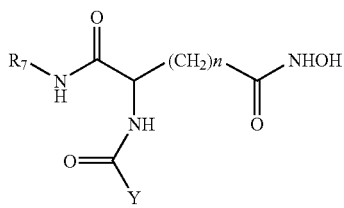
(32)

wherein $R_7$ is selected from substituted or unsubstituted aryl (e.g., phenyl), arylalkyl (e.g., benzyl), naphthyl, pyridineamino, 9-purine-6-amino, thiazoleamino, aryloxy, arylalkyloxy, pyridyl, quinolinyl or isoquinolinyl; n is an integer from 3 to 10 and Y is selected from:

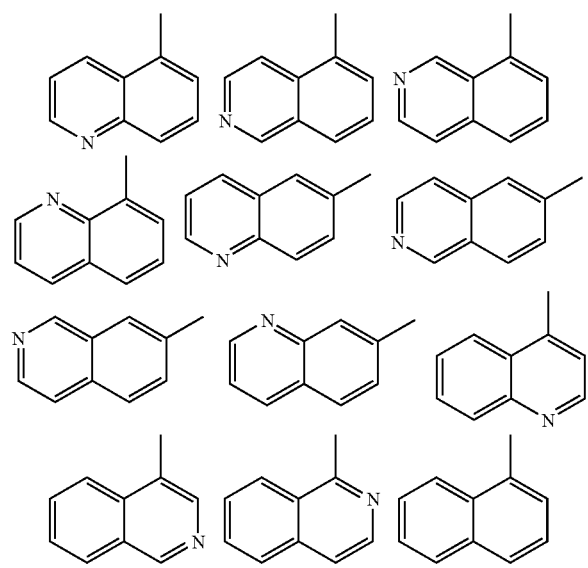

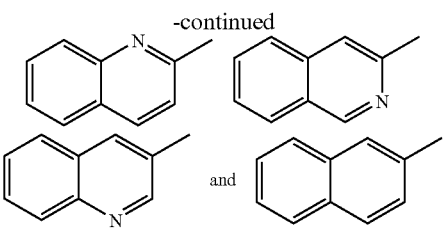

In one embodiment, the HDAC inhibitor useful in the methods of the present invention is represented by the structure of formula 33 or a pharmaceutically acceptable salt or hydrate thereof:

(34)

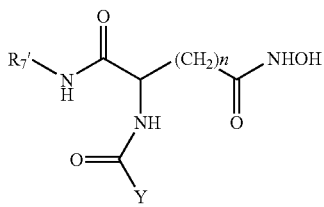

wherein n is an integer from 3 to 10, Y is selected from

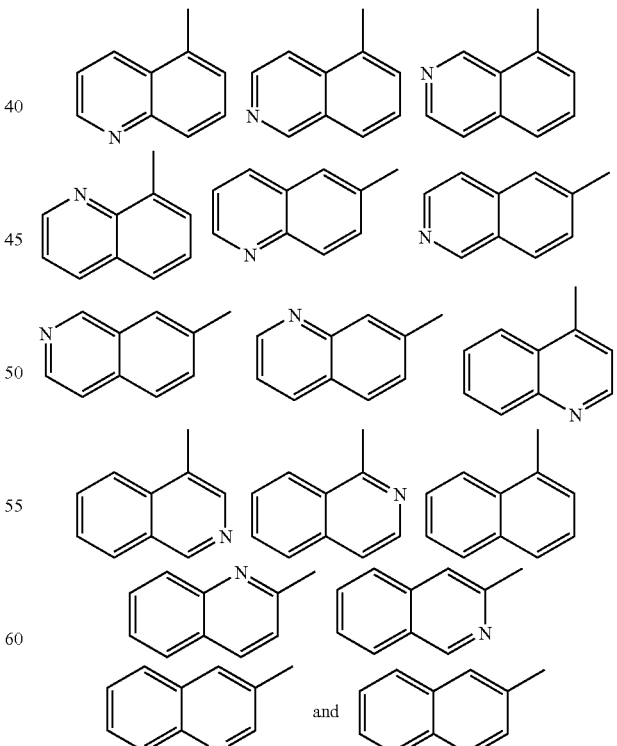

and $R_7'$ is selected from

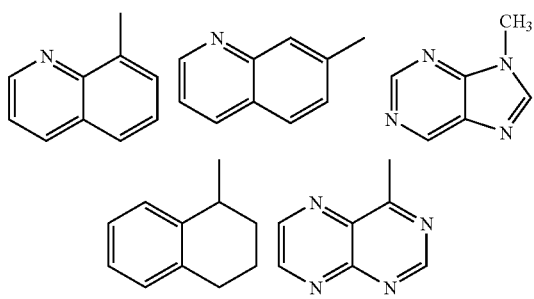

In one embodiment, the HDAC inhibitor useful in the methods of the present invention is represented by the structure of formula 34 or a pharmaceutically acceptable salt or hydrate thereof:

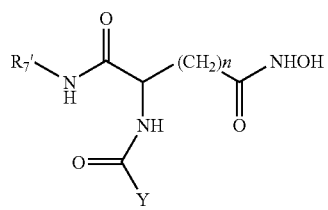
(35)

aryl (e.g., phenyl), arylalkyl (e.g., benzyl), naphthyl, pyridineamino, 9-purine-6-amino, thiazoleamino, aryloxy, arylalkyloxy, pyridyl, quinolinyl or isoquinolinyl; n is an integer from 3 to 10 and $R_7'$ is selected from

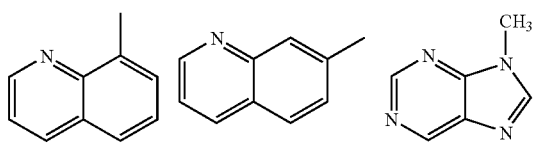

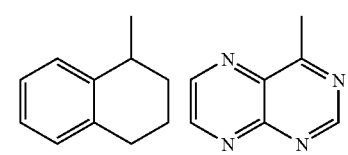

In one embodiment, the HDAC inhibitor useful in the methods of the present invention is represented by the structure of formula 35 or a pharmaceutically acceptable salt or hydrate thereof:

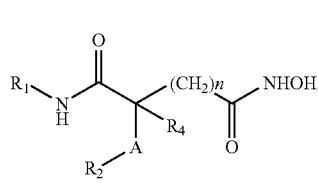
(35)

wherein A is an amide moiety, $R_1$ and $R_2$ are each selected from substituted or unsubstituted aryl (e.g., phenyl), arylalkyl (e.g., benzyl), naphthyl, pyridineamino, 9-purine-6-amino, thiazoleamino, aryloxy, arylalkyloxy, pyridyl, quinolinyl or isoquinolinyl; $R_4$ is hydrogen, a halogen, a phenyl or a cycloalkyl moiety and n is an integer from 3 to 10.

For example, the compound of formula 35 can have the structure of formulas 36 or 37:

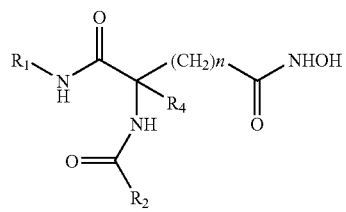
(36)

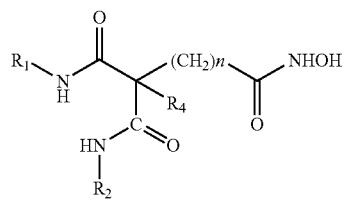
(37)

wherein $R_1$, $R_2$, $R_4$ and n have the meanings of formula 35.

In one embodiment, the HDAC inhibitor useful in the methods of the present invention is represented by the structure of formula 38 or a pharmaceutically acceptable salt or hydrate thereof:

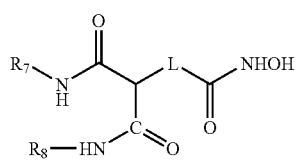
(38)

wherein L is a linker selected from the group consisting of an amide moiety, O—, —S—, —NH—, $NR_5$, —$CH_2$—, —$(CH_2)_m$—, —(CH=CH)—, phenylene, cycloalkylene, or any combination thereof wherein $R_5$ is a substitute or unsubstituted $C_1$-$C_5$ alkyl; and wherein each of $R_7$ and $R_8$ are independently a substituted or unsubstituted aryl (e.g., phenyl), arylalkyl (e.g., benzyl), naphthyl, pyridineamino, 9-purine-6-amino, thiazoleamino, aryloxy, arylalkyloxy, pyridyl, quinolinyl or isoquinolinyl; n is an integer from 3 to 10 and m is an integer from 0-10.

For example, a compound of formula 38 can be represented by the structure of formula (39):

A compound represented by the structure:

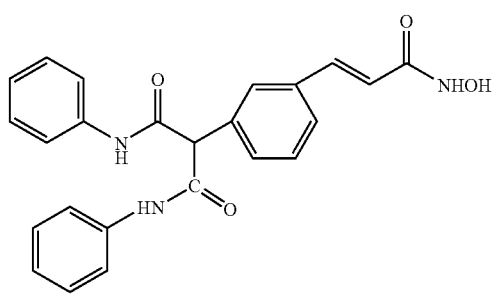
(39)

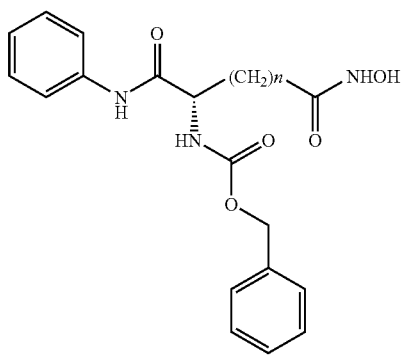
(42)

Other HDAC inhibitors suitable for use in the invention include those shown in the following more specific formulas:

A compound represented by the structure:

wherein n is an integer from 3 to 10 or an enantiomer thereof. In one particular embodiment of formula 42, n=5.

A compound represented by the structure:

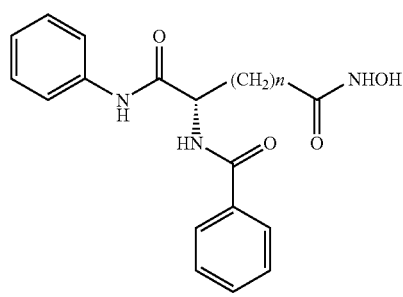
(40)

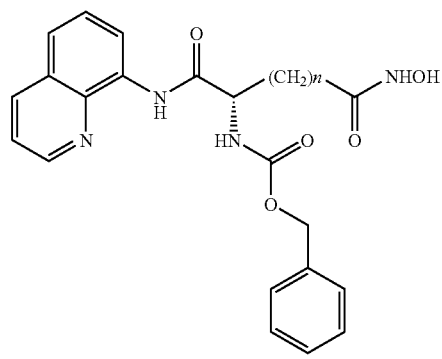
(43)

wherein n is an integer from 3 to 10, or an enantiomer. In one particular embodiment of formula 40, n=5.

A compound represented by the structure:

wherein n is an integer from 3 to 10, or an enantiomer thereof. In one particular embodiment of formula 43, n=5.

A compound represented by the structure:

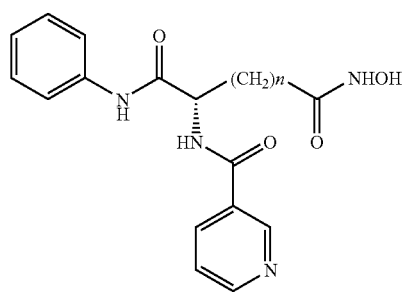
(41)

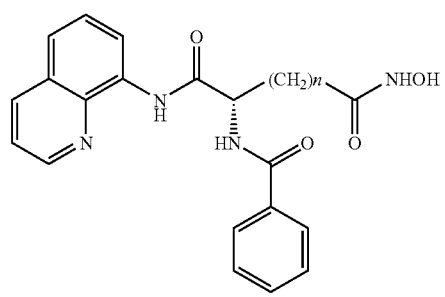
(44)

wherein n is an integer from 3 to 10 or an enantiomer thereof. In one particular embodiment of formula 41, n=5.

wherein n is an integer from 3 to 10 or an enantiomer thereof.
In one particular embodiment of formula 44, n=5.
A compound represented by the structure:

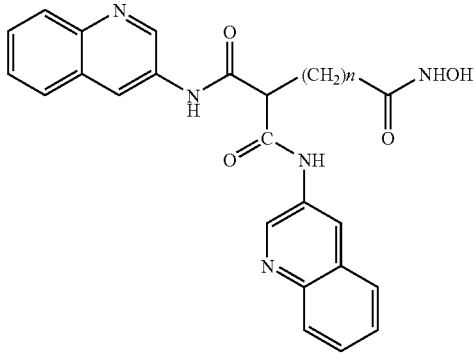
(45)

wherein n is an integer from 3 to 10 or an enantiomer thereof.
In one particular embodiment of formula 45, n=5.
A compound represented by the structure:

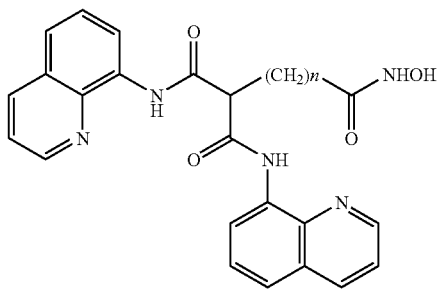
(46)

wherein n is an integer from 3 to 10 or an enantiomer thereof.
In one particular embodiment of formula 46, n=5.
A compound represented by the structure:

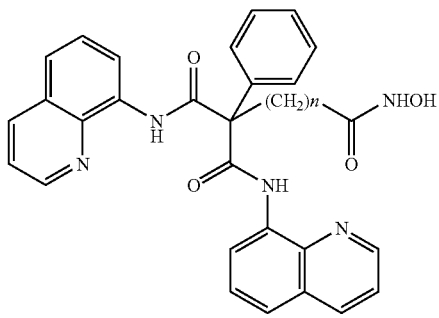
(47)

wherein n is an integer from 3 to 10 or an enantiomer thereof.
In one particular embodiment of formula 47, n=5.
A compound represented by the structure:

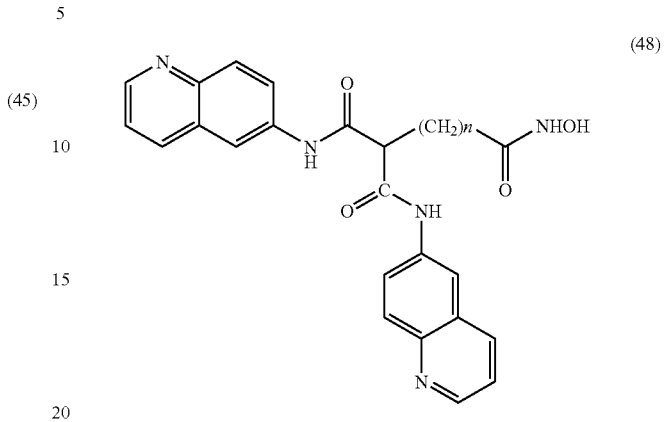
(48)

wherein n is an integer from 3 to 10 or an enantiomer thereof.
In one particular embodiment of formula 48, n=5.
A compound represented by the structure:

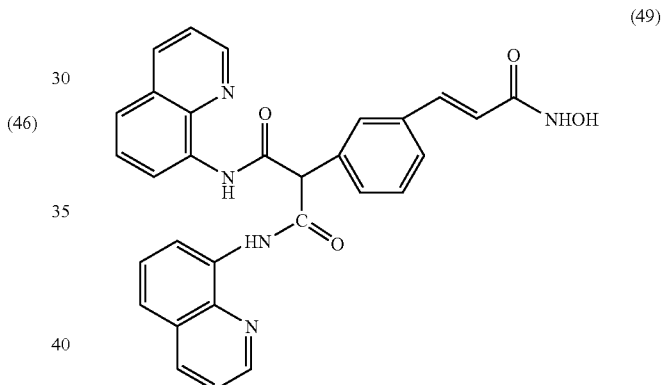
(49)

wherein n is an integer from 3 to 10 or an enantiomer thereof.
In one particular embodiment of formula 49, n=5.
A compound represented by the structure:

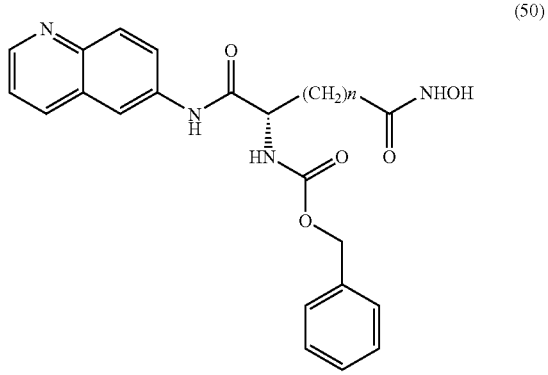
(50)

wherein n is an integer from 3 to 10 or an enantiomer thereof.
In one particular embodiment of formula 50, n=5.

A compound represented by the structure:

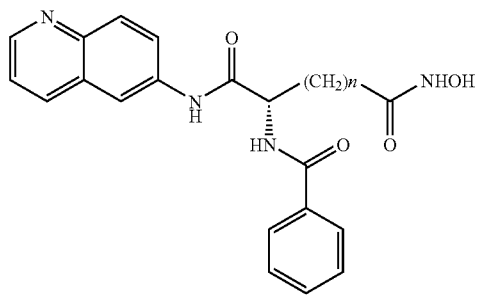
(51)

wherein n is an integer from 3 to 10 or an enantiomer thereof. In one particular embodiment of formula 51, n=5.

Other examples of such compounds and other HDAC inhibitors can be found in U.S. Pat. No. 5,369,108, issued on Nov. 29, 1994, U.S. Pat. No. 5,700,811, issued on Dec. 23, 1997, U.S. Pat. No. 5,773,474, issued on Jun. 30, 1998, U.S. Pat. No. 5,932,616, issued on Aug. 3, 1999 and U.S. Pat. No. 6,511,990, issued Jan. 28, 2003, all to Breslow et al.; U.S. Pat. No. 5,055,608, issued on Oct. 8, 1991, U.S. Pat. No. 5,175,191, issued on Dec. 29, 1992 and U.S. Pat. No. 5,608,108, issued on Mar. 4, 1997, all to Marks et al.; as well as Yoshida, M., et al., Bioassays 17, 423-430 (1995); Saito, A., et al., PNAS USA 96, 4592-4597, (1999); Furamai R. et al., PNAS USA 98 (1), 87-92 (2001); Komatsu, Y., et al., Cancer Res. 61(11), 4459-4466 (2001); Su, G. H., et al., Cancer Res. 60, 3137-3142 (2000); Lee, B. I. et al., Cancer Res. 61(3), 931-934; Suzuki, T., et al., J. Med. Chem. 42(15), 3001-3003 (1999); published PCT Application WO 01/18171 published on Mar. 15, 2001 to Sloan-Kettering Institute for Cancer Research and The Trustees of Columbia University; published PCT Application WO02/246144 to Hoffmann-La Roche; published PCT Application WO02/22577 to Novartis; published PCT Application WO02/30879 to Prolifix; published PCT Applications WO 01/38322 (published May 31, 2001), WO 01/70675 (published on Sep. 27, 2001) and WO 00/71703 (published on Nov. 30, 2000) all to Methylgene, Inc.; published PCT Application WO 00/21979 published on Oct. 8, 1999 to Fujisawa Pharmaceutical Co., Ltd.; published PCT Application WO 98/40080 published on Mar. 11, 1998 to Beacon Laboratories, L.L.C.; and Curtin M. (Current patent status of histone deacetylase inhibitors Expert Opin. Ther. Patents (2002) 12(9): 1375-1384 and references cited therein).

SAHA or any of the other HDACs can be synthesized according to the methods outlined in the Experimental Details Section, or according to the method set forth in U.S. Pat. Nos. 5,369,108, 5,700,811, 5,932,616 and 6,511,990, the contents of which are incorporated by reference in their entirety, or according to any other method known to a person skilled in the art.

This invention, in addition to the above listed compounds, is intended to encompass the use of homologs and analogs of such compounds. In this context, homologs are molecules having substantial structural similarities to the above-described compounds and analogs are molecules having substantial biological similarities regardless of structural similarities.

The invention also encompasses pharmaceutical compositions comprising pharmaceutically acceptable salts of the HDAC inhibitors with organic and inorganic acids, for example, acid addition salts which may, for example, be hydrochloric acid, sulphuric acid, methanesulphonic acid, fumaric acid, maleic acid, succinic acid, acetic acid, benzoic: acid, oxalic acid, citric acid, tartaric acid, carbonic acid, phosphoric acid and the like. Pharmaceutically acceptable salts can also be prepared from by treatment with inorganic bases, for example, sodium, potassium, ammonium, calcium, or ferric hydroxides, and such organic bases as isopropylamine, trimethylamine, 2-ethylamino ethanol, histidine, procaine, and the like.

The invention also encompasses pharmaceutical compositions comprising hydrates of the HDAC inhibitors and/or the anti-cancer agents. The term "hydrate" includes but is not limited to hemihydrate, monohydrate, dihydrate, trihydrate and the like.

In addition, this invention also encompasses pharmaceutical compositions comprising any solid or liquid physical form of SAHA or any of the other HDAC inhibitors. For example, The HDAC inhibitors can be in a crystalline form, in amorphous form, and have any particle size. The HDAC inhibitor particles may be micronized, or may be agglomerated, particulate granules, powders, oils, oily suspensions or any other form of solid or liquid physical form.

Pharmaceutical Compositions

The compounds of the invention, and derivatives, fragments, analogs, homologs pharmaceutically acceptable salts or hydrate thereof, can be incorporated into pharmaceutical compositions suitable for oral administration, together with a pharmaceutically acceptable carrier or excipient. Such compositions typically comprise a therapeutically effective amount of any of the compounds above, and a pharmaceutically acceptable carrier. Preferably, the effective amount is an amount effective to selectively induce terminal differentiation of suitable neoplastic cells and less than an amount which causes toxicity in a patient.

Any inert excipient that is commonly used as a carrier or diluent may be used in the formulations of the present invention, such as for example, a gum, a starch, a sugar, a cellulosic material, an acrylate, or mixtures thereof. A preferred diluent is microcrystalline cellulose. The compositions may further comprise a disintegrating agent (e.g., croscarmellose sodium) and a lubricant (e.g., magnesium stearate), and in addition may comprise one or more additives selected from a binder, a buffer, a protease inhibitor, a surfactant, a solubilizing agent, a plasticizer, an emulsifier, a stabilizing agent, a viscosity increasing agent, a sweetener, a film forming agent, or any combination thereof. Furthermore, the compositions of the present invention may be in the form of controlled release or immediate release formulations.

One embodiment is a pharmaceutical composition for oral administration comprising a HDAC inhibitor or a pharmaceutically acceptable salt or hydrate thereof, microcrystalline cellulose, croscarmellose sodium and magnesium stearate. Another embodiment has SAHA as the HDAC inhibitor. Another embodiment comprises 50-70% by weight of a HDAC inhibitor or a pharmaceutically acceptable salt or hydrate thereof, 20-40% by weight microcrystalline cellulose, 5-15% by weight croscarmellose sodium and 0.1-5% by weight magnesium stearate. Another embodiment comprises about 50-200 mg of a HDAC inhibitor.

In one embodiment, the pharmaceutical compositions are administered orally, and are thus formulated in a form suitable for oral administration, i.e., as a solid or a liquid preparation. Suitable solid oral formulations include tablets, capsules, pills, granules, pellets and the like. Suitable liquid oral formulations include solutions, suspensions, dispersions, emulsions, oils and the like. In one embodiment of the present invention, the composition is formulated in a capsule. In accordance with this embodiment, the compositions of the present invention comprise in addition to the HDAC inhibitor active compound and the inert carrier or diluent, a hard gelatin capsule.

As used herein, "pharmaceutically acceptable carrier" is intended to include any and all solvents, dispersion media, coatings, antibacterial and antifungal agents, isotonic and absorption delaying agents, and the like, compatible with pharmaceutical administration, such as sterile pyrogen-free water. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

Solid carriers/diluents include, but are not limited to, a gum, a starch (e.g., corn starch, pregelatinized starch), a sugar (e.g., lactose, mannitol, sucrose, dextrose), a cellulosic material (e.g., microcrystalline cellulose), an acrylate (e.g., polymethylacrylate), calcium carbonate, magnesium oxide, talc, or mixtures thereof.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil. Solutions or suspensions can also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide.

In addition, the compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol), a glidant (e.g., colloidal silicon dioxide), anti-oxidants (e.g., ascorbic acid, sodium metabisulfite, butylated hydroxyanisole), stabilizers (e.g., hydroxypropyl cellulose, hyroxyanpropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The daily administration is then repeated continuously for a period of several days to several years. Oral treatment may continue for between one week and the life of the patient. Preferably the administration takes place for five consecutive days after which time the patient can be evaluated to determine if further administration is required. The administration can be continuous or intermittent, i.e., treatment for a number of consecutive days followed by a rest period.

The compounds of the present invention may be administered intravenously on the first day of treatment, with oral administration on the second day and all consecutive days thereafter.

The compounds of the present invention may be administered for the purpose of preventing disease progression or stabilizing tumor growth.

The preparation of pharmaceutical compositions that contain an active component is well understood in the art, for example, by mixing, granulating, or tablet-forming processes. The active therapeutic ingredient is often mixed with excipients that are pharmaceutically acceptable and compatible with the active ingredient. For oral administration, the active agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions and the like as detailed above.

The amount of the compound administered to the patient is less than an amount that would cause toxicity in the patient. In the certain embodiments, the amount of the compound that is administered to the patient is less than the amount that causes a concentration of the compound in the patient's plasma to equal or exceed the toxic level of the compound. Preferably, the concentration of the compound in the patient's plasma is maintained at about 10 nM. In another embodiment, the concentration of the compound in the patient's plasma is maintained at about 25 nM. In another embodiment, the concentration of the compound in the patient's plasma is maintained at about 50 nM. In another embodiment, the concentration of the compound in the patient's plasma is maintained at about 100 nM. In another embodiment, the concentration of the compound in the patient's plasma is maintained at about 500 nM. In another embodiment, the concentration of the compound in the patient's plasma is maintained at about 1000 nM. In another embodiment, the concentration of the compound in the patient's plasma is maintained at about 2500 nM. In another embodiment, the concentration of the compound in the patient's plasma is maintained at about 5000 nM. It has been found with HMBA that administration of the compound in an amount from about 5 $gm/m^2/day$ to about 30 $gm/m^2/day$, particularly about 20 $gm/m^2/day$, is effective without producing toxicity in the patient. The optimal amount of the compound that should be administered to the patient in the practice of the present invention will depend on the particular compound used and the type of cancer being treated.

In a currently preferred embodiment of the present invention, the pharmaceutical composition comprises a histone deacetylase (HDAC) inhibitor; microcrystalline cellulose as a carrier or diluent; croscarmellose sodium as a disintegrant; and magnesium stearate as a lubricant. In a particularly preferred embodiment, the HDAC inhibitor is suberoylanilide hydroxamic acid (SAHA).

The percentage of the active ingredient and various excipients in the formulations may vary. For example, the composition may comprise between 20 and 90%, preferably between 50-70% by weight of the histone deacetylase (HDAC). Furthermore, the composition may comprise between 10 and 70%, preferably between 20-40% by weight microcrystalline cellulose as a carrier or diluent. Furthermore, the composition may comprise between 1 and 30%, preferably 5-15% by weight croscarmellose sodium as a disintegrant. Furthermore, the composition may comprise between 0.1-5% by weight magnesium stearate as a lubricant. In another preferred embodiment, the composition comprises about 50-200 mg of the HDAC inhibitor (e.g., 50 mg, 100 mg and 200 mg for the HDAC inhibitor, for example, SAHA). In a particularly preferred embodiment, the composition is in the form of a gelatin capsule.

A currently preferred embodiment of the invention is a solid formulation of SAHA with microcrystalline cellulose, NF (Avicel Ph 101), sodium croscarmellose, NF (AC-Di-Sol) and magnesium stearate, NF, contained in a gelatin capsule. A further preferred embodiment is 200 mg of solid SAHA with 89.5 mg of microcrystalline cellulose, 9 mg of sodium croscarmellose and 1.5 mg of magnesium stearate contained in a gelatin capsule.

It should be apparent to a person skilled in the art that the pharmaceutical compositions of the present invention are not only useful for inhibiting the proliferation of neoplastic cells induction and treatment of cancer, and that these compositions are useful in treating a wide range of diseases for which HDAC inhibitors have been found useful.

For example, HDAC inhibitors, and in particular SAHA, have been found to be useful in the treatment of a variety of acute and chronic inflammatory diseases, autoimmune diseases, allergic diseases, diseases associated with oxidative stress, and diseases characterized by cellular hyperproliferation. Non-limiting examples are inflammatory conditions of a joint including and rheumatoid arthritis (RA) and psoriatic arthritis; inflammatory bowel diseases such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs, ischemic injury, including cerebral ischemia (e.g., brain injury as a result of trauma, epilepsy, hemorrhage or stroke, each of which may lead to neurodegeneration); HIV, heart failure, chronic, acute or malignant liver disease, autoimmune thyroiditis; systemic lupus erythematosus, Sjorgren's syndrome, lung diseases (e.g., ARDS); acute pancreatitis; amyotrophic lateral sclerosis (ALS); Alzheimer's disease; cachexia/anorexia; asthma; atherosclerosis; chronic fatigue syndrome, fever; diabetes (e.g., insulin diabetes or juvenile onset diabetes); glomerulonephritis; graft versus host rejection (e.g., in transplantation); hemohorragic shock; hyperalgesia: inflammatory bowel disease; multiple sclerosis; myopathies (e.g., muscle protein metabolism, esp. in sepsis); osteoporosis; Parkinson's disease; pain; pre-term labor; psoriasis; reperfusion injury; cytokine-induced toxicity (e.g., septic shock, endotoxic shock); side effects from radiation therapy, temporal mandibular joint disease, tumor metastasis; or an inflammatory condition resulting from strain, sprain, cartilage damage, trauma such as burn, orthopedic surgery, infection or other disease processes. Allergic diseases and conditions, include but are not limited to respiratory allergic diseases such as asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersentitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies, and the like.

For example, HDAC inhibitors, and in particular SAHA, have been found to be useful in the treatment of a variety of neurodegenerative diseases, a non-exhaustive list of which is:

I. Disorders characterized by progressive dementia in the absence of other prominent neurologic signs, such as Alzheimer's disease; Senile dementia of the Alzheimer type; and Pick's disease (lobar atrophy).

II. Syndromes combining progressive dementia with other prominent neurologic abnormalities such as A) syndromes appearing mainly in adults (e.g., Huntington's disease, Multiple system atrophy combining dementia with ataxia and/or manifestations of Parkinson's disease, Progressive supranuclear palsy (Steel-Richardson-Olszewski), diffuse Lewy body disease, and corticodentatonigral degeneration); and B) syndromes appearing mainly in children or young adults (e.g., Hallervorden-Spatz disease and progressive familial myoclonic epilepsy).

III. Syndromes of gradually developing abnormalities of posture and movement such as paralysis agitans (Parkinson's disease), striatonigral degeneration, progressive supranuclear palsy, torsion dystonia (torsion spasm; dystonia musculorum deformans), spasmodic torticollis and other dyskinesis, familial tremor, and Gilles de la Tourette syndrome.

IV. Syndromes of progressive ataxia such as cerebellar degenerations (e.g., cerebellar cortical degeneration and olivopontocerebellar atrophy (OPCA)); and spinocerebellar degeneration (Friedreich's atazia and related disorders).

V. Syndrome of central autonomic nervous system failure (Shy-Drager syndrome).

VI. Syndromes of muscular weakness and wasting without sensory changes (motorneuron disease such as amyotrophic lateral sclerosis, spinal muscular atrophy (e.g., infantile spinal muscular atrophy (Werdnig-Hoffman), juvenile spinal muscular atrophy (Wohlfart-Kugelberg-Welander) and other forms of familial spinal muscular atrophy), primary lateral sclerosis, and hereditary spastic paraplegia.

VII. Syndromes combining muscular weakness and wasting with sensory changes (progressive neural muscular atrophy; chronic familial polyneuropathies) such as peroneal muscular atrophy (Charcot-Marie-Tooth), hypertrophic interstitial polyneuropathy (Dejerine-Sottas), and miscellaneous forms of chronic progressive neuropathy.

VIII Syndromes of progressive visual loss such as pigmentary degeneration of the retina (retinitis pigmentosa), and hereditary optic atrophy (Leber's disease).

The invention is illustrated by the examples in the Experimental Details Section that follows. This section is set forth to aid in an understanding of the invention but is not intended to, and should not be construed to limit in any way the invention as set forth in the claims which follow thereafter.

EXPERIMENTAL DETAILS SECTION

EXAMPLE 1

Synthesis of SAHA

SAHA can be synthesized according to the method outlined below, or according to the method set forth in U.S. Pat. No. 5,369,108, the contents of which are incorporated by reference in their entirety, or according to any other method.

Synthesis of SAHA

Step 1—Synthesis of Suberanilic Acid

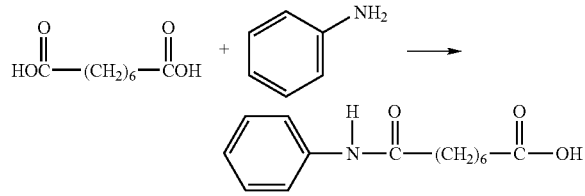

In a 22 L flask was placed 3,500 g (20.09 moles) of suberic acid, and the acid melted with heat. The temperature was raised to 175° C., and then 2,040 g (21.92 moles) of aniline was added. The temperature was raised to 190° C. and held at that temperature for 20 minutes. The melt was poured into a Nalgene tank that contained 4,017 g of potassium hydroxide dissolved in 50 L of water. The mixture was stirred for 20 minutes following the addition of the melt. The reaction was repeated at the same scale, and the second melt was poured into the same solution of potassium hydroxide. After the mixture was thoroughly stirred, the stirrer was turned off, and the mixture was allowed to settle. The mixture was then filtered through a pad of Celite (4,200 g) (the product was filtered to remove the neutral by-product (from attack by aniline on both ends of suberic acid). The filtrate contained the salt of the product, and also the salt of unreacted suberic acid. The mixture was allowed to settle because the filtration was very slow, taking several days.). The filtrate was acidified using 5 L of concentrated hydrochloric acid; the mixture was stirred for one hour, and then allowed to settle overnight. The product was collected by filtration, and washed on the funnel with deionized water (4×5 L). The wet filter cake was placed in a 72 L flask with 44 L of deionized water, the mixture heated to 50° C., and the solid isolated by a hot filtration (the desired product was contaminated with suberic acid which is has a much greater solubility in hot water. Several hot triturations were done to remove suberic acid. The product was checked by NMR [$D_6$DMSO] to monitor the removal of suberic acid). The hot trituration was repeated with 44 L of water at 50° C. The product was again isolated by filtration, and rinsed with 4 L of hot water. It was dried over the weekend in a vacuum oven at 65° C. using a Nash pump as the vacuum source (the Nash pump is a liquid ring pump (water) and pulls a vacuum of about 29 inch of mercury. An intermittent argon purge was used to help carry off water); 4,182.8 g of suberanilic acid was obtained.

The product still contained a small amount of suberic acid; therefore the hot trituration was done portionwise at 65° C., using about 300 g of product at a time. Each portion was filtered, and rinsed thoroughly with additional hot water (a total of about 6 L). This was repeated to purify the entire batch. This completely removed suberic acid from the product. The solid product was combined in a flask and stirred with 6 L of methanol/water (1:2), and then isolated by filtration and air dried on the filter over the week end. It was placed in trays and dried in a vacuum oven at 65° C. for 45 hours using the Nash pump and an argon bleed. The final product has a weight of 3,278.4 g (32.7% yield).

Step 2—Synthesis of Methyl Suberanilate

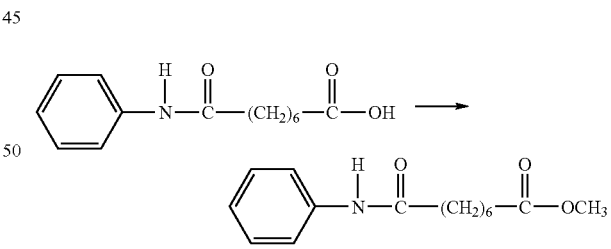

To a 50 L flask fitted with a mechanical stirrer, and condenser was placed 3,229 g of suberanilic acid from the previous step, 20 L of methanol, and 398.7 g of Dowex 50WX2-400 resin. The mixture was heated to reflux and held at reflux for 18 hours. The mixture was filtered to remove the resin beads, and the filtrate was taken to a residue on a rotary evaporator.

The residue from the rotary evaporator was transferred into a 50 L flask fitted with a condenser and mechanical stirrer. To the flask was added 6 L of methanol, and the mixture heated to give a solution. Then 2 L of deionized water was added, and the heat turned off. The stirred mixture was allowed to cool, and then the flask was placed in an ice bath, and the mixture cooled. The solid product was isolated by filtration, and the filter cake was rinsed with 4 L of cold methanol/water (1:1). The product was dried at 45° C. in a vacuum oven using a Nash pump for a total of 64 hours to give 2,850.2 g (84% yield) of methyl suberanilate, CSL Lot # 98-794-92-3 1.

Step 3—Synthesis of Crude SAHA

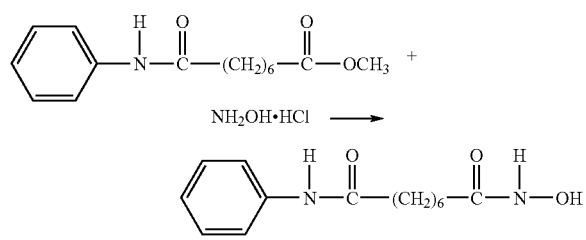

To a 50 L flask with a mechanical stirrer, thermocouple, and inlet for inert atmosphere was added 1,451.9 g of hydroxylamine hydrochloride, 19 L of anhydrous methanol, and a 3.93 L of a 30% sodium methoxide solution in methanol. The flask was then charged with 2,748.0 g of methyl suberanilate, followed by 1.9 L of a 30% sodium methoxide solution in methanol. The mixture was allowed to stir for 16 hr and 10 minutes. Approximately one half of the reaction mixture was transferred from the reaction flask (flask 1) to a 50 L flask (flask 2) fitted with a mechanical stirrer. Then 27 L of deionized water was added to flask 1 and the mixture was stirrer for 10 minutes. The pH was taken using a pH meter; the pH was 11.56. The pH of the mixture was adjusted to 12.02 by the addition of 100 ml of the 30% sodium methoxide solution in methanol; this gave a clear solution (the reaction mixture at this time contained a small amount of solid. The pH was adjusted to give a clear solution from which the precipitation the product would be precipitated). The reaction mixture in flask 2 was diluted in the same manner; 27 L of deionized water was added, and the pH adjusted by the addition of 100 ml of a 30% sodium methoxide solution to the mixture, to give a pH of 12.01 (clear solution).

The reaction mixture in each flask was acidified by the addition of glacial acetic acid to precipitate the product. Flask 1 had a final pH of 8.98, and Flask 2 had a final pH of 8.70. The product from both flasks was isolated by filtration using a Buchner funnel and filter cloth. The filter cake was washed with 15 L of deionized water, and the funnel was covered and the product was partially dried on the funnel under vacuum for 15.5 hr. The product was removed and placed into five glass trays. The trays were placed in a vacuum oven and the product was dried to constant weight. The first drying period was for 22 hours at 60° C. using a Nash pump as the vacuum source with an argon bleed. The trays were removed from the vacuum oven and weighed. The trays were returned to the oven and the product dried for an additional 4 hr and 10 minutes using an oil pump as the vacuum source and with no argon bleed. The material was packaged in double 4-mill polyethylene bags, and placed in a plastic outer container. The final weight after sampling was 2633.4 g (95.6%).

Step 4—Recrystallization of Crude SAHA

The crude SAHA was recrystallized from methanol/water. A 50 L flask with a mechanical stirrer, thermocouple, condenser, and inlet for inert atmosphere was charged with the crude SAHA to be crystallized (2,525.7 g), followed by 2,625 ml of deionized water and 15,755 ml of methanol. The material was heated to reflux to give a solution. Then 5,250 ml of deionized water was added to the reaction mixture. The heat was turned off, and the mixture was allowed to cool. When the mixture had cooled sufficiently so that the flask could be safely handled (28° C.), the flask was removed from the heating mantle, and placed in a tub for use as a cooling bath. Ice/water was added to the tub to cool the mixture to −5° C. The mixture was held below that temperature for 2 hours. The product was isolated by filtration, and the filter cake washed with 1.5 L of cold methanol/water (2:1). The funnel was covered, and the product was partially dried under vacuum for 1.75 hr. The product was removed from the funnel and placed in 6 glass trays. The trays were placed in a vacuum oven, and the product was dried for 64.75 hr at 60° C. using a Nash pump as the vacuum source, and using an argon bleed. The trays were removed for weighing, and then returned to the oven and dried for an additional 4 hours at 60° C. to give a constant weight. The vacuum source for the second drying period was a oil pump, and no argon bleed was used. The material was packaged in double 4-mill polyethylene bags, and placed in a plastic outer container. The final weight after sampling was 2,540.9 g (92.5%).

EXAMPLE 2

Oral Dosing of Suberoylanilide Hydroxamic Acid (SAHA)

Background: Treatment with hybrid polar cellular differentiation agents has resulted in the inhibition of growth of human solid tumor derived cell lines and xenografts. The effect is mediated in part by inhibition of histone deacetylase. SAHA is a potent histone deacetylase inhibitor that has been shown to have the ability to induce tumor cell growth arrest, differentiation and apoptosis in the laboratory and in preclinical studies.

Objectives: To define a safe daily oral regimen of SAHA that can be used in Phase II studies. In addition, the pharmacokinetic profile of the oral formulation of SAHA was be evaluated. The oral bioavailability of SAHA in humans in the fasting vs. non-fasting state and anti-tumor effects of treatment were also monitored. Additionally, the biological effects of SAHA on normal tissues and tumor cells were assessed and responses with respect to levels of histone acetylation were documented.

Patients: Patients with histologically documented advanced stage, primary or metastatic adult solid tumors that are refractory to standard therapy or for which no curative standard therapy exists. Patients must have a Karnofsky Performance Status of ≧70%, and adequate hematologic, hepatic and renal function. Patients must be at least four weeks from any prior chemotherapy, radiation therapy or other investigational anticancer drugs.

Dosing Schedule: On the first day, patients were first treated with 200 mg of intravenously-administered SAHA. Starting on the second day, patients were treated with daily doses of oral SAHA according to Table 1. Each cohort received a different dose of SAHA. "QD" indicates dosing once a day; "Q12 hours" indicates dosing twice a day. For example, patients in Cohort IV received two 800 mg doses of SAHA per day. Doses were administered to patients daily and continuously. Blood samples were taken on day one and on day 21 of oral treatment. Patients were taken off oral SAHA treatment due to disease progression, tumor regression, unacceptable side effects, or treatment with other therapies.

TABLE 1

Oral SAHA Dose Schedule

| Cohort | Oral Dose (mg) | Number of Days | Daily Dosing Schedule |
|---|---|---|---|
| I | 200 | Continuous | QD |
| II | 400 | Continuous | QD |
| III | 400 | Continuous | Q12 hours |
| IV | 800 | Continuous | Q12 hours |
| V | 1200 | Continuous | Q12 hours |
| VI | 1600 | Continuous | Q12 hours |
| VII | 2000 | Continuous | Q12 hours |

Results: Comparison of serum plasma levels shows high bioavailability of SAHA administered orally, both when the patient fasted and when the patient did not fast, compared to SAHA administered intravenously (IV SAHA). "AUC" is an estimate of the bioavailability of SAHA in (ng/ml)min, where 660 ng/ml is equal to 2.5 µM SAHA. The AUC taken together with the half-life ($t_{1/2}$) shows that the overall bioavailability of oral SAHA is better than that of IV SAHA. $C_{max}$ is the maximum concentration of SAHA observed after administration. IV SAHA was administered at 200 mg infused over two hours. The oral SAHA was administered in a single capsule at 200 mg. Tables 2 and 3 summarize the results of an HPLC assay (LCMS using a deuterated standard) that quantitates the amount of SAHA in the blood plasma of the patients versus time, using acetylated histone-4 (α-AcH4) as a marker.

TABLE 2

Serum Plasma Levels of Oral SAHA - Patient #1

|  | IV | Oral (fasting) | Oral (nonfasting) |
|---|---|---|---|
| $C_{max}$ (ng/ml) | 1329 | 225 | 328 |
| $t_{1/2}$ (min) | 20 | 80 | 64 |
| AUC (ng/ml)min | 153,000 | 25,000 | 59,000 |

TABLE 3

Serum Plasma Levels of Oral SAHA - Patient #2

|  | IV | Oral (fasting) | Oral (nonfasting) |
|---|---|---|---|
| $C_{max}$ (ng/ml) | 1003 | 362 | 302 |
| $t_{1/2}$ (min) | 21 | 82 | 93 |
| AUC (ng/ml)min | 108,130 | 63,114 | 59,874 |

Figure 9B:
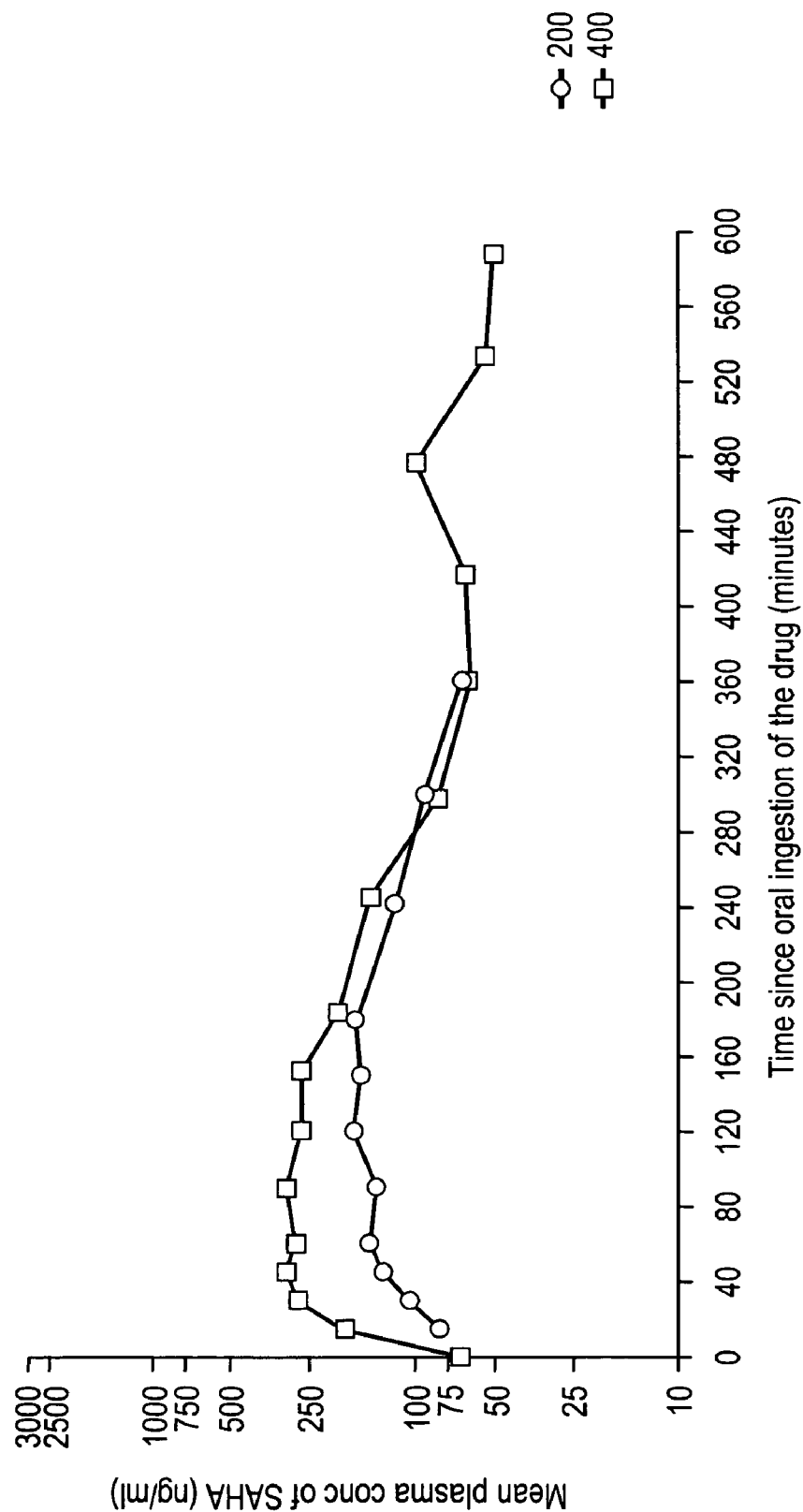
Figure 11:
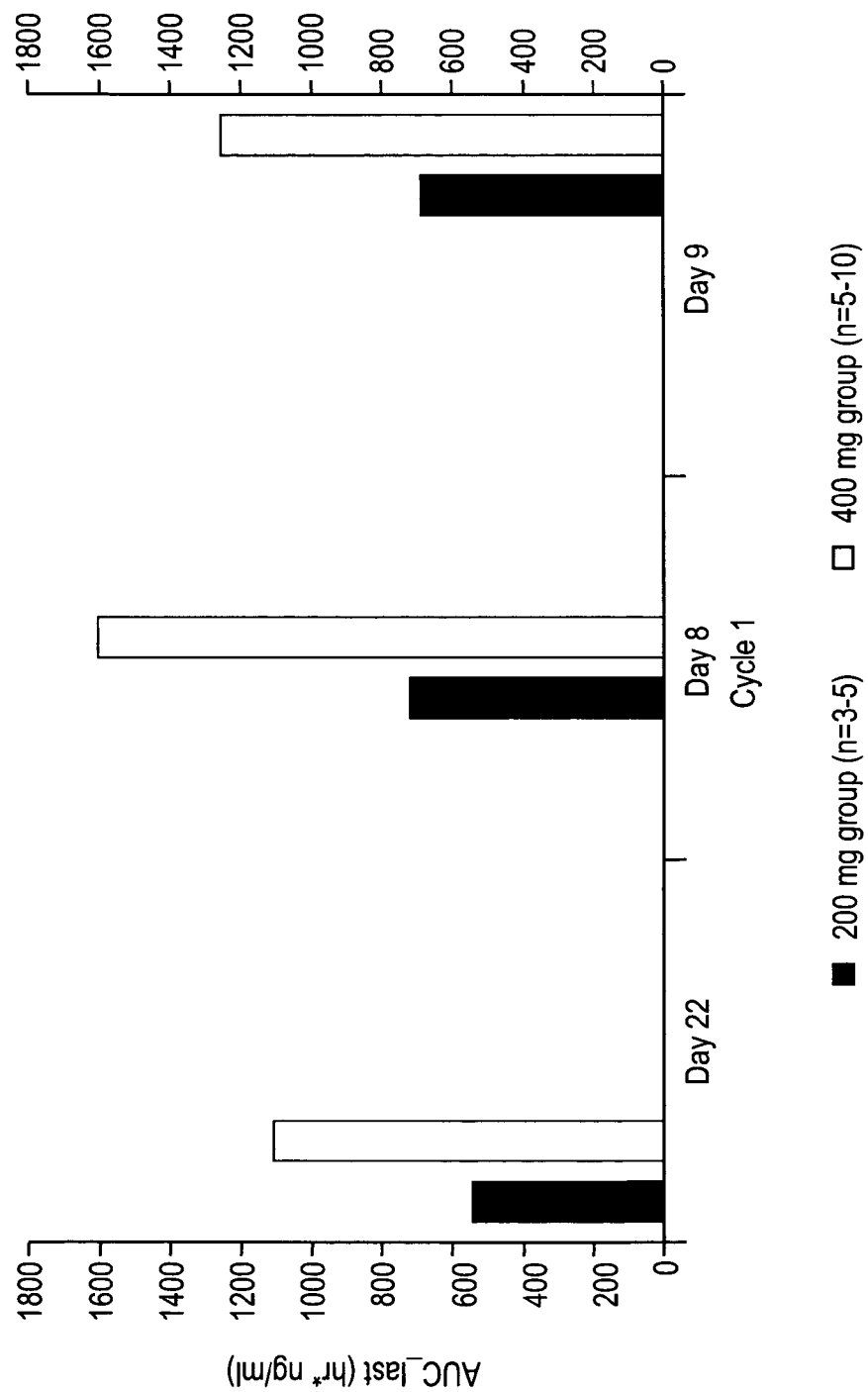
FIG. 11 shows the AUC (ng/ml/hr) of a SAHA 200 mg and 400 mg oral dose, on Days 8, 9 and 22.

FIGS. 1 to 8 are HPLC slides showing the amount of α-AcH4 in patients in Cohorts I and II, measured at up to 10 hours after receiving the oral dose, compared with the α-AcH4 levels when SAHA was administered intravenously. FIG. 9 shows the mean plasma concentration of SAHA (ng/ml) at the indicated time points following administration. FIG. 9A: Oral dose (200 mg and 400 mg) under fasting on Day 8. FIG. 9B: Oral dose (200 mg and 400 mg) with food on Day 9. FIG. 9C: IV dose on day 1. FIG. 10 shows the apparent half-life of a SAHA 200 mg and 400 mg oral dose, on Days 8, 9 and 22. FIG. 11 shows the AUC (ng/ml/hr) of a SAHA 200 mg and 400 mg oral dose, on Days 8, 9 and 22. FIG. 12 shows the bioavailability of SAHA after a 200 mg and 400 mg oral dose, on Days 8, 9 and 22.

EXAMPLE 3

Oral dosing of Suberoylanilide Hydroxamic Acid (SAHA)—Dose Escalation

In another experiment, twenty-five patients with solid tumors have been enrolled onto arm A, thirteen patients with Hodgkin's or non-Hodgkin's lymphomas have been enrolled onto arm B, and one patient with acute leukemia and one patient with myelodysplastic syndrome have been enrolled onto arm C, as shown in Table 4.

TABLE 4

Dose Escalation Scheme and Number of Patients on Each Dose Level

| Cohort | Dose (mg/day) | Dosing Schedule | #Days of Dosing | Rest Period | #Patients Enrolled (arm A/arm B/arm C)* |
|---|---|---|---|---|---|
| I | 200 | Once a day | Continuous | None | 6/0/0 |
| II | 400 | Once a day | Continuous | None | 5/4/2 |
| III | 400 | q 12 hours | Continuous | None | 6/3/0 |
| IV | 600 | Once a day | Continuous | None | 4/3/0 |
| V | 200 | q 12 hours | Continuous | None | 4/3/0 |
| VI | 300 | q 12 hours | Continuous | None | —/—/— |
|  |  |  |  | Sub-totals: | 25/13/2 |
|  |  |  |  |  | Total = 40 |

*Arm A = solid tumor,
arm B = lymphoma,
arm C = leukemia

Results:

Among eleven patients treated in Cohort II, one patient experienced the DLT of grade 3 diarrhea and grade 3 dehydration during the first treatment cycle. Nine patients were entered into Cohort III. Two patients were inevaluable for the 28-day toxicity assessment because of early study termination due to rapid progression of disease. Of the seven remaining patients, five experienced DLT during the first treatment cycle: diarrhea/dehydration (n=1), fatigue/dehydration (n=1), anorexia (n=1), dehydration (n=1) and anorexia/dehydration (n=1). These five patients recovered in approximately one week after the study drug was held. They were subsequently dose reduced to 400 mg QD which appeared to be well tolerated. The median days on 400 mg BID for all patients in Cohort III was 21 days. Based on these findings the 400 mg q12 hour dosing schedule was judged to have exceeded the maximally tolerated dose. Following protocol amendment, accrual was continued in cohort IV at a dose of 600 mg once a day. Of the seven patients enrolled onto cohort IV, two were inevaluable for the 28-day toxicity assessment because of early study termination due to rapid progression of disease. Three patients experienced DLT during the first treatment cycle: anorexia/dehydration/fatigue (n=1), and diarrhea/dehydration (n=2). The 600 mg dose was therefore judged to have exceeded the maximally tolerated dose and the 400 mg once a day dose was defined as the maximally tolerated dose for once daily oral administration. The protocol was amended to evaluate additional dose levels of the twice a day dosing schedule at 200 mg BID and 300 mg BID administered continuously.

The interim pharmacokinetic analysis was based on 18 patients treated on the dose levels of 200 mg QD, 400 mg QD, and 400 mg BID. In general, the mean estimates of $C_{max}$ and $AUC_{inf}$ of SAHA administered orally under fasting condition or with food increased proportionally with dose in the 200 mg to 400 mg dose range. Overall, the fraction of $AUC_{inf}$ due to extrapolation was 1% or less. Mean estimates for apparent half-life were variable across dose groups under fasting condition or with food, ranging from 61 to 114 minutes. The mean estimates of $C_{max}$, varies from 233 ng/ml (0.88 µM) to 570 ng/ml (2.3 µM). The bioavailable fraction of SAHA, calculated from the $AUC_{inf}$ values after the IV infusion and oral routes, was found to be approximately 0.48.

Peripheral blood mononuclear cells were collected pre-therapy, immediately post-infusion and between 2-10 hours after oral ingestion of the SAHA capsules to assess the effect of SAHA on the extent of histone acetylation in a normal host cell. Histones were isolated and probed with anti-acetylated histone (H3) antibody followed by HRP-secondary antibody. Preliminary analysis demonstrated an increase in the accumulation of acetylated histones in peripheral mononuclear cells that could be detected up to 10 hours after ingestion of SAHA capsules at 400 mg per day dose level.

Thirteen patients continued treatment for 3-12 months with responding or stable disease: thyroid (n=3), sweat gland (n=1), renal (n=2), larynx (n=1), prostate (n=1), Hodgkin's lymphoma (n=2), non-Hodgkin's lymphoma (n=2), and leukemia (n=1).

Six patients had tumor shrinkage on CT scans. Three of these six patients meet the criteria of partial response (one patient with metastatic laryngeal cancer and two patients with non-Hodgkin's lymphomas). These partial responses occurred at the dose levels of 400 mg BID (n=2) and 600 mg QD (n=1).

The dosages described above have also been administered twice daily intermittently. Patients have received SAHA twice daily three to five days per week. Patient response has been seen with administration of SAHA twice daily at 300 mg for three days a week.

EXAMPLE 4

Intravenous Dosing of SAHA

Table 5 shows a dosing schedule for patients receiving SAHA intravenously. Patients begin in Cohort I, receiving 300 mg/m² of SAHA for five consecutive days in a week for one week, for a total dose of 1500 mg/m². Patients were then observed for a period of two weeks and continued to Cohort II, then progressed through the Cohorts unless treatment was terminated due to disease progression, tumor regression, unacceptable side effects or the patient received other treatment.

TABLE 5

Standard Dose Escalation for Intravenously-Administered SAHA

| Cohort | Dose (mg/m²) | Number of Days/Week | Number of Consecutive Weeks | Observation Period (Weeks) | Total Dose (mg/m²) |
|---|---|---|---|---|---|
| I | 300 | 5 | 1 | 2 | 1500 |
| II | 300 | 5 | 2 | 2 | 3000 |
| III | 300 | 5 | 3 | 1* | 4500 |
| IV | 600 | 5 | 3 | 1* | 9000 |
| V | 800 | 5 | 3 | 1* | 13500 |
| VI | 1200 | 5 | 3 | 1* | 18000 |
| VII | 1500 | 5 | 3 | 1* | 22500 |

*Hematologic patients started at dose level III.

EXAMPLE 5

Treatment of CTCL/PTCL With SAHA

Patients with either CTCL or PTCL were administered oral SAHA once daily continuously at 400 mg or at 300 mg twice daily three to five days per week. Many CTCL patients had significant pruritis prior to treatment with SAHA. Significant reduction or resolution of pruritis upon administration of SAHA was reported in most patients.

In addition, a number of patients with mycosis fungoides or Sézary syndrome experienced partial response (PR). FIGS. 13A-D illustrate the response in CTCL patients to treatment with SAHA. FIG. 13A shows the decrease in patches on the arms of a CTCL patient after one week of SAHA administration. FIG. 13B shows the decrease in patches on the legs of the same CTCL patient after one week of SAHA administration. FIGS. 13C and 13D show the decrease in tumors on the face and head of a CTCL patient after eight weeks of SAHA administration.

EXAMPLE 6

Treatment of Metastatic Laryngeal Cancer

Patients with head and neck cancers were administered oral SAHA once daily at a dose of 400 mg. FIG. 14 shows response in a patient with metastatic laryngeal cancer after being administered SAHA for eight weeks.

While this invention has been particularly shown and described with references to preferred embodiments thereof, it will be understood by those skilled in the art that various changes in form and details may be made therein without departing from the meaning of the invention described. Rather, the scope of the invention is defined by the claims that follow:

REFERENCES

1. Sporn, M. B., Roberts, A. B., and Driscoll, J. S. (1985) in Cancer: Principles and Practice of Oncology, eds. Hellman, S., Rosenberg, S. A., and DeVita, V. T., Jr., Ed. 2, (J. B. Lippincott, Philadelphia), P. 49.
2. Breitman, T. R., Selonick, S. E., and Collins, S. J. (1980) Proc. Natl. Acad. Sci. USA 77: 2936-2940.
3. Olsson, I. L. and Breitman, T. R. (1982) Cancer Res. 42: 3924-3927.
4. Schwartz, E. L. and Sartorelli, A. C. (1982) Cancer Res. 42: 2651-2655.
5. Marks, P. A., Sheffery, M., and Rifkind, R. A. (1987) Cancer Res. 47: 659.
6. Sachs, L. (1978) Nature (Lond.) 274: 535.
7. Friend, C., Scher, W., Holland, J. W., and Sato, T. (1971) Proc. Natl. Acad. Sci. (USA) 68: 378-382.
8. Tanaka, M., Levy, J., Terada, M., Breslow, R., Rifkind, R. A., and Marks, P. A. (1975) Proc. Natl. Acad. Sci. (USA) 72: 1003-1006.
9. Reuben, R. C., Wife, R. L., Breslow, R., Rifkind, R. A., and Marks, P. A. (1976) Proc. Natl. Acad. Sci. (USA) 73: 862-866.
10. Abe, E., Miyaura, C., Sakagami, H., Takeda, M., Konno, K., Yamazaki, T., Yoshika, S., and Suda, T. (1981) Proc. Natl, Acad, Sci. (USA) 78: 4990-4994.
11. Schwartz, E. L., Snoddy, J. R., Kreutter, D., Rasmussen, H., and Sartorelli, A. C. (1983) Proc. Am. Assoc. Cancer Res. 24: 18.
12. Tanenaga, K., Hozumi, M., and Sakagami, Y. (1980) Cancer Res. 40: 914-919.
13. Lotem, J. and Sachs, L. (1975) Int. J. Cancer 15: 731-740.
14. Metcalf, D. (1985) Science, 229: 16-22.
15. Scher, W., Scher, B. M., and Waxman, S. (1983) Exp. Hematol. 11: 490-498.
16. Scher, W., Scher, B. M., and Waxman, S. (1982) Biochem. & Biophys. Res. Comm. 109: 348-354.
17. Huberman, E. and Callaham, M. F. (1979) Proc. Natl. Acad. Sci. (USA) 76: 1293-1297.
18. Lottem, J. and Sachs, L. (1979) Proc. Natl. Acad. Sci. (USA) 76: 5158-5162.
19. Terada, M., Epner, E., Nudel, U., Salmon, J., Fibach, E., Rifkind, R. A., and Marks, P. A. (1978) Proc. Natl. Acad. Sci. (USA) 75: 2795-2799.
20. Morin, M. J. and Sartorelli, A. C. (1984) Cancer Res. 44: 2807-2812.
21. Schwartz, E. L., Brown, B. J., Nierenberg, M., Marsh, J. C., and Sartorelli, A. C. (1983) Cancer Res. 43: 2725-2730.
22. Sugano, H., Furusawa, M., Kawaguchi, T., and Ikawa, Y. (1973) Bibl. Hematol. 39: 943-954.
23. Ebert, P. S., Wars, I., and Buell, D. N. (1976) Cancer Res. 36: 1809-1813.
24. Hayashi, M., Okabe, J., and Hozumi, M. (1979) Gann 70: 235-238.
25. Fibach, E., Reuben, R. C., Rifkind, R. A., and Marks, P. A. (1977) Cancer Res. 37: 440-444.
26. Melloni, E., Pontremoli, S., Damiani, G., Viotti, P., Weich, N., Rifkind, R. A., and Marks, P. A. (1988) Proc. Natl. Acad. Sci. (USA) 85: 3835-3839.
27. Reuben, R., Khanna, P. L., Gazitt, Y., Breslow, R., Rifkind, R. A., and Marks, P. A. (1978) J. Biol. Chem. 253: 4214-4218.
28. Marks, P. A. and Rifkind, R. A. (1988) International Journal of Cell Cloning 6: 230-240.
29. Melloni, E., Pontremoli, S., Michetti, M., Sacco, O., Cakiroglu, A. G., Jackson, J. F., Rifkind, R. A., and Marks, P. A. (1987) Proc. Natl. Acad. Sciences (USA) 84: 5282-5286.
30. Marks, P. A. and Rifkind, R. A. (1984) Cancer 54: 2766-2769.
31. Egorin, M. J., Sigman, L. M. VanEcho, D. A., Forrest, A., Whitacre, M. Y., and Aisner, J. (1987) Cancer. Res. 47: 617-623.
32. Rowinsky, E. W., Ettinger, D. S., Grochow, L. B., Brundrett, R. B., Cates, A. E., and Donehower, R. C. (1986) J. Clin. Oncol. 4: 1835-1844.
33. Rowinsky, E. L. Ettinger, D. S., McGuire, W. P., Noe, D. A., Grochow, L. B., and Donehower, R. C. (1987) Cancer Res. 47: 5788-5795.
34. Callery, P. S., Egorin, M. J., Geelhaar, L. A., and Nayer, M. S. B. (1986) Cancer Res. 46: 4900-4903.
35. Young, C. W. Fanucchi, M. P., Walsh, T. B., Blatzer, L., Yaldaie, S., Stevens, Y. W., Gordon, C., Tong, W., Rifkind, R. A., and Marks, P. A. (1988) Cancer Res. 48: 7304-7309.
36. Andreeff, M., Young, C., Clarkson, B., Fetten, J., Rifkind, R. A., and Marks, P. A. (1988) Blood 72: 186a.
37. Marks, P. A., Breslow, R., Rifkind, R. A., Ngo, L., and Singh, R. (1989) Proc. Natl. Acad. Sci. (USA) 86: 6358-6362.
38. Breslow, R., Jursic, B., Yan, Z. F., Friedman, E., Leng, L., Ngo, L., Rifkind, R. A., and Marks, P. A. (1991) Proc. Natl. Acad. Sci. (USA) 88: 5542-5546.
39. Richon, V. M., Webb, Y., Merger, R., et al. (1996) PNAS 93:5705-8.
40. Cohen, L. A., Amin, S., Marks, P. A., Rifkind, R. A., Desai, D., and Richon, V. M. (1999) Anticancer Research 19:4999-5006.
41. Grunstein, M. (1997) Nature 389:349-52.
42. Finnin, M. S., Donigian, J. R., Cohen, A., et al. (1999) Nature 401:188-193.
43. Van Lint, C., Emiliani, S., Verdin, E. (1996) Gene Expression 5:245-53.
44. Archer, S. Shufen, M. Shei, A., Hodin, R. (1998) PNAS 95:6791-96.
45. Dressel, U., Renkawitz, R., Baniahmad, A. (2000) Anticancer Research 20(2A):1017-22.
46. Lin, R. J., Nagy, L., Inoue, S., et al. (1998) Nature 391: 811-14.

What is claimed is:

1. A method of treating cutaneous T-cell lymphoma in a subject, said method comprising the step of orally administering to the subject a pharmaceutical composition comprising suberoylanilide hydroxamic acid (SAHA) or a pharmaceutically acceptable salt or hydrate thereof, represented by the structure:

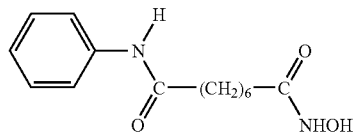

and a pharmaceutically acceptable carrier or diluent, wherein the SAHA or the pharmaceutically acceptable salt or hydrate thereof is administered daily at a dose of 400 mg once a day.

2. The method of claim 1, wherein said composition is contained within a gelatin capsule.

3. The method of claim 1, wherein said carrier or diluent is microcrystalline cellulose.

4. The method of claim 1, wherein said composition further comprises sodium croscarmellose as a disintegrating agent.

5. The method of claim 1, wherein said composition further comprises magnesium stearate as a lubricant.

6. A method of treating cutaneous T-cell lymphoma in a subject, which method comprises the step of orally administering to the subject a pharmaceutical composition comprising suberoylanilide hydroxamic acid (SAHA), represented by the structure:

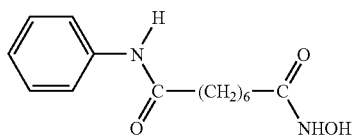

or a pharmaceutically acceptable salt or hydrate thereof and a pharmaceutically acceptable carrier or diluent, and wherein the SAHA or the pharmaceutically acceptable salt or hydrate thereof is administered at a dose of 300 mg twice daily on a schedule of daily administration for two consecutive weeks, then no administration for one week.

7. The method of claim 6, wherein said composition is contained within a gelatin capsule.

8. The method of claim 7, wherein said carrier or diluent is microcrystalline cellulose.

9. The method of claim 8, wherein said composition further comprises sodium croscarmellose as a disintegrating agent.

10. The method of claim 9, wherein said composition further comprises magnesium stearate as a lubricant.

11. The method according to claim 1 or claim 6, wherein said pharmaceutical composition comprises SAHA as the active ingredient.

* * * * *

UNITED STATES PATENT AND TRADEMARK OFFICE
CERTIFICATE OF CORRECTION

PATENT NO. : 7,399,787 B2  Page 1 of 1
APPLICATION NO. : 10/616649
DATED : July 15, 2008
INVENTOR(S) : Chiao et al.

It is certified that error appears in the above-identified patent and that said Letters Patent is hereby corrected as shown below:

On the title page,

[*] Notice: Subject to any disclaimer, the term of this patent is extended or adjusted under 35 USC 154(b) by (645) days Delete the phrase "by 645 days" and insert -- by 581 days --

Signed and Sealed this

Twenty-eighth Day of July, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,399,787 B2
APPLICATION NO. : 10/616649
DATED : July 15, 2008
INVENTOR(S) : Chiao et al.

Page 1 of 2

Figure 2:
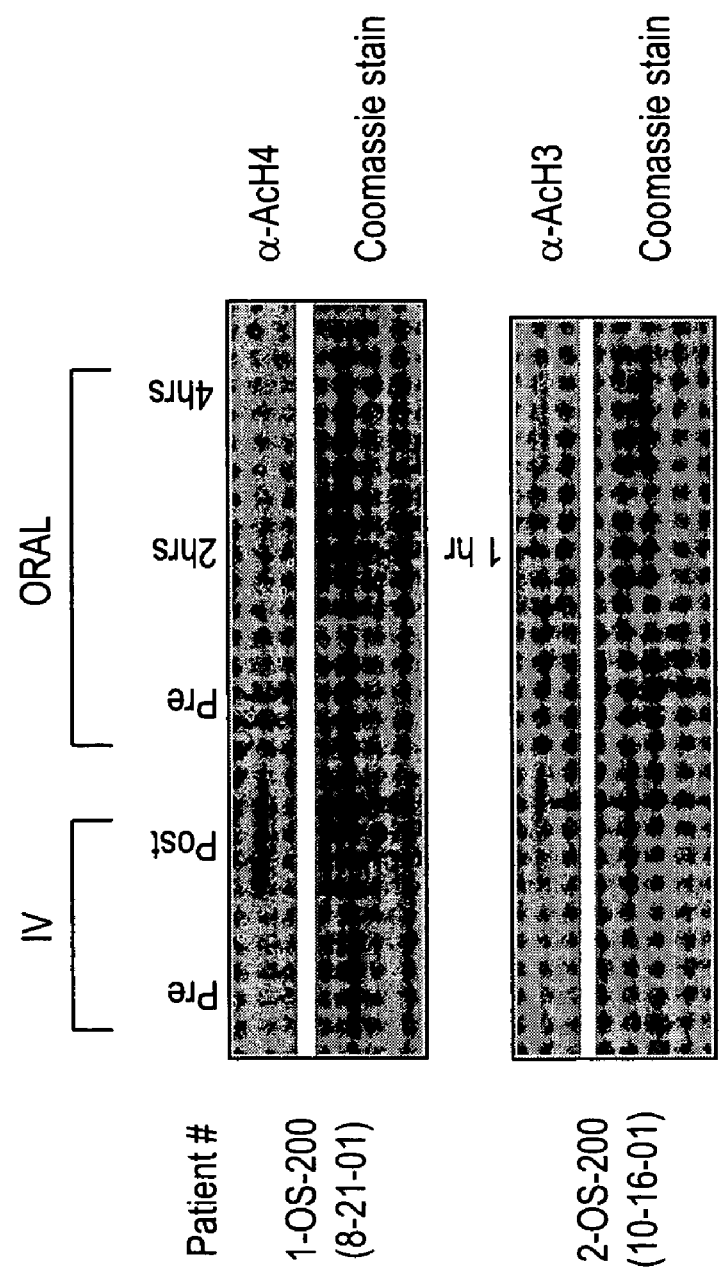
FIG. 2 is a picture of a Western blot (top panels) showing the quantities of acetylated histone-4 (α-AcH4) in the blood plasma of patients having a solid tumor, following an oral or intravenous (IV) dose of SAHA. IV and Oral SAHA were administered as in FIG. 1. The amount of α-AcH4 is shown at the indicated time points. The experiment is shown in duplicate (FIG. 2A and FIG. 2B). Bottom panels: Coomassie blue stain.
Figure 3:
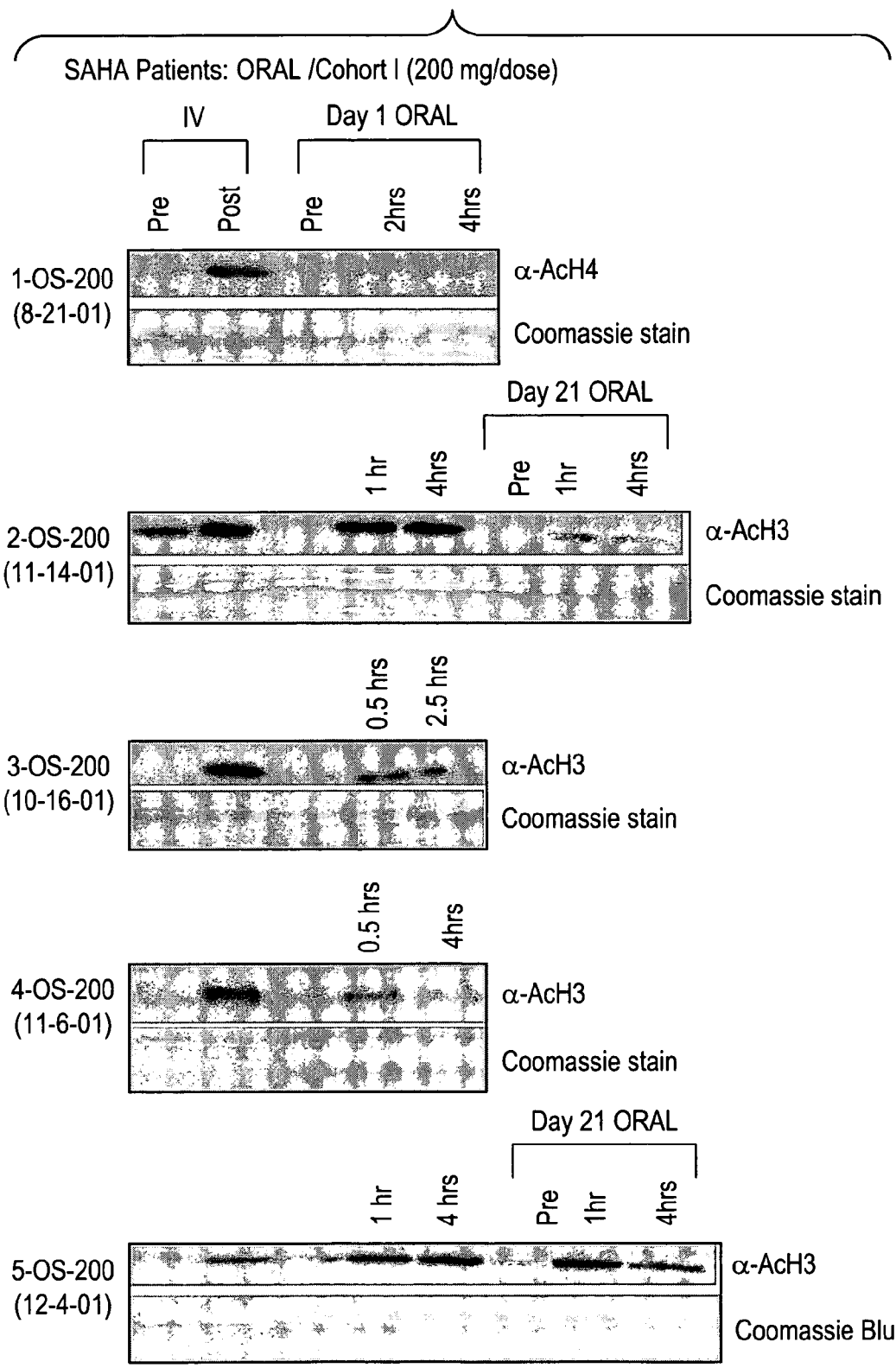
FIG. 3 is a picture of a Western blot (top panels) showing the quantities of acetylated histone-4 (α-AcH4) (FIG. 3A) and acetylated histone-3 (α-AcH3) (FIGS. 3B-E) in the blood plasma of patients following an oral or intravenous (IV) dose of SAHA, on Day 1 and Day 21. IV and Oral SAHA were administered as in FIG. 1. The amount of α-AcH4 or α-AcH3 is shown at the indicated time points. Bottom panels: Coomassie blue stain.
Figure 4:
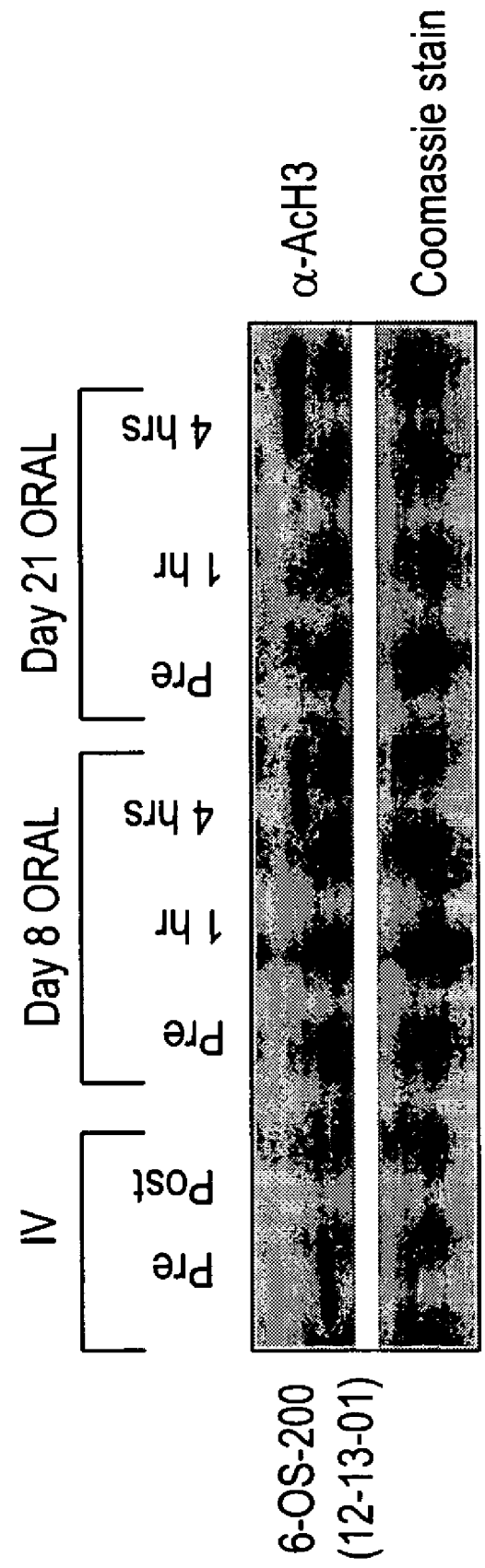
FIG. 4 is a picture of a Western blot (top panels) showing the quantities of acetylated histone-3 (α-AcH3) in the blood plasma of patients having a solid tumor, following an oral or intravenous (IV) dose of SAHA. IV and Oral SAHA were administered as in FIG. 1. The amount of α-AcH3 is shown at the indicated time points. Bottom panel: Coomassie blue stain.
Figure 5:
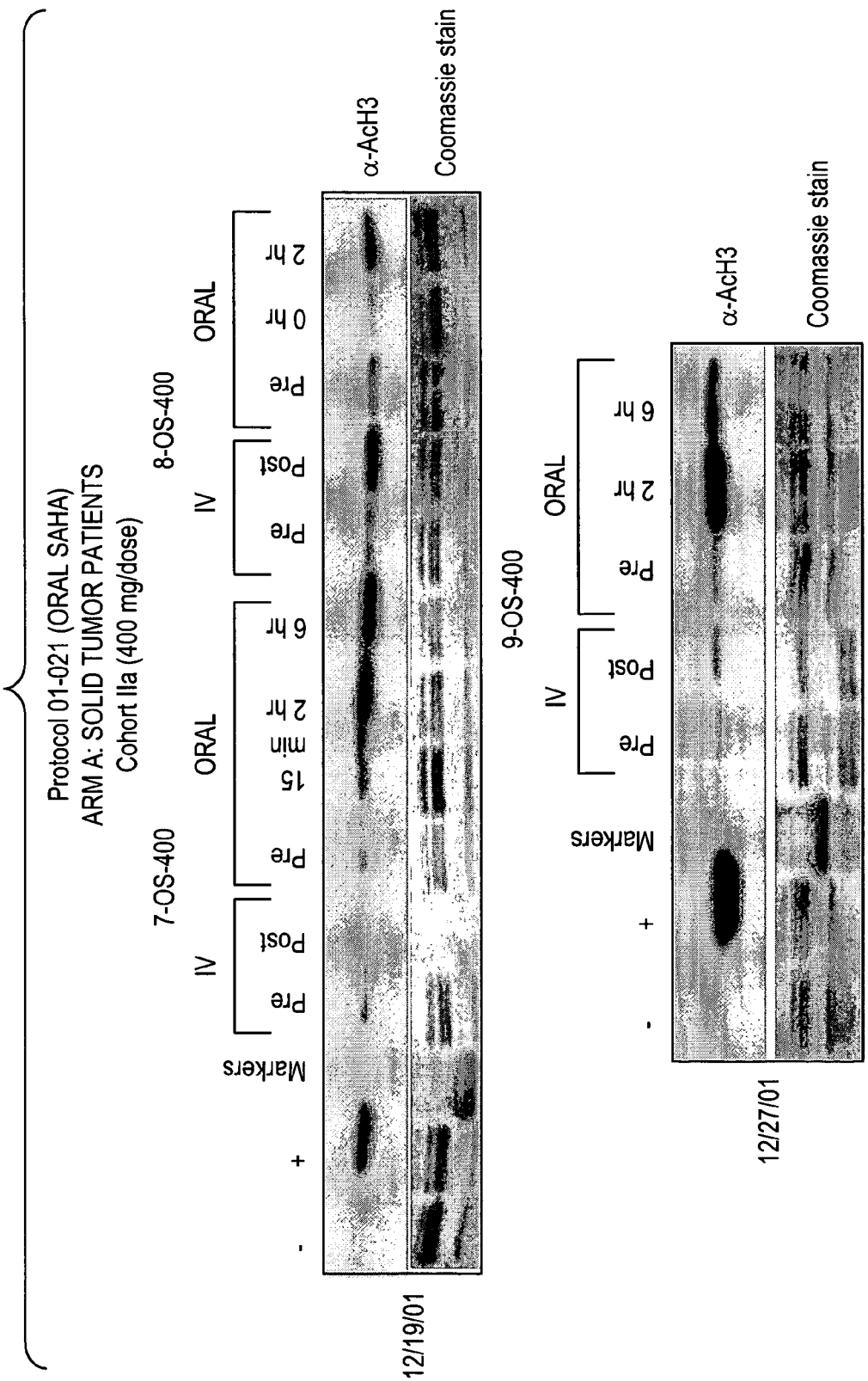
FIG. 5 is a picture of a Western blot (top panels) showing the quantities of acetylated histone-3 (α-AcH3) in the blood plasma of patients following an oral or intravenous (IV) dose of SAHA. IV SAHA was administered at 400 mg infused over two hours. Oral SAHA was administered in a single capsule at 400 mg. The amount of α-AcH4 is shown at the indicated time points. The experiment is shown in triplicate (FIGS. 5A and B). Bottom panels: Coomassie blue stain.
Figure 6:
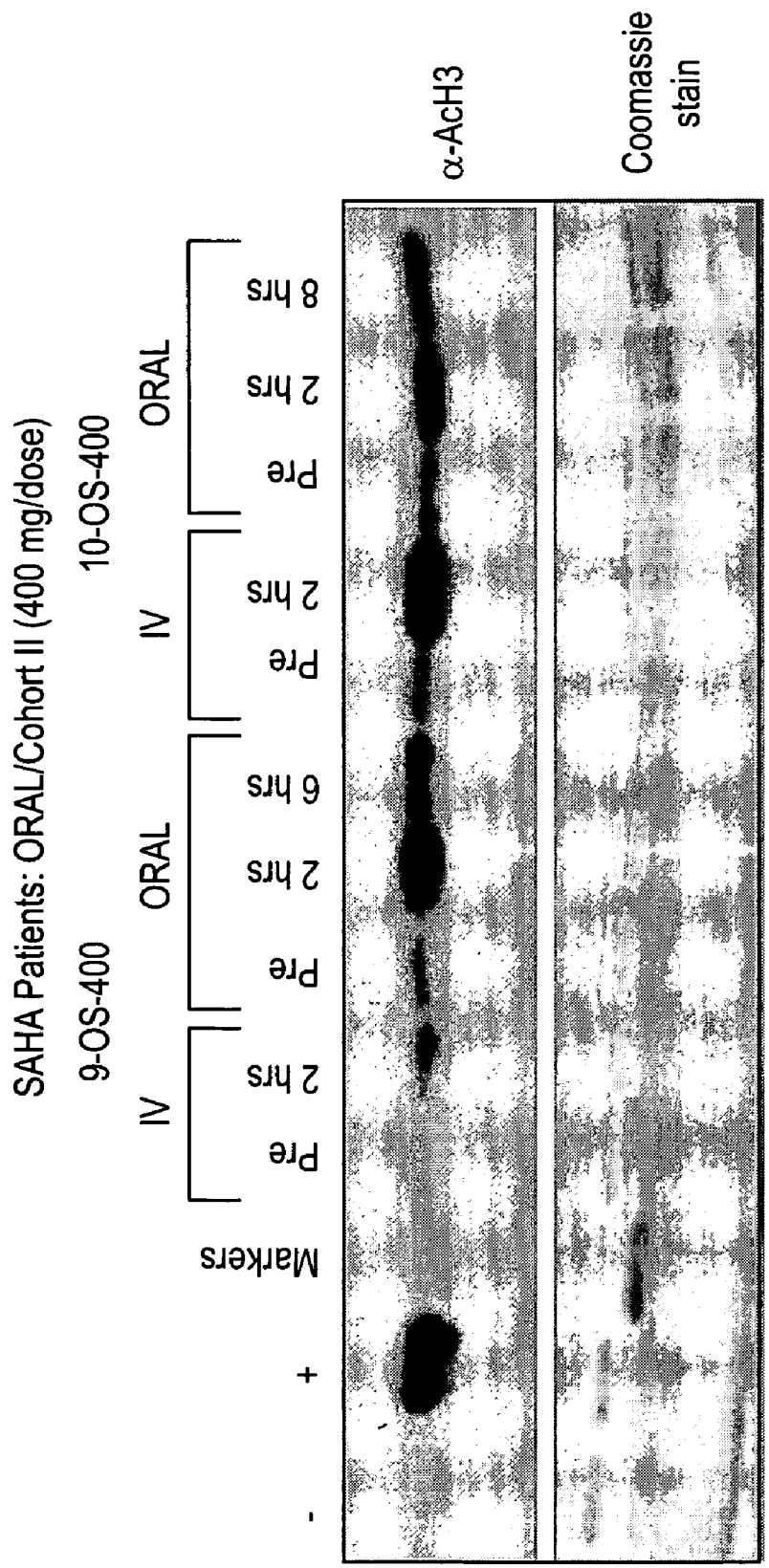
FIG. 6 is a picture of a Western blot (top panel) showing the quantities of acetylated histone-3 (α-AcH3) in the blood plasma of patients having a solid tumor, following an oral or intravenous (IV) dose of SAHA. IV and Oral SAHA were administered as in FIG. 5. The amount of α-AcH3 is shown at the indicated time points. Bottom panel: Coomassie blue stain.
Figure 7:
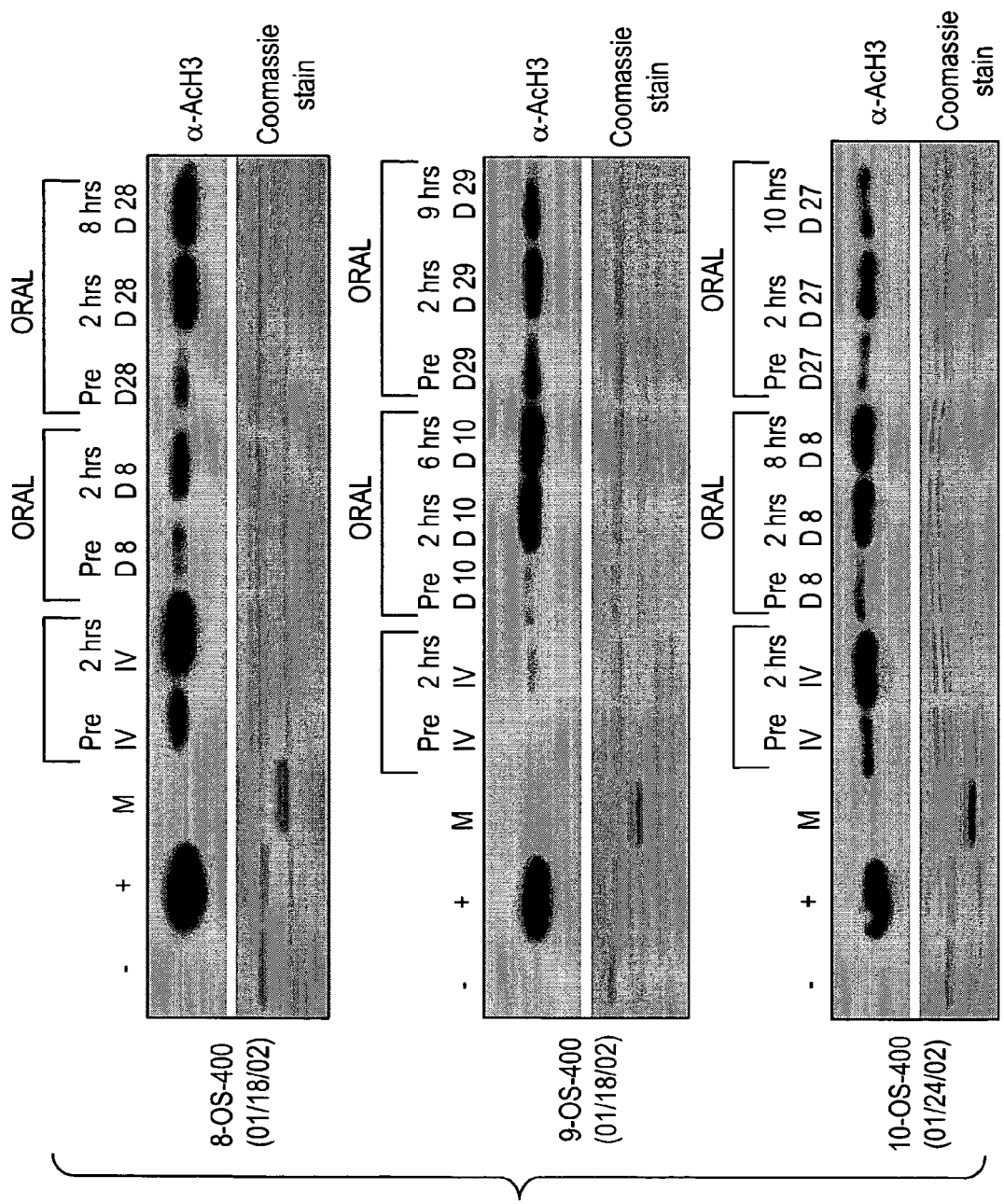
FIG. 7 is a picture of a Western blot (top panels) showing the quantities of acetylated histone-3 (α-AcH3) in the blood plasma of patients having a solid tumor following an oral or intravenous (IV) dose of SAHA, on Day 1 and Day 21. IV and Oral SAHA were administered as in FIG. 4. The amount of α-AcH4 or α-AcH3 is shown at the indicated time points. The experiment is shown in triplicate (FIG. 7A-C). Bottom panels: Coomassie blue stain.
Figure 8:
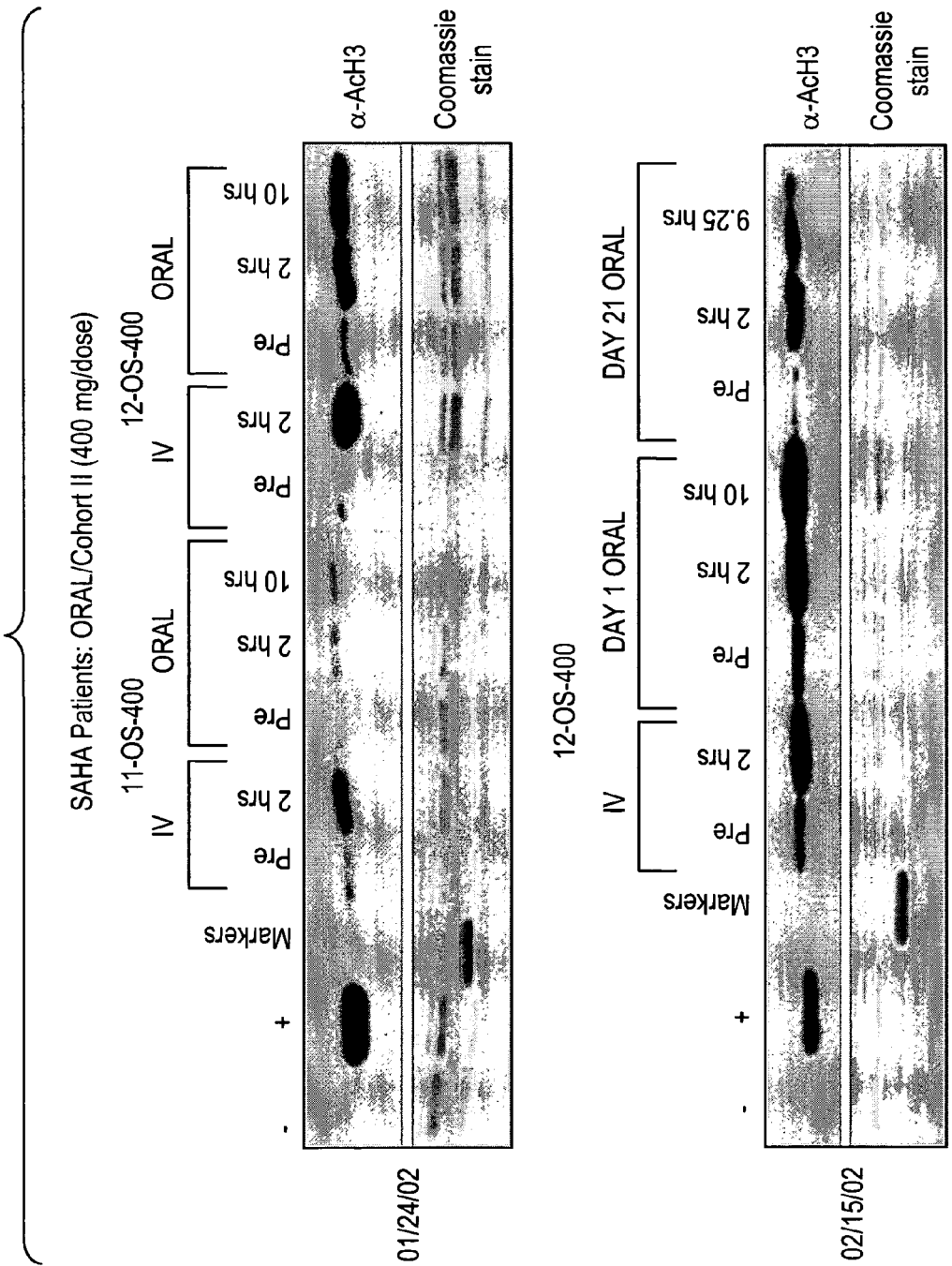
FIG. 8 is a picture of a Western blot (top panels) showing the quantities of acetylated histone-3 (α-AcH3) in the blood plasma of patients following an oral or intravenous (IV) dose of SAHA. IV and Oral SAHA were administered as in FIG. 5. The amount of a-AcH3 is shown at the indicated time points. Bottom panels: Coomassie blue stain.

It is certified that error appears in the above-identified patent and that said Letters Patent is hereby corrected as shown below:

In the drawings:

Drawing Sheet 2 of 19, Fig. 2, "α-AcH3" for Patient # 2-OS-200 should read --α-AcH4--.

In the specification:

Column 6, line 24, that portion reading "amount of α-AcH4 is" should read --amount of α-AcH3 is--; line 39, cancel the text "α-AcH4 or"; line 50, that portion reading "amount of a-AcH3" should read --amount of α-AcH3--.

Column 11, line 60, that portion reading "apicidin Ic, apicidin Ia, and" should read --apicidin Ic, apicidin IIa, and--.

Column 12, line 3, that portion reading "15,879-873" should read --15, 879-883--.

Column 13, line 2, that portion reading "aryl alkyloxy, aryloxy, arylalkyloxy" should read --aryl, alkyloxy, aryloxy, arylalkyloxy--.

Column 18, lines 19-20 and 22-23, cancel the text beginning with "$R_1$ is" to and ending "each of m"; lines 25-26, cancel the text "each of $R_1$ and $R_2$ is a fluoro group; and each of m".

Column 19, line 67, that portion reading "2,6-difuloro" should read --2,6-difluoro--.

Column 24, line 18, that portion reading "(34)" should read --(33)--; line 19, cancel the "/".

Column 25, line 25, that portion reading "(35)" should read --(34)--; line 38, insert the text --Y is selected from--.

Signed and Sealed this
Eleventh Day of March, 2014

Michelle K. Lee
*Deputy Director of the United States Patent and Trademark Office*

CERTIFICATE OF CORRECTION (continued)
U.S. Pat. No. 7,399,787 B2

Column 27, line 19, that portion reading "for use in the invention" should read --for use in the methods of the present invention--; line 45, that portion reading "or an enantiomer. In one" should read --or an enantiomer thereof. In one--.

Column 30, lines 44-45, cancel the text beginning with "wherein n is" to and ending "n=5.".

Column 36, line 28, that portion reading "hyperalgesia: inflammatory bowel disease;" should read --hyperalgesia; inflammatory bowel disease;--.

Column 40, line 52, that portion reading "Status of $\geqq 70\%$, and" should read --Status of $\geq 70\%$, and--.